(12) United States Patent
Andrews et al.

(10) Patent No.: US 6,172,064 B1
(45) Date of Patent: Jan. 9, 2001

(54) FORMAMIDES AS THERAPEUTIC AGENTS

(75) Inventors: Robert Carl Andrews, Durham; Marc Werner Andersen, Raleigh; David John Cowan, Hillsborough; David Norman Deaton, Cary; Scott Howard Dickerson, Chapel Hill; David Harold Drewry, Durham; Michael David Gaul, Apex; Michael Joseph Luzzio, Durham; Brian Edward Marron, Durham; Michael Howard Rabinowitz, Durham, all of NC (US)

(73) Assignee: Glaxo Wellcome Inc., Research Triangle Park, NC (US)

( * ) Notice: Under 35 U.S.C. 154(b), the term of this patent shall be extended for 0 days.

(21) Appl. No.: 09/382,333

(22) Filed: Aug. 25, 1999

Related U.S. Application Data

(60) Provisional application No. 60/097,956, filed on Aug. 26, 1998.

(51) Int. Cl.[7] ................. C07D 211/70; C07D 207/08; C07D 333/22; C07C 259/04; A61K 31/535; A61K 31/40; A61K 31/38; A61K 31/19; A61K 31/44

(52) U.S. Cl. ................ 514/237.8; 514/357; 514/428; 514/438; 514/575; 546/337; 546/168; 548/568; 549/76; 562/621; 562/623

(58) Field of Search .................... 562/621, 623; 514/515, 438, 357, 237.8, 428; 549/76; 546/337, 168; 548/568

(56) References Cited

U.S. PATENT DOCUMENTS

| | | |
|---|---|---|
| 4,738,803 | 4/1988 | Roques et al. |
| 4,996,358 | 2/1991 | Handa et al. |
| 5,239,078 | 8/1993 | Galardy et al. |
| 5,691,382 | 11/1997 | Crimmin et al. |
| 5,747,514 | 5/1998 | Beckett et al. |
| 5,985,911 * | 11/1999 | Davidsen et al. .................. 514/419 |
| 6,008,257 * | 12/1999 | Kruger et al. .................. 514/460 |
| 6,028,110 * | 2/2000 | Miller et al. .................. 514/575 |
| 6,057,369 * | 5/2000 | Groneberg et al. .................. 514/575 |

FOREIGN PATENT DOCUMENTS

| | | |
|---|---|---|
| 0 082 088 A1 | 12/1982 | (EP) . |
| 0 236 872 A2 | 2/1987 | (EP) . |
| 92/09556 | 6/1992 | (WO) . |
| 92/09563 | 6/1992 | (WO) . |
| 93/00327 | 1/1993 | (WO) . |
| 93/13741 | 7/1993 | (WO) . |
| 93/21942 | 11/1993 | (WO) . |
| 94/07527 | 4/1994 | (WO) . |
| 94/10990 | 5/1994 | (WO) . |
| 94/22309 | 10/1994 | (WO) . |
| 95/04735 | 2/1995 | (WO) . |
| 95/06031 | 3/1995 | (WO) . |
| 95/12603 | 5/1995 | (WO) . |
| 95/19956 | 7/1995 | (WO) . |
| 95/19965 | 7/1995 | (WO) . |
| 95/22966 | 8/1995 | (WO) . |
| 95/32944 | 12/1995 | (WO) . |
| 95/33709 | 12/1995 | (WO) . |
| 96/16027 | 5/1996 | (WO) . |
| 96/20918 | 7/1996 | (WO) . |
| 97/03783 | 2/1997 | (WO) . |
| 97/19053 | 5/1997 | (WO) . |
| 98/17643 | 4/1998 | (WO) . |

OTHER PUBLICATIONS

Akiyama, M. et al., "N–Hydroxy Amides, Part 5.+Synthesis and Properties of N–Hydroxypeptides having Leucine Enkephalin Sequences", Journ. Chem Soc., Perkin Trans. 1, (1986) p. 851–855.

Akiyama, M. et al., "Synthesis and Properties of Enkephalin Analogues Containing An N–Hydroxyamino Acid", Pept. Chem. (1985) 22:271–6.

Berner, I., et al., "Chiral Linear Hydroxamates as Biomimetic Analogues ferrioxamine and coprogena and their use in probing siderophore–receptor specifity in bacteria and fungi", Biol. Met. (1991) 4(3): 186–91.

Devlin, J., et al., "Studies Concerning the Antibiotic Actinonin. Part III. Synthesis of Structural analogues of actinonin by the Anhydride–Imide Method" J. Chem Soc. Perkin Trans. 1 (1975) 9:857–860.

Castelhano, et al., Chemical Abstracts, vol. 125, Abst. 143320.

Zaluski, et al., "New Bidentates as Full Inhibitors of Enkephalin–Degrading Enzymes: Synthesis and Analgesic Properties", J. Med. Chem Soc. Perkin 1 (1975) 9:830–41.

Floyd, et al., Chemical Abstracts, vol. 126, Abst. 212449.

* cited by examiner

Primary Examiner—Deborah C. Lambkin
(74) Attorney, Agent, or Firm—John L. Lemanowicz

(57) ABSTRACT

A family of compounds having the general structural formula

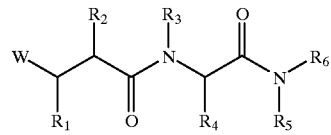

where W is a reverse hydroxamic acid group, and $R_1$, $R_2$, $R_3$, $R_4$, $R_5$ and $R_6$ are as described in the specification, or a pharmaceutically acceptable salt, solvate, biohydrolyzable ester, biohydrolyzable amide, affinity reagent, or prodrug thereof. Also described are methods for their preparation, pharmaceutical compositions including such compounds and their use in medicine.

21 Claims, No Drawings

FORMAMIDES AS THERAPEUTIC AGENTS

This application claims benefit of U.S. Provisional Application 60/097,956, filed Aug. 26, 1998 and GB 9818613.3, also filed Aug. 26, 1998.

FIELD OF THE INVENTION

The present invention provides novel compounds, novel compositions, methods of their use and methods of their manufacture, such compounds generally pharmacologically useful as agents in those disease states alleviated by the inhibition or antagonism of matrix metalloproteases, metalloproteases, and/or tumor necrosis factor-alpha (TNF), which pathologically involve aberrant extracellular matrix degradation, shedding of cell surface protein ectodomains, and/or TNF synthesis, such disease states including arthritis, tumor metastasis and diabetes. The aforementioned pharmacologic activities are useful in the treatment of mammals.

More specifically, the compounds of the present invention can be used in the treatment of osteoarthritis, rheumatoid arthritis, tumor invasion and metastasis, inflammatory bowel syndromes, periodontal disease, aberrant angiogenesis, corneal ulceration and the complications of diabetes. At the present time, there is a need in the areas of rheumatology, oncology, dentistry, opththalmology, gastroenterology, cardiology, neurology, nephrology, infectious disease and endocrinology therapy for such agents.

BACKGROUND OF THE INVENTION

The matrix metalloprotease (MMP) family of zinc endoproteases includes fibroblast collagenase (MMP-1, collagenase-1), neutrophil collagenase (MMP-8, collagenase-2), chondrocyte collagenase (MMP-13, collagenase-3), gelatinases A and B (MMP's 2 and 9), and members of the stromelysin family such as stromelysin-1 (MMP-3), stromelysin-3 (MMP-11), and matrilysin (MMP-7). These enzymes accelerate breakdown of connective tissue by catalyzed resorption of the extracellular matrix. This is a feature of diverse pathologies; therefore, inhibitors of one or more of the matrix metalloproteases would have utility in a wide range of disease states such as in abrogating the initiation of tumor metastasis and angiogenesis and in halting the pathogenesis of demyelinating diseases of the nervous system, multiple sclerosis being one example. MMP inhibitors would also find utility in diseases involving connective tissue degradation in the joint, as occurs in osteoarthritis and rheumatoid arthritis. MMP's-1 and -3 have been found in elevated levels in the synovial fluid of patients with rheumatoid arthritis and osteoarthritis.

Collagenase-3 (MMP-13) is a member of the family of MMP's which preferentially digest collagen. Collagenase-3 is one of the more newly characterized MMP's; biochemical studies on the recombinant protein have demonstrated that it cleaves type II collagen, the predominant matrix component of articular cartilage, more efficiently than either MMP-1 or MMP-2 and that it is expressed by chondrocytes in osteoarthritic cartilage. These data would implicate collagenase-3 as a significant target in rheumatoid arthritis and osteoarthritis for inhibition by MMP inhibitors.

Compounds which inhibit the activities of one or more of the matrix metalloproteases are recognized as having therapeutic benefit in one or more pathologies where MMP activity is upregulated, such as;

i) inflammatory/autoimmune diseases, which include, but not limited to rheumatoid arthritis, osteoarthritis, Crohn's disease and other inflammatory bowel diseases, periodontal disease, gingivitis, and corneal ulceration;

ii) diseases of cancer and malignancy, including but not limited to cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, tumor invasion, and metastatic and angiogenic events thereof;

iii) cardiovascular diseases, including but not limited to atherosclerosis, and restenosis;

iv) metabolic diseases, including but not limited to complications of diabetes, osteoporosis, and other disorders involving resorption of bone;

v) neurologic diseases, including but not limited to multiple sclerosis and other demyelination ailments;

vi) renal diseases, including but not limited to nephrotic syndromes and glomerulonephritis;

vii) infectious diseases, including but not limited to those mediated by viruses, bacteria, fungi;

viii) respiratory diseases, including but not limited to emphysema and COPD.

Many inhibitors of matrix metalloproteases have been disclosed, including some structure activity relationships for a series of carboxylalkylamine inhibitors. These molecules are exemplary for MMP inhibitors in general. They generally embody a functional group capable of tightly binding the zinc cofactor at the enzyme active site, which is contained within a peptidic or pseudopeptide structure. Zinc binding groups among the MMP inhibitor art have included hydroxamic acid, reverse hydroxamic acid, thiol, carboxylate, and phosphinate.

Hydroxamate metalloprotease inhibitors disclosed in the art usually have the following general structure (I):

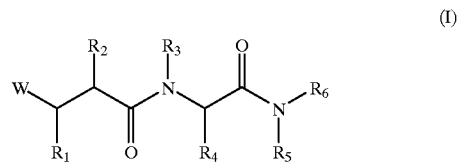

(I)

where W is a zinc-chelating acyl derivative group of the formula —C(O)NHOH (which by convention and in this application are referred to as "forward hydroxamates") or a zinc-chelating substituted amine group of the formula —NH(OH)C(O)R (which by convention and in this application are referred to as "reverse hydroxamates"), where R is usually hydrogen or alkyl. The other substituents vary according to specifications expressed by the art disclosure. It is understood and demonstrated that variations in these substituents can have dramatic effects on potency and selectivities between the matrix metalloproteases.

Suppression of MMP activity in conditions characterized by its overproduction would be of benefit, and compounds which inhibit MMP's would act in this manner at a specific target and be useful and of benefit. The present invention fills this need by providing compounds that are potent, specific, orally active inhibitors of matrix metalloproteases.

Tumor necrosis factor-α (TNFα), hereinafter called "TNF", is a mammalian protein capable of inducing cellular effects by virtue of its interaction with specific cellular receptors. It is initially characterized and so named due to its ability to cause death of cancerous cells. It is produced primarily by activated monocytes and macrophages. Human TNF is produced as a larger pro-form of 26 kD which is processed to a secreted 17 kD mature form by proteolytic processing of the alanine-76-valine-77 peptide bond.

Recently, certain compounds having matrix metalloprotease-inhibiting activity have been found to inhibit the release of mature 17 kD TNF from cells. Further, these inhibitors also protect mice from a lethal dose of endotoxin indicating that the compounds can inhibit TNF secretion in vivo. These compounds inhibit the cell-associated proteolytic processing of the 26 kD pro-TNF to the mature 17 kD form. The proteolytic activity is thought to reside in an intracellular or cell-associated specific enzyme or family of enzymes, which by convention is called a "TNF convertase", distinct from the matrix metalloproteases but related in that both contain a zinc cation at the active site. TNF convertase enzymatic activity can be detected in monocyte membrane fractions, and the enzyme activity can be inhibited by certain matrix metalloprotease-inhibiting compounds.

A metalloprotease is thought to mediate the proteolysis of the cell surface-IgE receptor CD23. Certain of the CD23-derived peptides possess proinflammatory biological activities mimicking those of cytokines, including TNFα.

Metalloprotease like activity is also thought to contribute to the shedding of certain cell surface protein ectodomains such as L-selectin, fibronectin, thyrotropin stimulating hormone receptor, transforming growth factor alpha precursor, low density lipoprotein receptor, beta amyloid precursor protein, interleukin-6 receptor alpha subunit, Fas ligand, CD40 ligand, epidermal growth factor receptor, macrophage colony stimulating factor, interleukin-1 receptor type II, CD30, and tumor necrosis factor receptors type I and II.

TNF is known to mediate many biological responses in vivo Preclinical and clinical studies in animals and humans with specific TNF neutralizing antibodies, soluble TNF receptor constructs, and TNF detection techniques have implicated TNF as a mediator in numerous pathologies. The compounds of the present invention by virtue of their activity in inhibiting TNF production and/or their activity in preventing cell surface protein ectodomain shedding should show utility in the treatment of diverse pathologies such as:

i) inflammatory/autoimmune diseases, including but not limited to rheumatoid arthritis, osteoarthritis, Crohn's disease and other inflammatory bowel diseases and inflammatory gastrointestinal diseases, and systemic lupus erythematosis;

ii) reperfusion injuries, such as those caused by an initial ischemic event;

iii) systemic inflammatory response syndromes, including but not limited to sepsis, burn injury, pancreatitis, and adult respiratory distress syndrome;

iv) allergic and dermatologic diseases, including but not limited to delayed type hypersensitivity, psoriasis, asthma, eczema, allergic rhinitis, and allergic conjunctivitis;

v) cardiovascular diseases, including but not limited to hyperlipidemia, chronic obstructive pulmonary disease, myocardial infarction, atherosclerosis, and restenosis;

vi) metabolic diseases, including but not limited to osteoporosis, obesity, and diabetes;

vii) neurologic diseases, including but not limited to Alzheimer's disease, Parkinson's disease, multiple sclerosis, aneurism, and stroke;

viii) transplant rejection, including but not limited to organ transplant rejection and graft versus host disease;

ix) diseases of cancer and malignancy, including but not limited to cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, tumor invasion, and metastatic and angiogenic events thereof;

x) renal diseases, including but not limited to nephrotic syndromes and glomerulonephritis;

xi) cachexia and related wasting syndromes;

xii) infectious diseases, including but not limited to HIV infection and neuropathy, Epstein-Barr viral infection, herpes viral infection, malaria, meningitis, schistosomiasis, leprosy, hepatitis (which includes hepatitis A, hepatitis B, and hepatitis C), infectious arthritis, leishmaniasis, tuberculosis, Lyme disease, and viral encephalitis;

xiii) effects of disease therapy, including but not limited to cytokine therapy, chemotherapy, radiation therapy and therapies using anti-T-cell antibodies or cytotoxin-antibody conjugates; and xiv) ocular diseases, including but not limited to diabetic retinopathy and macular degeneration.

Suppression of TNF activity in conditions characterized by its overproduction would be of benefit, and compounds which inhibit TNF convertase would act in this manner at a specific target and be useful and of benefit. The present invention fulfills this need by providing potent, specific, orally active inhibitors of TNF-α release from cells acting via inhibition of TNF-α converting enzyme (TNFc).

Suppression of shedding of cell surface protein ectodomains in conditions characterized by an overactivity of such a shedding enzyme or enzymes would be of benefit, and compounds which inhibit this cell surface protein ectodomain shedding would be useful and of benefit. The present invention fills this need by providing potent, orally active inhibitors of shedding of cell surface protein ectodomains acting via inhibition of one or more specific enzymes which mediate this proteolytic event.

Furthermore, as described above, suppression of CD23 proteolysis in conditions characterized by an overabundance of CD23 proteolytic fragments would be of benefit, and compounds which inhibit CD23 proteolysis would be useful and of benefit. The present invention fills this need by providing potent inhibitors of CD23 proteolysis acting via inhibition of one or more specific enzymes which mediate this proteolytic event.

SUMMARY OF THE INVENTION

Accordingly, it is an object of the present invention to provide a potent, specific, orally active inhibitor of MMP's.

It is another object of the present invention to provide a potent, specific, orally active inhibitor of TNF-alpha release from monocyte cells acting via inhibition of TNF-alpha converting enzyme (TNFc).

Furthermore, it is another object of the present invention to provide a potent, orally active inhibitor of shedding of cell surface protein ectodomains acting via inhibition of one or more specific enzymes which mediate this proteolytic event.

Accordingly it is another object of the present invention to provide a potent inhibitor of CD23 proteolysis acting via inhibition of one or more specific enzymes which mediate this proteolytic event.

It is an object of the present invention to provide a compound of the formula

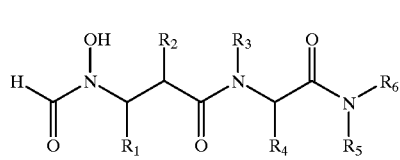

(II)

where $R_1$ is

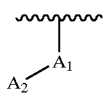

where $A_1$ is alkylene, alkenylene, alkynylene, cycloalkylene, cycloalkenylene, arylene, heterocyclylene, heteroarylene, or a direct bond;

where $A_2$ is alkyl, alkenyl, alkynyl, cycloalkyl, cycloalkenyl, heterocyclyl, heteroaryl, aryl, $NR_7R_8$, $OR_7$, $SR_7$, or hydrogen, where $R_7$ and $R_8$ are as defined below;

$R_2$ is

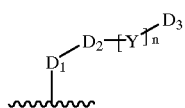

where
$D_1$ is alkylene, alkenylene, alkynylene, or a direct bond;
$D_2$ is arylene, heteroarylene, or a direct bond;
$D_3$ is aryl, heteroaryl, or heterocyclyl;
Y is alkylene, alkenylene, alkynylene, O, S, S(O), $SO_2$, $NR_9$, Se, Si, C(O), P(O)$OR_9$, P(O)$R_9$, C(O)O, C(O)$NR_9$, $NR_9$C(O), OC(O), OC(O)O, $NR_9$C(O)O, OC(O)$NR_9$, $NR_9$C(O)$NR_{10}$, or $T_1$—$T_2$ where
$T_1$ and $T_2$ are, independently, lower alkylene, lower alkenylene, lower alkynylene, O, S, S(O), $SO_2$, $NR_9$, Se, Si, C(O), P(O)$OR_9$, or P(O)$R_9$, where $R_9$ and $R_{10}$ are as defined below;

n=0 or 1;
$R_3$ is hydrogen or lower alkyl;
$R_4$ is

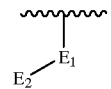

where
$E_1$ is alkylene, alkenylene, alkynylene, cycloalkylene, cycloalkenylene, arylene, heterocyclylene, heteroarylene, or a direct bond;
$E_2$ is hydrogen, $NR_{11}R_{12}$, $NR_{11}SO_2R_{12}$, $OR_{11}$, $SR_{11}$, S(O)$R_{11}$, $SO_2R_{11}$, alkyl, alkenyl, alkynyl, cycloalkyl, cycloalkenyl, heterocyclyl, aryl, or heteroaryl, where $R_{11}$ and $R_{12}$ are as defined below;
$R_5$ is hydrogen or lower alkyl;
$R_6$ is

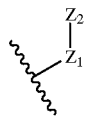

where
$Z_1$ is lower alkylene, lower alkenylene, lower alkynylene, cycloalkylene, cycloalkenylene, arylene, heterocyclylene, or a direct bond;
$Z_2$ is alkyl, alkenyl, alkynyl, cycloalkyl, cycloalkenyl, heterocyclyl, heteroaryl, aryl, $NR_{13}R_{14}$, $OR_{13}$, $SR_{,3}$, $NR_{13}SO_2R_{14}$, $NR_{13}C(O)R_{14}$, $C(O)NR_{13}$, $C(O)R_{13}$, $C(O)OR_{13}$, $OC(O)R_{13}$, $S(O)R_{13}$, $SO_2R_{13}$, $SO_2NR_{13}R_{14}$, $(O(CH_2)_qO)_mR_{13}$ or hydrogen, where m, q, $R_{13}$ and $R_{14}$ are as defined below;
$R_7$, $R_8$, $R_9$, $R_{10}$, $R_{11}$, $R_{12}$, $R_{13}$, and $R_{14}$ are, independently, hydrogen, alkyl, alkynyl, alkenyl, cycloalkyl, cycloalkenyl, aryl, heterocyclyl, or heteroaryl; and where m=1–10 and q=1–10, or a pharmaceutically acceptable salt, solvate, biohydrolyzable ester, biohydrolyzable amide, affinity reagent, or prodrug thereof.

DETAILED DESCRIPTION

The present invention provides a family of compounds having the general structural formula:

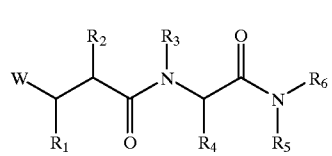

(I)

or a pharmaceutically acceptable salt, solvate, biohydrolyzable ester, biohydrolyzable amide, affinity reagent, or prodrug thereof, wherein
W is a reverse hydroxamic acid group;
$R_1$ is a substituent other than hydrogen;
$R_2$ is an alkylaryl or alkylheteroaryl substituent:
$R_4$ is a lipophilic substituent preferably with steric bulk proximal to the peptide backbone.

Such compounds are novel and are unknown in the art and, given the appropriate choice of $R_1$, $R_2$, $R_3$, $R_4$, $R_5$, and $R_6$ as described herein, show potent inhibition of MMP's, cell-free TNF convertase enzyme and TNF release from cells, and in some cases inhibit TNF convertase and TNF release from cells in preference to matrix metalloproteases. The alkylaryl or alkylheteroaryl nature of $R_2$ in combination with an appropriate choice of $R_1$, $R_3$, $R_4$, $R_5$, and $R_6$ as described herein is beneficial in achieving selective inhibition of one or more of the matrix metalloproteases (for example, collagenase-3). Such molecules can possess an improved therapeutic profile where inhibition of one or more of the matrix metalloproteases is associated with an adverse biological response or abnormal pathology. The alkylaryl or alkylheteroaryl nature of $R_2$ in combination with an appropriate choice of $R_1$, $R_3$, $R_4$, $R_5$, and $R_6$ as described herein is also beneficial in achieving selective inhibition of one or more of the matrix metalloproteases (for example, collagenase-3) in preference to TNF convertase inhibition and inhibition of TNF release from whole cells.

In particular, reverse hydroxamate compounds of the present invention include those of the formula (II):

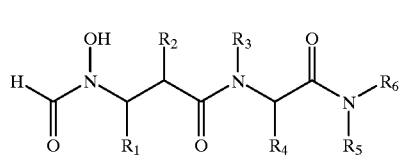

(II)

where
$R_1$ is

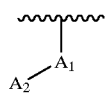

where
$A_1$ is alkylene, alkenylene, alkynylene, cycloalkylene, cycloalkenylene, arylene, heterocyclylene, heteroarylene, or a direct bond;
$A_2$ is alkyl, alkenyl, alkynyl, cycloalkyl, cycloalkenyl, heterocyclyl, heteroaryl, aryl, $NR_7R_8$, $OR_7$, $SR_7$, or hydrogen, where $R_7$ and $R_8$ are as defined below;
$R_2$ is

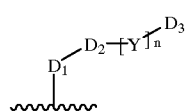

where
$D_1$ is alkylene, alkenylene, alkynylene, or a direct bond;
$D_2$ is alkylene, heteroarylene, or a direct bond;
$D_3$ is aryl, heteroaryl, or heterocyclyl;
Y is alkylene, alkenylene, alkynylene, O, S, S(O), $SO_2$, $NR_9$, Se, Si, C(O), $P(O)OR_9$, $P(O)R_9$, C(O)O, C(O) $NR_9$, $NR_9C(O)$, OC(O), OC(O)O, $NR_9C(O)O$, OC(O) $NR_9$, $NR_9C(O)NR_{10}$, or $T_1\text{—}T_2$ where $T_1$ and $T_2$ are, independently, lower alkylene, lower alkenylene, lower alkynylene, O, S, S(O), $SO_2$, $NR_9$, Se, Si, C(O), $P(O)OR_9$, or $P(O)R_9$, where $R_9$ and $R_{10}$ are as defined below;
n=0 or 1;
$R_3$ is hydrogen or lower alkyl;
$R_4$ is

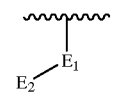

where
$E_1$ is alkylene, alkenylene, alkynylene, cycloalkylene, cycloalkenylene, arylene, heterocyclylene, heteroarylene, or a direct bond;
$E_2$ is hydrogen, $NR_{11}R_{12}$, $NR_{11}SO_2R_{12}$, $OR_{11}$, $SR_{11}$, $S(O)R_{11}$, $SO_2R_{11}$, alkyl, alkenyl, alkynyl, cycloalkyl, cycloalkenyl, heterocyclyl, aryl, or heteroaryl, where $R_{11}$ and $R_{12}$ are as defined below;
$R_5$ is hydrogen or lower alkyl;
$R_6$ is

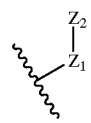

where
$Z_1$ is lower alkylene, lower alkenylene, lower alkynylene, cycloalkylene, cycloalkenylene, arylene, heterocyclylene, or a direct bond;
$Z_2$ is alkyl, alkenyl, alkynyl, cycloalkyl, cycloalkenyl, heterocyclyl, heteroaryl, aryl, $NR_{13}R_{14}$, $OR_{13}$, $SR_{13}$, $NR_{13}SO_2R_{14}$, $NR_{13}C(O)R_{14}$, $C(O)NR_{13}$, $C(O)R_{13}$, $C(O)OR_{13}$, $OC(O)R_{13}$, $S(O)R_{13}$, $SO_2R_{13}$, $SO_2NR_{13}R_{14}$, $(O(CH_2)_qO)_mR_{13}$ or hydrogen, where m, q, $R_{13}$ and $R_{14}$ are as defined below;
$R_7$, $R_8$, $R_9$, $R_{10}$, $R_{11}$, $R_{12}$, $R_{13}$, and $R_{14}$ are, independently, hydrogen, alkyl, alkynyl, alkenyl, cycloalkyl, cycloalkenyl, aryl, heterocyclyl, or heteroaryl; and where m=1–10 and q=1–10,
or a pharmaceutically acceptable salt, solvate, biohydrolyzable ester, biohydrolyzable amide, affinity reagent, or prodrug thereof.

Compounds of the present invention which are currently preferred for their high biological activity are listed below in Tables 1A and 1B; variables below are with reference to the generic structure (I).

TABLE IA
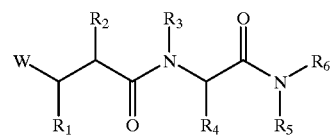
(I)
| Example | W | R₁ | R₂ | R₃ | R₄ | R₅ | R₆ |
|---------|---|----|----|----|----|----|----|
| 1 | N(OH)CHO | ⋮ | phenylpropyl | H | t-Bu | H | CH₃ |
| 2 | N(OH)CHO | ⋮ | 4-Cl-phenylpropyl | H | t-Bu | H | CH₃ |
| 3 | N(OH)CHO | ⋮ | thien-2-yl-propyl | H | t-Bu | H | CH₃ |
| 4 | N(OH)CHO | isopropyl | phenylpropyl | H | t-Bu | H | CH₃ |
| 5 | N(OH)CHO | ⋮ | phenylpropyl | H | 1-phenylethyl | H | CH₃ |

TABLE IA-continued
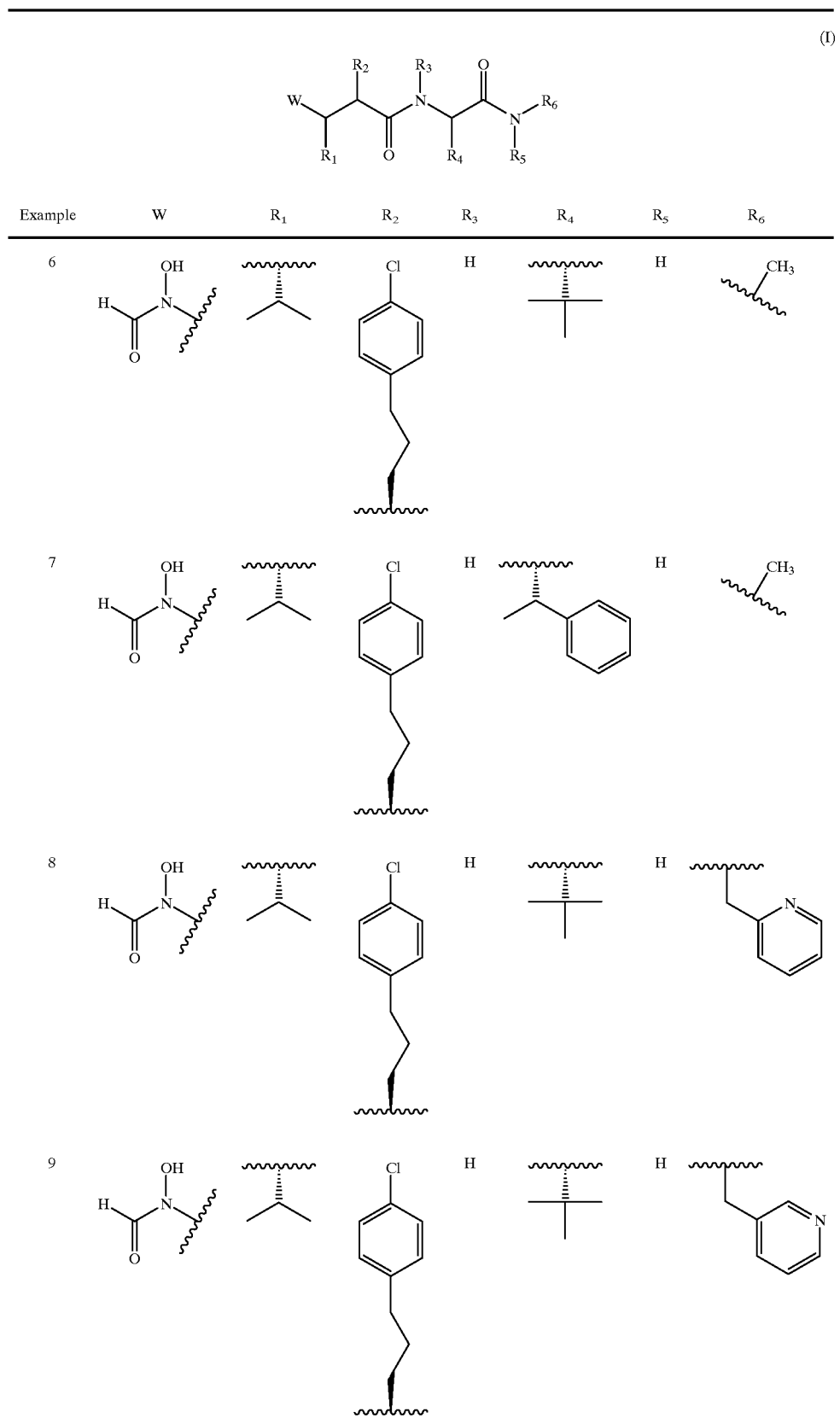

TABLE IA-continued
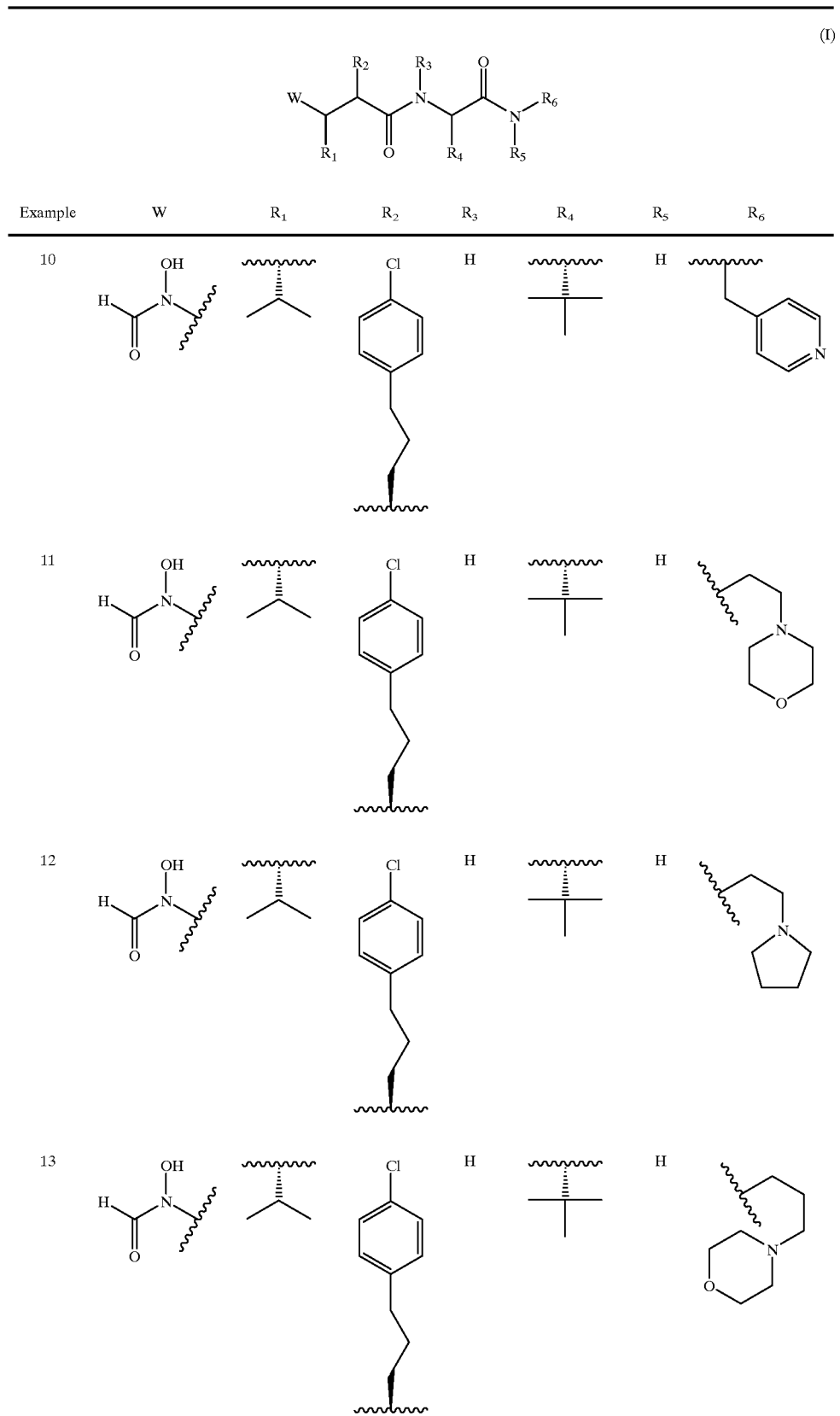

TABLE IA-continued
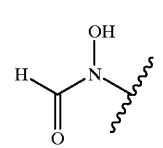
| Example | W | R₁ | R₂ | R₃ | R₄ | R₅ | R₆ |
|---|---|---|---|---|---|---|---|
| 14 |  | 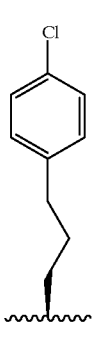 |  | H | 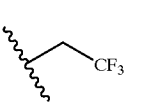 | H | 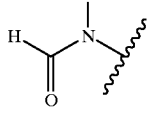 |
TABLE 1B
| Example | W | R₁ | R₂ | R₃ | R₄ | R₅ | R₆ |
|---|---|---|---|---|---|---|---|
| 15 | 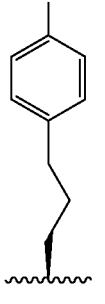 |  |  | H | 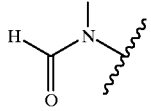 | H |  |
| 16 | 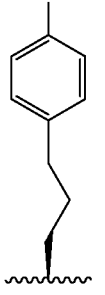 |  |  | H | 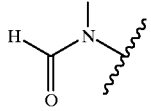 | H | 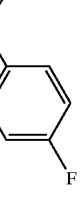 |

TABLE 1B-continued (I)

| Example | W | R₁ | R₂ | R₃ | R₄ | R₅ | R₆ |
|---------|---|----|----|----|----|----|----|
| 17 | H-C(=O)-N(OH)- | H | 4-Cl-C₆H₄-(CH₂)₄- | H | t-Bu | H | 4-MeO-C₆H₄-CH₂- |
| 18 | H-C(=O)-N(OH)- | iPr | 4-Cl-C₆H₄-(CH₂)₄- | H | t-Bu | H | -CH₂CH₂-O-CH₂CH₂-O-CH₂CH₂-O-CH₃ |
| 19 | H-C(=O)-N(OH)- | H | 4-Cl-C₆H₄-(CH₂)₄- | H | -CH(CH₃)-C₆H₅ | H | -CH₃ |
| 20 | H-C(=O)-N(OH)- | H | 4-Cl-C₆H₄-(CH₂)₄- | H | t-Bu | H | 2-pyridyl-CH₂- |

TABLE 1B-continued
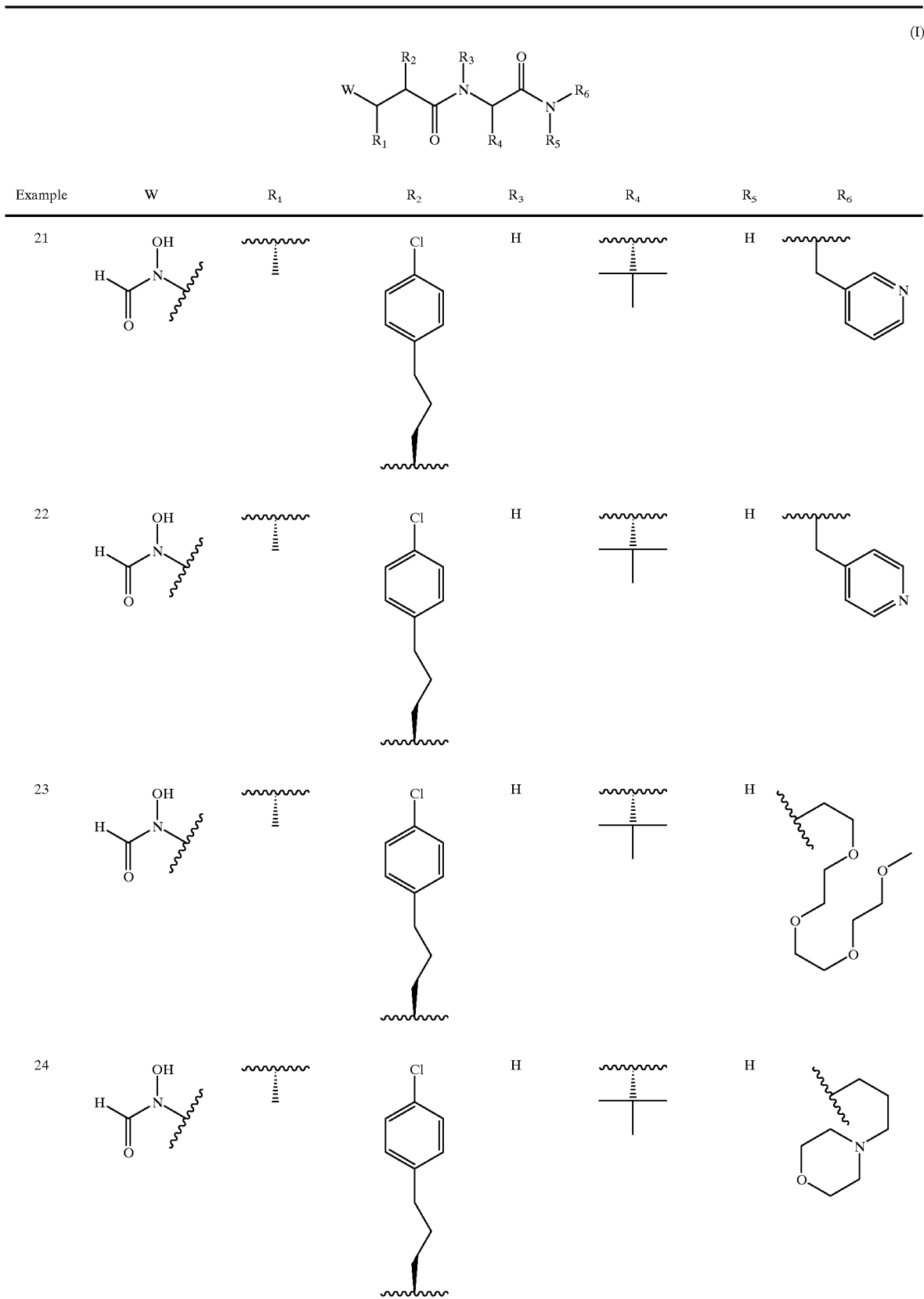

TABLE 1B-continued (I)

| Example | W | $R_1$ | $R_2$ | $R_3$ | $R_4$ | $R_5$ | $R_6$ |
|---------|---|-------|-------|-------|-------|-------|-------|
| 25 | H-C(=O)-N(OH)- | — | 4-Cl-C$_6$H$_4$-(CH$_2$)$_4$- | H | (R)-CH(CH$_3$)-C$_6$H$_5$ | H | -CH$_2$-(3-pyridyl) |
| 26 | H-C(=O)-N(OH)- | — | 4-Cl-C$_6$H$_4$-(CH$_2$)$_4$- | H | (R)-CH(CH$_3$)-C$_6$H$_5$ | H | morpholinopropyl |
| 27 | H-C(=O)-N(OH)- | — | 4-Cl-C$_6$H$_4$-(CH$_2$)$_4$- | H | -CH$_2$-C$_6$H$_5$ | H | morpholinopropyl |
| 28 | H-C(=O)-N(OH)- | — | 4-Cl-C$_6$H$_4$-(CH$_2$)$_4$- | H | -CH$_2$-(4-F-C$_6$H$_4$) | H | morpholinopropyl |

TABLE 1B-continued (I)

| Example | W | $R_1$ | $R_2$ | $R_3$ | $R_4$ | $R_5$ | $R_6$ |
|---------|---|-------|-------|-------|-------|-------|-------|
| 29 | N-formyl-N-hydroxyl | (stereo) | 4-Cl-phenyl-(CH2)3- | H | benzyl | H | 2-pyridylmethyl |
| 30 | N-formyl-N-hydroxyl | (stereo) | 4-Cl-phenyl-(CH2)3- | H | benzyl | H | 3-pyridylmethyl |
| 31 | N-formyl-N-hydroxyl | (stereo) | 4-Cl-phenyl-(CH2)3- | H | benzyl | H | 4-pyridylmethyl |
| 32 | N-formyl-N-hydroxyl | (stereo) | 4-Cl-phenyl-(CH2)3- | H | 4-F-benzyl | H | 3-pyridylmethyl |

TABLE 1B-continued (I)

| Example | W | R₁ | R₂ | R₃ | R₄ | R₅ | R₆ |
|---------|---|----|----|----|----|----|----|
| 33 | N-formyl-N-hydroxy | (attachment) | 4-chlorophenylbutyl | H | 1-phenylethyl | H | CH₃ |
| 34 | N-formyl-N-hydroxy | (attachment) | phenylbutyl | H | tert-butyl | H | 2-(pyridin-3-yl)ethyl |
| 35 | N-formyl-N-hydroxy | (attachment) | phenylbutyl | H | tert-butyl | H | 2-(pyridin-4-yl)ethyl |
| 36 | N-formyl-N-hydroxy | (attachment) | phenylbutyl | H | tert-butyl | H | 2-(2-(2-methoxyethoxy)ethoxy)ethyl |
| 37 | N-formyl-N-hydroxy | (attachment) | phenylbutyl | H | tert-butyl | H | (pyridin-2-yl)methyl |

TABLE 1B-continued (I)

| Example | W | R₁ | R₂ | R₃ | R₄ | R₅ | R₆ |
|---|---|---|---|---|---|---|---|
| 38 | HC(O)N(OH)– | – | –CH₂CH₂-phenyl | H | tert-butyl | H | –CH₂-(pyridin-3-yl) |
| 39 | HC(O)N(OH)– | – | –CH₂CH₂-phenyl | H | tert-butyl | H | –CH₂-(pyridin-4-yl) |
| 40 | HC(O)N(OH)– | – | –CH₂CH₂-phenyl | H | tert-butyl | H | cyclopropyl |
| 41 | HC(O)N(OH)– | – | –CH₂CH₂-phenyl | H | tert-butyl | H | –(CH₂)₂-morpholin-4-yl |
| 42 | HC(O)N(OH)– | – | –CH₂CH₂-phenyl | H | –CH₂-phenyl | H | CH₃ |
| 43 | HC(O)N(OH)– | – | –CH₂CH₂-phenyl | H | tert-butyl | H | –CH₂CH₂-(pyridin-2-yl) |

TABLE 1B-continued (I)

[Structure: W-CH(R1)-CH(R2)-C(=O)-N(R3)-CH(R4)-C(=O)-N(R5)(R6)]

| Example | W | R₁ | R₂ | R₃ | R₄ | R₅ | R₆ |
|---------|---|-----|-----|-----|-----|-----|-----|
| 44 | H-C(=O)-N(OH)- | methyl (dashed) | -(CH₂)₃-Ph | H | isobutyl | H | CH₃ |
| 45 | H-C(=O)-N(OH)- | methyl (dashed) | -(CH₂)₃-Ph | H | cyclohexyl | H | CH₃ |
| 46 | H-C(=O)-N(OH)- | methyl (dashed) | -(CH₂)₃-Ph | H | isopropyl | H | CH₃ |
| 47 | H-C(=O)-N(OH)- | methyl (dashed) | -(CH₂)₃-Ph | H | tert-butyl | H | CH₃ |
| 48 | H-C(=O)-N(OH)- | methyl (dashed) | -(CH₂)₃-C₆H₄-OMe (para) | H | tert-butyl | H | CH₃ |

TABLE 1B-continued
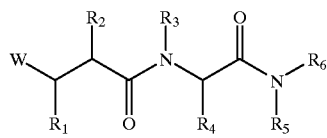
(I)
| Example | W | R₁ | R₂ | R₃ | R₄ | R₅ | R₆ |
|---|---|---|---|---|---|---|---|
| 49 | HC(O)N(OH)– | – | 4-(OPh)-C₆H₄-(CH₂)₃– | H | tBu | H | CH₃ |
| 50 | HC(O)N(OH)– | – | 4-(CF₃)-C₆H₄-(CH₂)₃– | H | tBu | H | CH₃ |
| 51 | HC(O)N(OH)– | – | 4-(tBu)-C₆H₄-(CH₂)₃– | H | tBu | H | CH₃ |
| 52 | HC(O)N(OH)– | – | 4-(CH₃)-C₆H₄-(CH₂)₃– | H | tBu | H | CH₃ |

TABLE 1B-continued
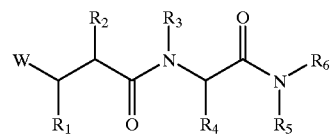
(I)
| Example | W | R₁ | R₂ | R₃ | R₄ | R₅ | R₆ |
|---|---|---|---|---|---|---|---|
| 53 | N(OH)CHO | H (dashed) | 4-F-C₆H₄-(CH₂)₃- | H | t-Bu | H | CH₃ |
| 54 | N(OH)CHO | H (dashed) | 4-Ph-C₆H₄-(CH₂)₃- | H | t-Bu | H | CH₃ |
| 55 | N(OH)CHO | CF₃ | C₆H₅-(CH₂)₃- | H | t-Bu | H | CH₃ |
| 56 | N(OH)CHO | CF₃ | C₆H₅-(CH₂)₃- | H | i-Pr | H | CH₃ |
| 57 | N(OH)CHO | CF₃ | C₆H₅-(CH₂)₃- | H | i-Bu | H | CH₃ |

TABLE 1B-continued (I)

| Example | W | R₁ | R₂ | R₃ | R₄ | R₅ | R₆ |
|---|---|---|---|---|---|---|---|
| 58 | HC(O)N(OH)– | –CH₂CH₂CF₃ | –(CH₂)₃–Ph | H | cyclohexyl | H | CH₃ |
| 59 | HC(O)N(OH)– | –CH₂CH₂CF₃ | –(CH₂)₃–Ph | H | –CH₂C(CH₃)₃ | H | CH₃ |
| 60 | HC(O)N(OH)– | –CH₃ | –(CH₂)₄–Ph | H | –C(CH₃)₃ | H | CH₃ |
| 61 | HC(O)N(OH)– | –CH₃ | –(CH₂)₅–Ph | H | –C(CH₃)₃ | H | CH₃ |
| 62 | HC(O)N(OH)– | –CH₃ | –(CH₂)₃–Ph | H | –CH₂–C₆H₄–OMe (p) | H | CH₃ |

TABLE 1B-continued
(I)
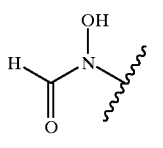
| Example | W | R₁ | R₂ | R₃ | R₄ | R₅ | R₆ |
|---|---|---|---|---|---|---|---|
| 63 |  | 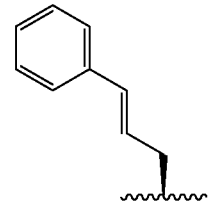 | 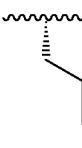 | H |  | H | 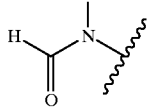 |
| 64 |  | 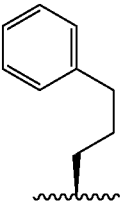 | 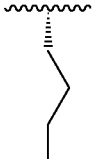 | H |  | H | 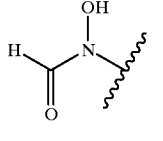 |
| 65 |  | 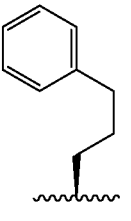 | 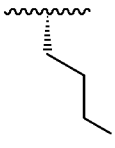 | H |  | H | 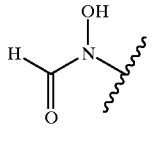 |
| 66 | 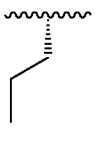 | 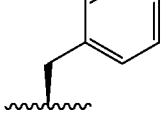 | 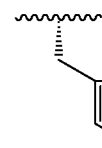 | H | 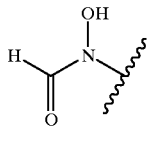 | H | H |
| 67 | 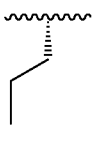 | 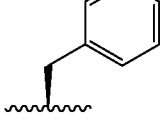 | 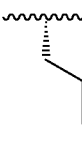 | H | 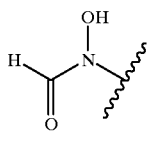 | H | H |
| 68 | 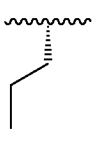 | 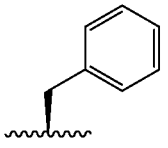 |  | H |  | H | CH₃ |

Compounds of the present invention which are currently preferred for their high biological activity are listed by name below in Tables 2A and 2B.

TABLE 2A

| Example | Chemical Name |
|---|---|
| 1 | (2R,3S)-3-(Formylhydroxyamino)-2-(3-phenyl-1-propyl)butanoic Acid [(1S)-2,2-Dimethyl-1-methylcarbamoyl)-1-propyl]amide |
| 2 | (2R,3S)-3-(Formylhydroxyamino)-2-(3-(4-chlorophenyl)-1-propyl)butanoic Acid [(1S)-2,2-Dimethyl-1-methylcarbamoyl)-1-propyl]amide |
| 3 | (2R,3S)-3-(Formylhydroxyamino)-2-(3-(2-thiophene)-1-propyl)butanoic Acid [(1S)-2,2-Dimethyl-1-methylcarbamoyl)-1-propyl]amide |
| 4 | (2R,3S)-3-(Formylhydroxyamino)-2-(3-phenyl-1-propyl)-4-methylpentanoic Acid [(1S)-2,2-Dimethyl-1-methylcarbamoyl)-1-propyl]amide |
| 5 | (2R,3S)-3-(Formylhydroxyamino)-2-(3-phenyl-1-propyl)butanoic Acid [(1S)-2-Phenyl-1-methylcarbamoyl)-1-propyl]amide |
| 6 | (2R,3S)-3-(Formylhydroxyamino)-2-(3-(4-chlorophenyl)-1-propyl)-4-methyl pentanoic Acid [(1S)-2,2-Dimethyl-1-methylcarbamoyl)-1-propyl]amide |
| 7 | (2R,3S)-3-(Formylhydroxyamino)-2-(3-(4-chlorophenyl)-1-propyl)-4-methyl pentanoic Acid [(1S)-2-Phenyl-1-methylcarbamoyl)-1-propyl]amide |
| 8 | (2R,3S)-3-(Formylhydroxyamino)-2-(3-(4-chlorophenyl)-1-propyl)-4-methylpentanoic Acid [(1S)-2,2-Dimethyl-1-(2-pyridylmethyl)carbamoyl)-1-propyl]amide |
| 9 | (2R,3S)-3-(Formylhydroxyamino)-2-(3-(4-chlorophenyl)-1-propyl)-4-methylpentanoic Acid [(1S)-2,2-Dimethyl-1-(3-pyridylmethyl)carbamoyl)-1-propyl]amide |
| 10 | (2R,3S)-3-(Formylhydroxyamino)-2-(3-(4-chlorophenyl)-1-propyl)-4-methylpentanoic Acid [(1S)-2,2-Dimethyl-1-(4-pyridylmethyl)carbamoyl)-1-propyl]amide |
| 11 | (2R,3S)-3-(Formylhydroxyamino)-2-(3-(4-chlorophenyl)-1-propyl)-4-methylpentanoic Acid [(1S)-2,2-Dimethyl-1-(2-(4-morpholino)-1-ethyl)carbamoyl)-1-propyl]amide |
| 12 | (2R,3S)-3-(Formylhydroxyamino)-2-(3-(4-chlorophenyl)-1-propyl)-4-methylpentanoic Acid [(1S)-2,2-Dimethyl-1-(2-(1-pyrrolidino)-1-ethyl)carbamoyl)-1-propyl]amide |
| 13 | (2R,3S)-3-(Formylhydroxyamino)-2-(3-(4-chlorophenyl)-1-propyl)-4-methylpentanoic Acid [(1S)-2,2-Dimethyl-1-(3-(4-morpholino)-1-propyl)carbamoyl)-1-propyl]amide |
| 14 | (2R,3S)-3-(Formylhydroxyamino)-2-(3-(4-chlorophenyl)-1-propyl)-4-methylpentanoic Acid [(1S)-2,2-Dimethyl-1-(2,2,2-trifluoroethyl)carbamoyl)-1-propyl]amide |

TABLE 2B

| Example | Chemical Name |
|---|---|
| 15 | (2R,3S)-3-(Formylhydroxyamino)-2-(3-(4-chlorophenyl)-1-propyl)-4-methylpentanoic Acid [(1S)-2,2-Dimethyl-(1-(2,2-dimethyl-1-propyl)carbamoyl)-1-propyl]amide |
| 16 | (2R,3S)-3-(Formylhydroxyamino)-2-(3-(4-chlorophenyl)-1-propyl)-butanoic Acid [(1S)-2,2-Dimethyl-(1-(4-fluorobenzyl)carbamoyl)-1-propyl]amide |
| 17 | (2R,3S)-3-(Formylhydroxyamino)-2-(3-(4-chlorophenyl)-1-propyl)-butanoic Acid [(1S)-2,2-Dimethyl-(1-(4-methoxybenzyl)carbamoyl)-1-propyl]amide |
| 18 | (2R,3S)-3-(Formylhydroxyamino)-2-(3-(4-chlorophenyl-1-propyl)-4-methylpentanoic Acid [(1S)-2,2-Dimethyl-(1-(tetraethyleneglycol methyl ether)carbamoyl)-1-propyl]amide |
| 19 | (2R,3S)-3-(Formylhydroxyamino)-2-(3-(4-chlorophenyl)-1-propyl)-butanoic Acid [(1S)-2-Phenyl-(1-methylcarbamoyl)-1-propyl]amide |
| 20 | (2R,3S)-3-(Formylhydroxyamino)-2-(3-(4-chlorophenyl)-1-propyl)-butanoic Acid [(1S)-2,2-Dimethyl-(1-(2-pyridylmethyl)carbamoyl)-1-propyl]amide |
| 21 | (2R,3S)-3-(Formylhydroxyamino)-2-(3-(4-chlorophenyl)-1-propyl)-butanoic Acid [(1S)-2,2-Dimethyl-(1-(3-pyridylmethyl)carbamoyl)-1-propyl]amide |
| 22 | (2R,3S)-3-(Formylhydroxyamino)-2-(3-(4-chlorophenyl)-1-propyl)-butanoic Acid [(1S)-2,2-Dimethyl-(1-(4-pyridylmethyl)carbamoyl)-1-propyl]amide |
| 23 | (2R,3S)-3-(Formylhydroxyamino)-2-(3-(4-chlorophenyl)-1-propyl)-butanoic Acid [(1S)-2,2-Dimethyl-(1-(tetraethyleneglycol methyl ether)carbamoyl)-1-propyl]amide |
| 24 | (2R,3S)-3-(Formylhydroxyamino)-2-(3-(4-chlorophenyl)-1-propyl)-butanoic Acid[(1S)-2,2-Dimethyl-(1-(3-(4-morpholino)-1-propyl)carbamoyl)-1-propyl]amide |
| 25 | (2R,3S)-3-(Formylhydroxyamino)-2-(3-(4-chlorophenyl)-1-propyl)-butanoic Acid [(1S)-2-Phenyl-(1-(3-pyridylmethyl)carbamoyl)-1-propyl]amide |
| 26 | (2R,3S)-3-(Formylhydroxyamino)-2-(3-(4-chlorophenyl)-1-propyl)butanoic Acid [(1S)-2-Phenyl-(1-(3-(4-morpholino)-1-propyl)carbamoyl)-1-propyl]amide |
| 27 | (2R,3S)-3-(Formylhydroxyamino)-2-(3-(4-chlorophenyl)-1-propyl)butanoic Acid [(1S)-(1-(3-(4-morpholino)-1-propyl)carbamoyl)-1-benzyl]amide |

TABLE 2B-continued

| Example | Chemical Name |
|---|---|
| 28 | (2R,3S)-3-(Formylhydroxyamino)-2-(3-(4-chlorophenyl)-1-propyl)butanoic Acid [(1S)-(1-(3-(4-morpholino)-1-propyl)carbamoyl)-1-(4-fluorobenzyl)]amide |
| 29 | (2R,3S)-3-(Formylhydroxyamino)-2-(3-(4-chlorophenyl)-1-propyl)butanoic Acid [(1S)-(1-(2-pyridylmethyl)carbamoyl)-1-benzyl]amide |
| 30 | (2R,3S)-3-(Formylhydroxyamino)-2-(3-(4-chlorophenyl)-1-propyl)butanoic Acid [(1S)-(1-(3-pyridylmethyl)carbamoyl)-1-benzyl]amide |
| 31 | (2R,3S)-3-(Formylhydroxyamino)-2-(3-(4-chlorophenyl)-1-propyl)butanoic Acid [(1S)-(1-(4-pyridylmethyl)carbamoyl)-1-benzyl]amide |
| 32 | (2R,3S)-3-(Formylhydroxyamino)-2-(3-(4-chlorophenyl)-1-propyl)butanoic Acid [(1S)-(1-(3-pyridylmethyl)carbamoyl)-1-(4-fluorobenzyl)]amide |
| 33 | (2R,3S)-3-(Formylhydroxyamino)-2-(3-(4-chlorophenyl)-1-propyl)butanoic Acid [(1S)-2-Phenyl-(1-methylcarbamoyl)-1-propyl]amide |
| 34 | (2R,3S)-3-(Formylhydroxyamino)-2-(3-phenyl-1-propyl)butanoic Acid [(1S)-2,2-Dimethyl-(1-(2-(3-pyridyl)-1-ethyl)carbamoyl)-1-propyl]amide |
| 35 | (2R,3S)-3-(Formylhydroxyamino)-2-(3-phenyl-1-propyl)butanoic Acid [(1S)-2,2-Dimethyl-(1-(2-(4-pyridyl)-1-ethyl)carbamoyl)-1-propyl]amide |
| 36 | (2R,3S)-3-(Formylhydroxyamino)-2-(3-phenyl-1-propyl)butanoic Acid [(1S)-2,2-Dimethyl-(1-(tetraethyleneglycol methyl ether)carbamoyl)-1-propyl]amide |
| 37 | (2R,3S)-3-(Formylhydroxyamino)-2-(3-phenyl-1-propyl)butanoic Acid [(1S)-2,2-Dimethyl-(1-(2-pyridylmethyl)carbamoyl)-1-propyl]amide |
| 38 | (2R,3S)-3-(Formylhydroxyamino)-2-(3-phenyl-1-propyl)butanoic Acid [(1S)-2,2-Dimethyl-(1-(3-pyridylmethyl)carbamoyl)-1-propyl]amide |
| 39 | (2R,3S)-3-(Formylhydroxyamino)-2-(3-phenyl-1-propyl)butanoic Acid [(1S)-2,2-Dimethyl-(1-(4-pyridylmethyl)carbamoyl)-1-propyl]amide |
| 40 | (2R,3S)-3-(Formylhydroxyamino)-2-(3-phenyl-1-propyl)butanoic Acid [(1S)-2,2-Dimethyl-(1-cyclopropylcarbamoyl)-1-propyl]amide |
| 41 | (2R,3S)-3-(Formylhydroxyamino)-2-(3-phenyl-1-propyl)butanoic Acid [(1S)-2,2-Dimethyl-(1-(3-(4-morpholino)-1-propyl)carbamoyl)-1-propyl]amide |
| 42 | (2R,3S)-3-(Formylhydroxyamino)-2-(3-phenyl-1-propyl)butanoic Acid [(1S)-(1-methylcarbamoyl)-1-benzyl]amide |
| 43 | (2R,3S)-3-(Formylhydroxyamino)-2-(3-phenyl-1-propyl)butanoic Acid [(1S)-2,2-Dimethyl-(1-(2-(2-pyridyl-1-ethyl)carbamoyl)-1-propyl]amide |
| 44 | (2R,3S)-3-(Formylhydroxyamino)-2-(3-phenyl-1-propyl)butanoic Acid [(1S)-3-Methyl-(1-methylcarbamoyl)-1-butyl]amide |
| 45 | (2R,3S)-3-(Formylhydroxyamino)-2-(3-phenyl-1-propyl)butanoic Acid [(1S)-(1-methylcarbamoyl)-1-cyclohexyl]amide |
| 46 | (2R,3S)-3-(Formylhydroxyamino)-2-(3-phenyl-1-propyl)butanoic Acid [(1S)-2-Methyl-(1-methylcarbamoyl)-1-propyl]amide |
| 47 | (2R,3S)-3-(Formylhydroxyamino)-2-(3-phenyl-1-propyl)butanoic Acid [(1S)-3,3-Dimethyl-(1-methylcarbamoyl)-1-butyl]amide |
| 48 | (2R,3S)-3-(Formylhydroxyamino)-2-(3-(4-methoxyphenyl)-1-propyl)butanoic Acid [(1S)-2,2-Dimethyl-(1-methylcarbamoyl)-1-propyl]amide |
| 49 | (2R,3S)-3-(Formylhydroxyamino)-2-(3-(4-phenoxyphenyl)-1-propyl)butanoic Acid [(1S)-2,2-Dimethyl-(1-methylcarbamoyl)-1-propyl]amide |
| 50 | (2R,3S)-3-(Formylhydroxyamino)-2-(3-(4-trifluoromethylphenyl)-1-propyl)butanoic Acid [(1S)-2,2-Dimethyl-(1-methylcarbamoyl)-1-propyl]amide |
| 51 | (2R,3S)-3-(Formylhydroxyamino)-2-(3-(4-t-butylphenyl)-1-propyl)butanoic Acid [(1S)-2,2-Dimethyl-(1-methylcarbamoyl)-1-propyl]amide |
| 52 | (2R,3S)-3-(Formylhydroxyamino)-2-(3-(4-methylphenyl)-1-propyl)butanoic Acid [(1S)-2,2-Dimethyl-(1-methylcarbamoyl)-1-propyl]amide |
| 53 | (2R,3S)-3-(Formylhydroxyamino)-2-(3-(4-fluorophenyl)-1-propyl)butanoic Acid [(1S)-2,2-Dimethyl-(1-methylcarbamoyl)-1-propyl]amide |
| 54 | (2R,3S)-3-(Formylhydroxyamino)-2-(3-(4-biphenyl)-1-propyl)butanoic Acid [(1S)-2,2-Dimethyl-(1-methylcarbamoyl)-1-propyl]amide |
| 55 | (2R,3S)-3-(Formylhydroxyamino)-2-(3-phenyl-1-propyl)-6,6,6-trifluorohexanoic Acid [(1S)-2,2-Dimethyl-(1-methylcarbamoyl)-1-propyl]amide |
| 56 | (2R,3S)-3-(Formylhydroxyamino)-2-(3-phenyl-1-propyl))-6,6,6-trifluorohexanoic Acid [(1S)-2-Methyl-(1-methylcarbamoyl)-1-propyl]amide |
| 57 | (2R,3S)-3-(Formylhydroxyamino)-2-(3-phenyl-1-propyl))-6,6,6-trifluorohexanoic Acid [(1S)-3-Methyl-(1-methylcarbamoyl)-1-butyl]amide |
| 58 | (2R,3S)-3-(Formylhydroxyamino)-2-(3-phenyl-1-propyl))-6,6,6-trifluorohexanoic Acid [(1S)-(1-methylcarbamoyl)-1-cyclohexyl]amide |
| 59 | (2R,3S)-3-(Formylhydroxyamino)-2-(3-phenyl-1-propyl))-6,6,6-trifluorohexanoic Acid [(1S)-3,3-Dimethyl-(1-methylcarbamoyl)-1-butyl]amide |
| 60 | (2R,3S)-3-(Formylhydroxyamino)-2-(4-phenyl-1-butyl)butanoic Acid [(1S)-2,2-Dimethyl-(1-methylcarbamoyl)-1-propyl]amide |
| 61 | (2R,3S)-3-(Formylhydroxyamino)-2-(5-phenyl-1-pentyl)butanoic Acid [(1S)-2,2-Dimethyl-(1-methylcarbamoyl)-1-propyl]amide |
| 62 | (2R,3S)-3-(Formylhydroxyamino)-2-(3-phenyl-1-propyl)butanoic Acid [(1S)-(1-methylcarbamoyl-1-(4-methoxybenzyl)]amide |
| 63 | (2R,3S)-3-(Formylhydroxyamino)-2-(3-phenyl-2-propene-1-yl)butanoic Acid [(1S)-(1-methylcarbamoyl)-1-benzyl]amide |

TABLE 2B-continued

| Example | Chemical Name |
| --- | --- |
| 64 | (2R,3S)-3-(Formylhydroxyamino)-2-(3-phenyl-1-propyl)butanoic Acid [(1S)-(1-methylcarbamoyl)-1-(4-phenylcarbonylamino)-1-butyl]amide |
| 65 | (2R,3S)-3-(Formylhydroxyamino)-2-(3-phenyl-1-propyl)butanoic Acid [(1S)-(1-methylcarbamoyl-1-(4-phenylcarbamoylamino)-1-butyl]amide |
| 66 | (2R,3S)-3-(Formylhydroxyamino)-2-(benzyl)hexanoic Acid [(1S)-(1-carbamoyl)-1-(3-indole)]amide |
| 67 | (2R,3S)-3-(Formylhydroxyamino)-2-(benzyl)hexanoic Acid [(1S)-(1-carbamoyl)-1-benzyl]amide |
| 68 | (2R,3S)-3-(Formylhydroxyamino)-2-(benzyl)hexanoic Acid [(1S)-(1-methylcarbamoyl)-1-benzyl]amide |

Preferred embodiments of the invention include compounds of general formula (II) where:

$R_1$ is methyl, ethyl, n-propyl, isopropyl, 4-methyl-1-pentyl, 2-thiophenesulfanylmethyl, 3-aminophenoxymethyl, 2-(3-tetrazolyl)-1-ethyl, 2-(3-pyridyl)-1-ethyl, 2-(3-furyl)-1-ethyl, 2-(2-thiazolyl)-1-ethyl, 3,3,3-trifluoro-1-propyl, 2-(4-trifluorophenyl)-1-ethyl, thiophene-3-ethynyl, 2-nitrophenoxymethyl, 3-nitrophenoxymethyl, 2-phenylsulfanylmethyl, trifluoromethyl, trichloromethyl, or vinyl;

$R_2$ is 5-methylthiophene-2-methyl, 2-furanmethyl, thiophene-2-methyl, benzothiophene-2-methyl, benzofuran-2-methyl, 4-fluorobenzyl, 3-phenyl-1-propyl, 3-phenyl-2-methyl-1-propyl, 3-(2-pyridyl)-1-propyl, 3-(thiophene-2-yl)-1-propyl, 4-phenyl-1-butyl, 3-phenyl-2-propene-1-yl, 3-(benzofuran-3-yl)-1-propyl, 3-(benzothiophene-3-yl)-1-propyl, 3-(furan-2-yl)-1-propyl, 3-(2-thiazolyl)-1-propyl, 3-(pyrimidin-2-yl)-1-propyl, 3-phenyl-2-ethyl-1-propyl, 3-(3-pyridyl)-1-propyl, 2-phenyl-1-ethyl, 3-(furan-3-yl)-1-propyl, 3-phenyl-1-butyl, 3-phenyl-2-methyl-2-propene-1-yl, 4-phenyl-3-methyl-2-butyl, 4-(3-thiophenyl)-2-butyl, benzothiophene-3-methyl, benzoxazole-2-methyl, 4-(3-furyl)-2-butyl, 3-(4-chlorophenyl)-1-propyl, 3-(4-fluorophenyl)-1-propyl, 3-(4-trifluoromethylphenyl)-1-propyl, benzyl, 5-phenyl-1-pentyl, 5-(4-chlorophenyl)-1-pentyl, 3-(4-methoxyphenyl)-1-propyl, 3-(4-methylphenyl)-1-propyl, 3-(4-biphenyl)-1-propyl, 3-(4'-fluoro-4-biphenyl)-1-propyl, 3-(4'-chloro-4-biphenyl)-1-propyl, 3-(4-phenoxyphenyl)-1-propyl, 3-(4'-chloro-4-phenoxyphenyl)-1-propyl, 3-(4'-fluoro-4-phenoxyphenyl)-1-propyl, 3-(4-thiophenoxyphenyl)-1-propyl, 3-(4'-chloro-4-thiophenoxyphenyl)-1-propyl, 3-(4'-fluoro-4-thiophenoxyphenyl)-1-propyl, 4-(4-trifluoromethylphenyl)-1-butyl, 4-(4-chlorophenyl)-1-butyl, 4-(4-fluorophenyl)-1-butyl, 3-(4-(4-morpholino)phenyl)-1-propyl, or 3-(4-(4-methylpiperazine)phenyl)-1-propyl;

$R_3$ is hydrogen;

$R_4$ is tert-butyl, 1-phenyl-1-ethyl, 4-(benzyloxycarbonylamino)-1-butyl, 2-(2-(benzyloxycarbonylamino)-1-ethylsulfanyl)-2-propyl, 3-pyridylmethyl, 4-(2-naphthylacetylamino)-1-butyl, 3-(benzyloxycarbonylamino)-1-propyl, 3-carbamoylamino-1-propyl, benzyl, 4-hydroxybenzyl, 4-chlorobenzyl, 4-fluorobenzyl, 3-(imino-(2,3,6-trimethyl-4-methoxybenzenesulfonylamino))-methylamino-1-propyl, 4-benzyloxycarbonylaminobenzyl, isopropyl, cyclohexyl, 4-cyclopentylacetylamino-1-butyl, 4-(3-methoxybenzoylamino)-1-butyl, 4-ethoxycarbonylamino-1-butyl, 2-(2-(ethoxycarbonylamino)-1-ethylsulfanyl)-2-propyl, 2-butyl, 1-methoxy-1-ethyl, 1-hydroxy-1-ethyl, isopropyl, 2-(methoxymethylaminocarbonyl)-1-ethyl, 2-(4-ethoxycarbonyl-1-piperazinecarbonyl)-1-ethyl, 2-guanidinesulfonyl-1-ethyl, 2-methyl-4-(2-pyridylcarbonylamino)-2-butyl, 2-(methyl benzylaminocarbonyl)-1-ethyl, 2-(4-morpholinecarbonyl)-1-ethyl, 2-pyridylcarbonylaminomethyl, acetylaminomethyl, 1-isobutoxy-1-ethyl, carbamoylaminomethyl, dimethylaminocarbonylmethyl, 2-dimethylaminosulfonyl-1-ethyl, 2-methanesulfanyl-2-propyl, 2-hydroxy-2-propyl, 4-(2-pyridylcarbonylamino-1-butyl, 2-(dimethylaminocarbonyl)-1-ethyl, 2-methanesulfonyl-1-ethyl, 1-(2-pyridylmethoxy)-1-ethyl, 1-benzyloxy-1-ethyl, phenyl, 2-methyl-1-propyl, 3-(imino-(2,2,5,7,8-pentamethylchroman-6-sulfonylamino) methylamino)-1-propyl, 2-phenyl-1-ethyl, 1-(3-pyridylmethoxy)-1-ethyl, 4-pyridylmethyl, 4-methoxybenzyl, 3-indolemethyl, 2-indolemethyl, 2-naphthylmethyl, 3-naphthylmethyl, or 2-phenyl-2-propyl;

$R_5$ is hydrogen; and $R_6$ is methyl, 2-(1-pyrrolidino)-1-ethyl, 2-pyridylmethyl, 3-pyridylmethyl, 4-pyridylmethyl, cyclopropyl, cyclobutyl, cyclopentyl, 2-(4-morpholino)-1-ethyl, 3-(4-morpholino)-1-propyl, 3-(4-methylpiperazine)-1-propyl, 2-(4-methylpiperazine)-1-ethyl, 2-(2-pyridyl)-1-ethyl, 2-(3-pyridyl)-1-ethyl, 2-(4-pyridyl)-1-ethyl, tetraethyleneglycolyl methyl ether, or 2,2,2-trifluoroethyl;

Other preferred embodiments of the invention include compounds of general formula (II) where $R_1$, $R_3$, and $R_5$ are as defined above; $R_2$ is 3-(thiophene-3-yl)-1-propyl, 3-(4-pyridyl)-1-propyl, or 3-(4-t-butylphenyl)-1-propyl; $R_4$ is 1-methylbenzyl, benzyl, 3-phenylcarbonylamino-1-propyl, 2,2-dimethyl-1-propyl, 3-phenylcarbamoylamino-1-propyl, 4-pyridylmethyl, 4-methoxybenzyl, 3-indolemethyl, 2-indolemethyl, 2-naphthylmethyl, 3-naphthylmethyl, or 2-phenyl-2-propyl; and $R_6$ is hydrogen, 2-(2-pyridyl)-1-ethyl, 2-(3-pyridyl)-1-ethyl, 2-(4-pyridyl)-1-ethyl, 1-(2-aminoethyl)-piperazine, 2-(4-imidazolyl)-1-ethylamine, 4-fluorobenzyl, 4-methoxybenzyl, 2,2-dimethyl-1-propyl, or tetraethyleneglycolyl methyl ether;

and a pharmaceutically acceptable salt, solvate, biohydrolyzable ester, biohydrolyzable amide, affinity reagent, or prodrug thereof.

Particularly preferred embodiments of the invention include compounds of general formula II where:

$R_1$ is methyl, ethyl, n-propyl, isopropyl, 4-methyl-1-pentyl, 2-thiophenesulfanylmethyl, 2-(3-tetrazolyl)-1-ethyl, 2-(3-pyridyl)-1-ethyl, 2-(3-furyl)-1-ethyl, 3,3,3-trifluoro-1-propyl, 2-(4-trifluorophenyl)-1-ethyl, 2-phenylsulfanylmethyl, trifluoromethyl, or trichloromethyl;

$R_2$ is 5-methylthiophene-2-methyl, 2-furanmethyl, thiophene-2-methyl, 4-fluorobenzyl, 3-phenyl-1-propyl, 3-phenyl-2-methyl-1-propyl, 3-(2-pyridyl)-1-propyl, 3-(thiophene-2-yl)-1-propyl, 4-phenyl-1-butyl, 3-phenyl-2-propene-1-yl, 3-(furan-2-yl)-1-propyl, 3-(2-thiazolyl)-1-propyl, 3-(3-pyridyl)-1-propyl, 2-phenyl-1-ethyl, 3-(furan- 3-yl)-1-propyl, benzothiophene-3-methyl, benzoxazole-2-methyl, 3-(4-chlorophenyl)-1-propyl, 3-(4-fluorophenyl)-1-propyl, 3-(4-trifluoromethylphenyl)-1-propyl, benzyl, 5-phenyl-1-pentyl, 5-(4-chlorophenyl)-1-pentyl, 3-(4-methoxyphenyl)-1-propyl, 3-(4-methylphenyl)-1-propyl, 3-(4-biphenyl)-1-propyl, 3-(4'-fluoro-4-biphenyl)-1-propyl, 3-(4'-chloro-4-biphenyl)-1-propyl, 3-(4-phenoxyphenyl)-1-propyl, 3-(4'-chloro-4-phenoxyphenyl)-1-propyl, 3-(4'-fluoro-4-phenoxyphenyl)-1-propyl, 3-(4-thiophenoxyphenyl)-1-propyl, 4-(4-trifluoromethylphenyl)-1-butyl, 4-(4-chlorophenyl)-1-butyl, 4-(4-fluorophenyl)-1-butyl, 3-(4-(4-morpholino)phenyl)-1-propyl, or 3-(4-(4-methylpiperazine)phenyl)-1-propyl;

$R_3$ is hydrogen;

$R_4$ is tert-butyl, 1-phenyl-1-ethyl, 4-(benzyloxycarbonylamino)-1-butyl, 2-(2-(benzyloxycarbonylamino)-1-ethylsulfanyl)-2-propyl, 3-pyridylmethyl, 4-(2-naphthylacetylamino)-1-butyl, 3-(benzyloxycarbonylamino)-1-propyl, 3-carbamoylamino-1-propyl, benzyl, 4-hydroxybenzyl, 4-chlorobenzyl, 4-fluorobenzyl, isopropyl, cyclohexyl, 4-cyclopentylacetylamino-1-butyl, 4-(3-methoxybenzoylamino)-1-butyl, 4-ethoxycarbonylamino-1-butyl, 2-(2-(ethoxycarbonylamino)-1-ethylsulfanyl)-2-propyl, 2-butyl, 1-methoxy-1-ethyl, 1-hydroxy-1-ethyl, isopropyl, 2-(4-ethoxycarbonyl-1-piperazinecarbonyl)-1-ethyl, 2-(methyl benzylaminocarbonyl)-1-ethyl, 2-pyridylcarbonylaminomethyl, acetylaminomethyl, 1-isobutoxy-1-ethyl, carbamoylaminomethyl, dimethylaminocarbonylmethyl, 2-dimethylaminosulfonyl-1-ethyl, 2-methanesulfanyl-2-propyl, 2-hydroxy-2-propyl, 4-(2-pyridylcarbonylamino-1-butyl, 2-(dimethylaminocarbonyl)-1-ethyl, 2-methanesulfonyl-1-ethyl, 1-(2-pyridylmethoxy)-1-ethyl, 1-benzyloxy-1-ethyl, 2-phenyl-1-ethyl, 1-(3-pyridylmethoxy)-1-ethyl, 4-pyridylmethyl, 4-methoxybenzyl, 3-indolemethyl, 2-indolemethyl, 2-naphthylmethyl, 3-naphthylmethyl, or 2-phenyl-2-propyl;

$R_5$ is hydrogen; and $R_6$ is methyl, 2-(1-pyrrolidino)-1-ethyl, 2-pyridylmethyl, 3-pyridylmethyl, 4-pyridylmethyl, cyclopropyl, cyclopentyl, 2-(4-morpholino)-1-ethyl, 3-(4-morpholino)-1-propyl, 3-(4-methylpiperazine)-1-propyl, 2-(4-methylpiperazine)-1-ethyl, 2-(2-pyridyl)-1-ethyl, 2-(3-pyridyl)-1-ethyl, 2-(4-pyridyl)-1-ethyl, tetraethyleneglycolyl methyl ether, or 2,2,2-trifluoroethyl;

Other particularly preferred embodiments of the invention include compounds of general formula (II) where $R_1$, $R_3$, and $R_5$ are as defined above; $R_2$ is benzyl, 5-phenyl-1-pentyl or 5-(4-chlorophenyl)-1-pentyl; $R_4$ is 1-methylbenzyl, benzyl, 2,2-dimethyl-1-propyl, 4-pyridylmethyl, 4-methoxybenzyl, 3-indolemethyl, 2-indolemethyl, 2-naphthylmethyl, 3-naphthylmethyl, or 2-phenyl-2-propyl; and $R_6$ is hydrogen, 2-(2-pyridyl)-1-ethyl, 2-(3-pyridyl)-1-ethyl, 2-(4-pyridyl)-1-ethyl, or tetraethyleneglycolyl methyl ether;

and a pharmaceutically acceptable salt, solvate, biohydrolyzable ester, biohydrolyzable amide, affinity reagent, or prodrug thereof More particularly preferred embodiments of the invention include compounds of general formula II where:

$R_1$ is methyl, ethyl, n-propyl, isopropyl, or 3,3,3-trifluoro-1-propyl;

$R_2$ is 3-phenyl-1-propyl, 3-(4-chlorophenyl)-1-propyl, 3-(4-fluorophenyl)-1-propyl, 3-(4-trifluoromethylphenyl)-1-propyl, or 3-(thiophene-2-yl)-1-propyl;

$R_3$ is hydrogen;

$R_4$ is tert-butyl or 1-phenyl-1-ethyl;

$R_5$ is hydrogen; and $R_6$ is methyl, 2-(1-pyrrolidino)-1-ethyl, 2-pyridylmethyl, 3-pyridylmethyl, or 4-pyridylmethyl;

and a pharmaceutically acceptable salt, solvate, biohydrolyzable ester, biohydrolyzable amide, affinity reagent, or prodrug thereof Other more particularly preferred embodiments of the invention include compounds of general formula (II) where $R_1$, $R_3$, and $R_5$ are as defined above; $R_2$ is 3-(4-methylphenyl)-1-propyl, 3-(4-phenoxyphenyl)-1-propyl, or 5-phenyl-1-pentyl; $R_4$ is benzyl, 4-fluorobenzyl, 2-butyl, cyclohexyl, or isopropyl; and $R_6$ is 2-(4-morpholino)-1-ethyl, 3-(4-morpholino)-1-propyl, tetraethyleneglycolyl methyl ether, 2-(2-pyridyl)-1-ethyl, 2-(3-pyridyl)-1-ethyl, or 2-(4-pyridyl)-1-ethyl;

and a pharmaceutically acceptable salt, solvate, biohydrolyzable ester, biohydrolyzable amide, affinity reagent, or prodrug thereof.

The compounds of the present invention are inhibitors of matrix metalloproteases, TNF converting enzyme, and TNF activity from whole cells. The compounds of the present invention may also inhibit shedding of pathologically significant cell surface protein ectodomains. The invention described herein is additionally directed to pharmaceutical compositions and methods of inhibiting matrix metalloprotease and/or TNF activity in a mammal, which methods comprise administering, to a mammal in need of inhibition of matrix metalloprotease and/or TNF activity, a therapeutically defined amount of a compound of formula (I) or (II), defined above, as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

According to a further aspect of the present invention there is provided a compound of formula (II) as defined above or a pharmaceutically acceptable salt, solvate, biohydrolyzable ester, biohydrolyzable amide, affinity reagent, or prodrug thereof for use in therapy.

Thus, the present invention provides a method of inhibiting a matrix metalloprotease, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit a matrix metalloprotease. A matrix metalloprotease-inhibiting amount can be an amount that reduces or inhibits a matrix metalloprotease activity in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting a matrix metalloprotease.

The present invention further provides a method of inhibiting the intracellular release of tumor necrosis factor alpha, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit cellular release of mature tumor necrosis factor. An amount sufficient to inhibit cellular release of mature tumor necrosis factor can be an amount that reduces or inhibits cellular release of mature tumor necrosis factor in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting the intracellular release of tumor necrosis factor alpha.

Also provided is a method of inhibition of shedding of cell surface protein ectodomains, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit shedding of cell surface protein ectodomains. An amount sufficient to inhibit shedding of cell surface protein ectodomains can be an amount that reduces or inhibits shedding of one or more cell surface protein ectodomains, such as L-selectin, fibronectin, thyrotropin stimulating hormone receptor, transforming growth factor alpha precursor, low density lipoprotein receptor, beta amyloid precursor protein, interleukin-6 receptor alpha subunit, Fas ligand, CD40 ligand, epidermal growth factor receptor, macrophage colony stimulating factor, interleukin-1 receptor type II, CD30, and tumor necrosis factor receptors type I and II, in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting the shedding of cell surface protein ectodomains.

Also provided is a method of inhibiting CD23 proteolysis, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit CD23 proteolysis. An amount sufficient to inhibit CD23 proteolysis can be an amount that reduces or inhibits CD23 proteolysis in the subject.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting CD23 proteolysis.

Additionally provided is a pharmaceutical composition comprising a pharmaceutically acceptable carrier and a pharmacologically effective amount of a compound of the present invention sufficient to decrease, or inhibit, a malignant growth.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for inhibiting the growth of tumor metastases.

Further, the present invention provides a pharmaceutical composition comprising a pharmaceutically acceptable carrier and a pharmacologically effective amount of a compound of the present invention sufficient to treat arthritis. Such an amount can be an amount that relieves, i.e., reduces or eliminates, one or more physiologic characteristic of arthritis According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for treating arthritis.

Also provided is a pharmaceutical composition comprising a pharmaceutically acceptable carrier and a pharmacologically effective amount of a compound of the present invention sufficient to treat diabetes. Such an amount can be an amount that reduces or eliminates one or more of the complications associated with diabetes.

According to a further aspect of the present invention there is also provided the use of a compound of formula (II) as defined above or a pharmaceutically acceptable salt, solvate, biohydrolyzable ester, biohydrolyzable amide, affinity reagent, or prodrug thereof in the preparation of a medicament for treating diabetes.

Additionally, the present invention contemplates treating any of these diseases/conditions in a subject by administering to the subject the recited pharmaceutical composition.

The compounds of the present invention can be administered to any mammal in need of inhibition of matrix metalloprotease activity, CD23 proteolysis, shedding of cell surface protein ectodomains and/or TNF activity. Such mammals can include, for example, horses, cows, sheep, pigs, mice, dogs, cats, primates such as chimpanzees, gorillas, rhesus monkeys, and, most preferably humans.

Certain examples of the invention also are orally bioavailable in animals and possess oral activity in animal models of disease.

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate.

Other salts which are not pharmaceutically acceptable may be useful in the preparation of compounds of formula (I) or (II) and these form a further aspect of the invention.

Also included within the scope of the invention are the individual enantiomers of the compounds represented by formula (I) or (II) above as well as any wholly or partially racemic mixtures thereof. The present invention also covers the individual enantiomers of the compounds represented by formula above as mixtures with diastereoisomers thereof in which one or more of the three stereocenters are inverted.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, methyl, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino hi optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, "cycloalkyl" refers to a alicyclic hydrocarbon group with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heterocyclic" or the term "heterocyclyl" refers to a three to twelve-membered heterocyclic ring having one or more degrees of unsaturation containing one or more heteroatomic substitutions selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, piperazine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine- 2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfenyl" refers to the group $R_aS(O)$—, where $R_a$ is alkyl.

As used herein, the term "alkenylsulfenyl" refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (I) or (II)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of general formula (I) or (II)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) or (II) in plasma. Many examples of such are known in the art and include by way of example lower alkyl esters, lower acyloxyalkyl esters, lower alkoxyacyloxyalkyl esters, alkoxyacyloxy esters, alkyl acylamino alkyl esters, and choline esters. An example of such a biohydrolyzable ester applied to the general formula (II) is illustrated below in general formula (III).

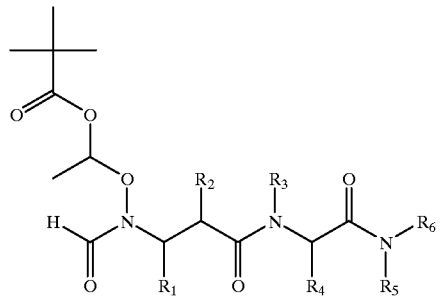

(III)

As used herein, the term "biohydrolyzable amide" is an amide of a drug substance (in this invention, a compound of general formula (I) or (II)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) or (II) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) or (II): for example, the lactam formed by a carboxylic group in $R_2$ and an amine in $R_4$, and b) compounds which may be oxidized or reduced biologically at a given functional group to yield drug substances of formula (I) or (II). Examples of these functional groups include, but are not limited to, 1,4-dihydropyridine, N-alkylcarbonyl-1, 4-dihydropyridine, 1,4-cyclohexadiene, tert-butyl, and the like.

As used herein, the term "affinity reagent" is a group attached to the compound of formula (I) or (II) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or (II) or linked with a spacer of one to 50 atoms selected from the group consisting of C, H, O, N, S, or P in any combination. An example of an affinity reagent according to a) above would be fluorescein, either directly attached to (I) or (II) or linked with a spacer of one to 50 atoms selected from the group consisting of C, H, O, N, S, or P in any combination.

The term "pharmacologically effective amount" shall mean that amount of a drug or pharmaceutical agent that will elicit the biological or medical response of a tissue, system, animal or human that is being sought by a researcher or clinician. This amount can be a therapeutically effective amount.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent=O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —C(O)$NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —S(O)$_2$—.

The compounds of formula (I) and (II) can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:
g=grams
mg=milligrams
L=liters
mL=milliliters
psi=pounds per square inch
M=molar
N=normal
mM=millimolar
i.v.=intravenous
p.o.=per oral
s.c.=subcutaneous
Hz=hertz
mol=moles
mmol=millimoles
mbar=millibar
rt=room temperature
min=minutes
h=hours
mp=melting point
TLC=thin layer chromatography
$R_f$=relative TLC mobility
MS=mass spectrometry
NMR=nuclear magnetic resonance spectroscopy
APCI=atmospheric pressure chemical ionization
ESI=electrospray ionization
m/z=mass to charge ratio
$t_r$=retention time
ether=diethyl ether
MeOH=methanol
EtOAc=ethyl acetate
TEA=triethylamine
DIEA=diisopropylethylamine
BOP=(1-benzotriazolyloxy)tris(dimethylamino) phosphonium hexafluorophosphate
THF=tetrahydrofuran
DMF=N,N-dimethylformamide
DMSO=dimethylsulfoxide
LAH=lithium aluminum hydride
TFA=trifluoroacetic acid
EDC=1-ethyl-3-(3-dimethylaminopropyl)-carbodiimide hydrochloride
HOBt=1-hydroxybenzotriazole
LDA=lithium diisopropylamide
THP=tetrahydropyranyl
NMM=N-methylmorpholine, 4-methylmorpholine
HMPA=hexamethylphosphoric triamide
DMPU=1,3-dimethypropylene urea
hr=hours
d=days
min=minutes
ppm parts per million
kD=kiloDalton
LPS=lipopolysaccharide
PMA=phorbol myristate acetate
SPA=scintillation proximity assay
EDTA=ethylenediamine tetraacetic acid
FBS=fetal bovine serum
PBS=phosphate buffered saline solution
ELISA=enzyme-linked immunosorbent assay Several of the following examples represent pairs of stereoisomers which were separated as diastereoisomers but were not identified therein. Determination and/or preparation of the R and S isomers could advantageously be approached by stereoselective chemical methods (see, e.g., "Advanced Organic Chemistry", Carey and Sundberg, 3rd edition, Plenum Press, 1990, 596), by analytical methods such as X-ray crystallography, or by determination of biological activity and subsequent correlation to biologically active compounds of known stereochemistry.

GENERAL REACTION SCHEMES

Compounds of the invention may be prepared by methods known in the art, where such a method is shown in reaction Scheme 1.

Reaction Scheme 1

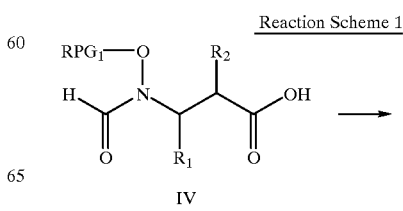

IV

-continued

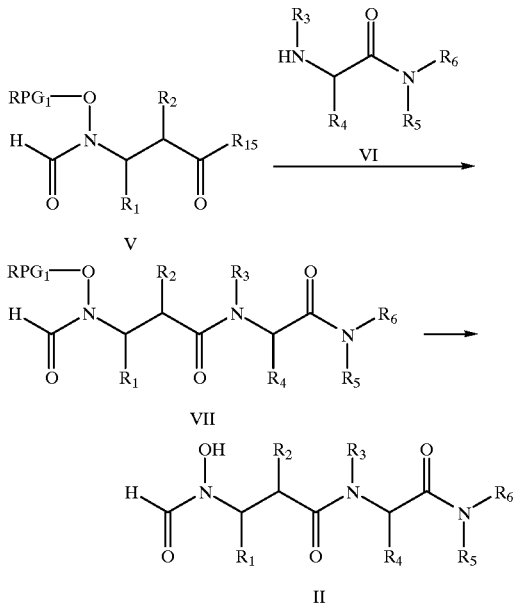

$R_1$, $R_2$, $R_3$, $R_4$, $R_5$, and $R_6$ are as defined as for formula (II).

$RPG_1$ is selected from the group consisting of benzyl or 2-tetrahydropyranyl.

$R_{15}$ is chosen from the group consisting of hydroxyl, $O-C_6F_5$, or halogen.

When $R_{15}$ is hydroxyl, the conversion of (V) to (VII) involves methods known in peptide chemistry; for example, the reaction may be conducted using HOBt in combination with a dehydrating agent such as dicyclohexylcarbodiimide in a suitable solvent, such as DMF. When $R_{15}$ is $O-C_6F_5$, the conversion of (IV) to (V) is conducted by treating (IV) in a suitable solvent such as dichloromethane with pentafluorophenyl trifluoroacetate in the presence of pyridine, or with EDC and pentafluorophenol in a suitable solvent such as dichloromethane. The displacement reaction to produce (VII) is carried out in the presence of a suitable solvent such as dioxane, THF, dichloromethane, or DMF, at a temperature of 0° C. to 140° C. The reaction is effected in the presence of an organic base such as NMM or triethylamine. The removal of the $RPG_1$ group where $RPG_1$ is benzyl may be achieved by hydrogenation of (VII) with palladium on barium sulfate in a suitable solvent such as methanol or THF, or, where $RPG_1$ is 2-tetrahydropyranyl, by hydrolysis with aqueous acetic acid at a temperature of 20° C. to 100° C.

Reaction Scheme 2 depicts the synthesis of a compound of formula (IV).

Reaction Scheme 2

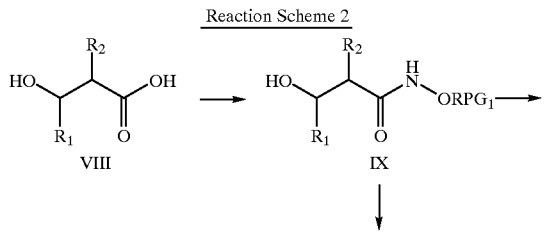

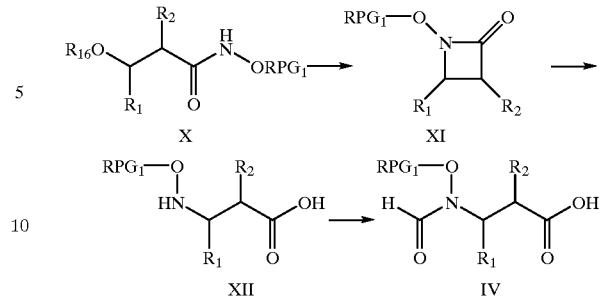

$R_1$ and $R_2$ are as defined for formula (II).

$R_{16}O$ is a nucleofugal group such as methanesulfonate, trifluoromethanesulfonate, or p-toluenesulfonate.

$RPG_1$ is selected from the group consisting of benzyl or 2-tetrahydropyranyl.

The acid of formula (VIII) may be converted to the alcohol of formula (IX) by treatment with HOBt, O-benzylhydroxylamine hydrochloride or 2-tetrahydropyranyloxyamine, NMM, and a carbodiimide reagent such as EDC in a suitable solvent such as DMF. The alcohol of formula (IX) may be converted to (X) by treatment with methanesulfonyl chloride, p-toluenesulfonyl chloride, or trifluoromethanesulfonic anhydride and pyridine in a suitable solvent such as dichloromethane. The conversion of (X) to (XI) may be conducted by treatment with potassium carbonate in a suitable solvent such as acetone or 2-butanone, at temperature of 20° C. to 90° C. Alternatively, (IX) may be converted directly to (XI) by treatment with triphenylphosphine and diethyl azodicarboxylate or another azodicarbonyl diester or diamide in a suitable solvent such as THF at a temperature of −78° C. to 50° C. The compound of formula (XI) may be converted to (XII) by treatment with an inorganic base such as sodium hydroxide in water or water in combination with a water soluble organic cosolvent such as methanol or dioxane, followed by acidification with an acidic solution such as aqueous citric acid or aqueous sodium bisulfate. The compound of formula (XII) may be converted to (IV) by treatment with acetic anhydride and formic acid or by treatment with formic acetic anhydride in pyridine in the presence or absence of a suitable cosolvent such as dichloromethane.

An alternative route of preparation of compounds of formula (IX) is depicted in reaction Scheme 3.

Reaction Scheme 3

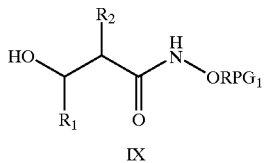

IX

R₁ and R₂ are as defined as for formula (II).

RPG₁ is selected from the group consisting of benzyl or 2-tetrahydropyranyl.

R₁₇ is chosen from the group consisting of lower alkoxy or oxazolidinon-1-yl, where the 4 and positions of an oxazolidinon-1-yl group may be substituted with a lower alkyl, aryl, or lower alkylaryl group and where such an oxazolidinon-1-yl substituent may exist as a single stereoisomer or as a mixture of stereoisomers.

A carbonyl compound of formula (XIII), where R₁₇ is an alkoxy group such as methoxy or tert-butoxy, may be treated with a strong base such as LDA in a solvent such as THF at a temperature of from −78° C. to 0° C., followed by treatment with the aldehyde (XIV) to provide (XV). Where R₁₇ is an oxazolidinon-1-yl substituent, treatment of (XIII) with a Lewis acid such as di(n-butyl)boron trifluoromethanesulfonate in the presence of N,N-diisopropylethylamine in a suitable solvent such as dichloromethane at a temperature of 0° C., followed by addition of the aldehyde (XIV) provides (XV). Treatment of (XV) with aqueous base in the presence or absence of hydrogen peroxide affords (VIII) upon acidification. The acid (VIII) may be converted directly to (IX) as in reaction Scheme 2, or may be treated with a dehydrating agent such a p-toluenesulfonyl chloride in pyridine or with triphenylphosphine and diethyl azodicarboxylate in a suitable solvent such as THF, to afford the lactone (XVI). Treatment of the lactone (XVI) with H₂NO—RPG₁ in the presence of a Lewis acid such as trimethylaluminum in a suitable solvent such as toluene affords the alcohol (IX).

Reaction Scheme 4 depicts the preparation of compounds of general formula (VIII).

Reaction Scheme 4

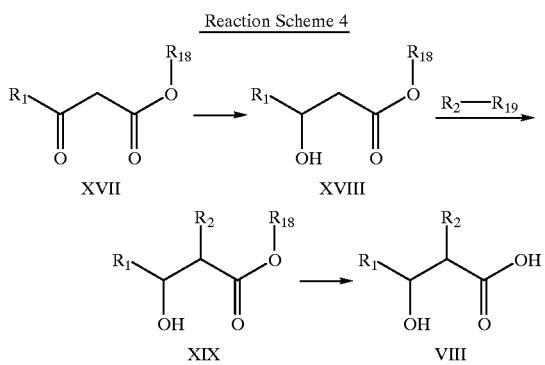

R₁ and R₂ are as defined as for formula (II).

RPG₁ is selected from the group consisting of benzyl or 2-tetrahydropyranyl.

R₁₈ is selected from the group consisting of lower alkyl or benzyl.

R₁₉ is selected from the group consisting of chloride, bromide, iodide, or trifluoromethanesulfonate.

The ketoester of general formula (XVII) may be formed by treating 2,2-dimethyl-1,3-dioxane-4,6-dione with an appropriate acid chloride R₁COCl in the presence of base, an alcohol solvent, and heat.

The ketoester of general formula (XVII) may be reduced with a reducing agent such as sodium borohydride to afford the hydroxyester (XVIII). Alternately, reduction of (XVII) with a chiral catalyst or chiral ligand in the presence of a reducing agent such as hydrogen or a metal hydride such as borane or lithium aluminum hydride may be employed to afford (XVIII) with chiral induction at the newly formed center. The alcohol (XVIII) may be converted to (XIX) by treatment with a strong base such as LDA in a suitable solvent such as THF, followed by the addition of R₂–R₁₉ in the presence or absence of a cosolvent such as DMPU. Removal of the ester group by hydrolysis with aqueous hydroxide ion or, in the case where R₁₈ is tert-butyl, by treatment with a strong acid such as TFA, affords (VIII).

An alternate preparation of compounds of general formula (XI) and a preparation of compounds of general formulae (XXII) and (IV) is depicted in reaction Scheme 5.

Reaction Scheme 5

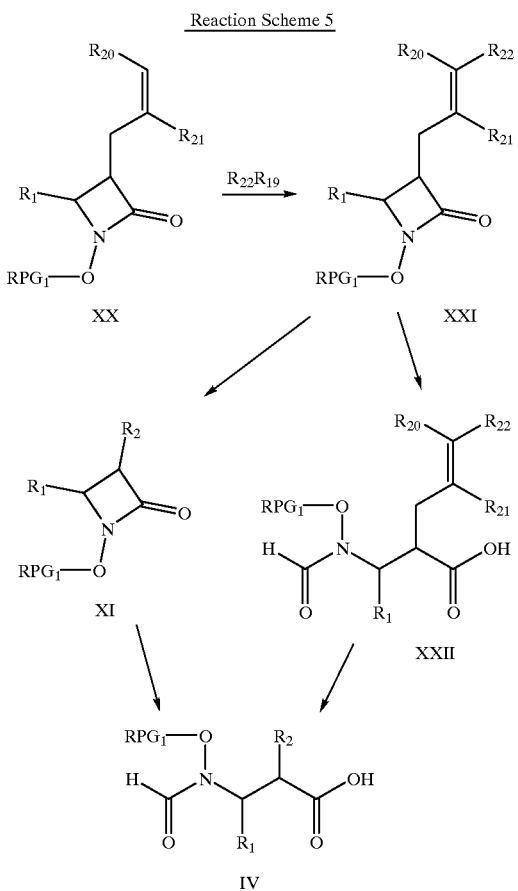

R₁ and R₂ are as defined as for formula (II).

R₂₂ is selected from the group consisting of aryl or heteroaryl.

R₁₉ is selected from the group consisting of chloride, bromide, iodide, or trifluoromethanesulfonate.

RPG₁ is selected from the group consisting of benzyl or 2-tetrahydropyranyl.

R₂₀ and R₂₁ may be, independently, alkyl, alkenyl, alkynyl, cycloalkyl, cycloalkenyl, heterocyclyl, aryl, heteroaryl, or hydrogen, where alkyl, alkenyl, and alkynyl substituents may contain one or more O, S, SO, or SO₂ substituents.

The lactam of general formula (XX) may be treated with a metal catalyst such as tetrakis(triphenylphosphine) palladium or palladium chloride and $R_{22}$–$R_{19}$ in a solvent such as acetonitrile at a temperature of from 20° C. to 200° C. to afford (XXI). Reduction of the olefinic group in (XXI) with hydrogen and a metal catalyst such as palladium on carbon and conversion of the lactam (XI) to the acid (IV) proceeds as outlined in reaction Scheme 2. Alternately, the olefin in compounds of general formula (XXI) may be left in place and manipulation of the lactam (XXI) carried out as described in reaction Scheme 2 to afford (XXII). Acid (XXII) may be converted to (IV) as described in reaction Scheme 2 with or without reduction of the olefin in (XXII), as appropriate.

The preparation of compounds of general formula (VIII) and (XI) is shown in reaction Scheme 6.

Reaction Scheme 6

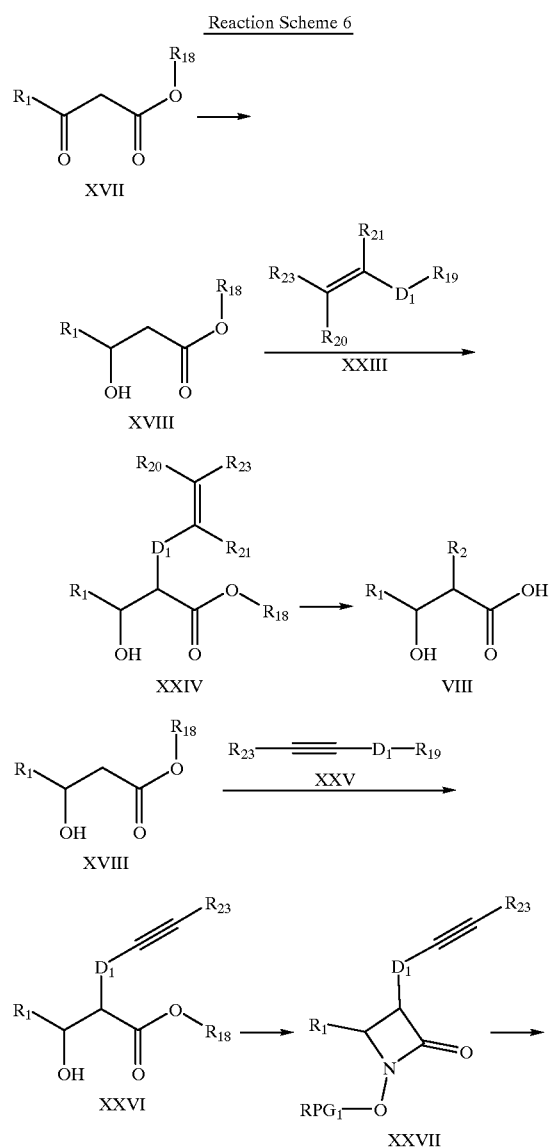

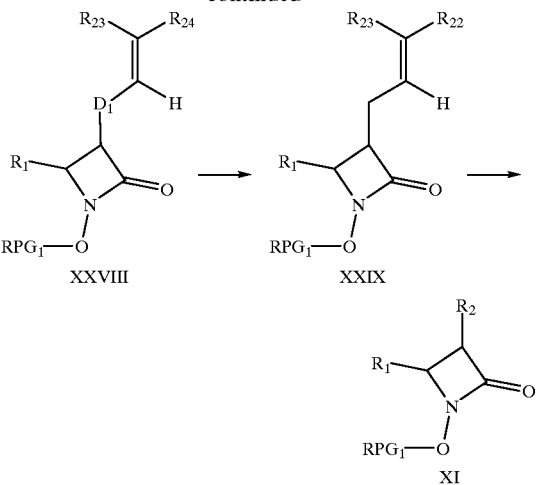

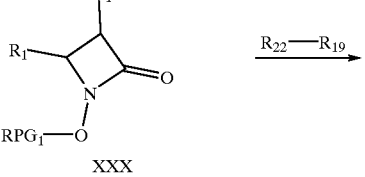

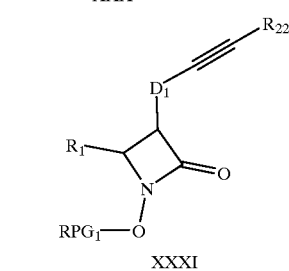

$R_1$, $R_2$, and $D_1$ are as defined as for formula (II).

$RPG_1$ is selected from the group consisting of benzyl or 2-tetrahydropyranyl.

$R_{18}$ is selected from the group consisting of lower alkyl or benzyl.

$R_{19}$ is selected from the group consisting of chloride, bromide, iodide, or trifluoromethanesulfonate.

$R_{20}$, $R_{21}$ and $R_{23}$ may be, independently, alkyl, alkenyl, alkynyl, cycloalkyl, cycloalkenyl, heterocyclyl, aryl, heteroaryl, or hydrogen, where alkyl, alkenyl, and alkynyl substituents may contain one or more O, S, SO, or $SO_2$ substituents.

$R_{22}$ is aryl or heteroaryl.

$R_{24}$ is a trialkylstannyl group.

The alcohol (XVIII), prepared from (XVII) as outlined in reaction Scheme 4, may be converted to (XXIV) by treatment with a strong base such as LDA in a suitable solvent such as THF, followed by the addition of (XXIII), in the presence or absence of a cosolvent such as DMPU. The alkene (XXIV) may be converted to the acid (VIII) as described in reaction Scheme 2. The alcohol (XVIII) may be converted to (XXVI) by treatment with a strong base such as LDA in a suitable solvent such as THF, followed by the addition of (XXV), in the presence or absence of a cosolvent such as DMPU. Conversion of (XXVI) to (XXVII) proceeds as described in reaction Scheme 2. The alkyne (XXVII) may be treated with $R_{24}$—H and a radical initiator such as azobis(isobutyronitrile) in a solvent such as toluene to afford (XXVIII). The alkenyltin compound (XXVIII) may be treated with a catalyst such as tetrakis(triphenylphosphine) palladium and $R_{22}$–$R_{19}$ in a solvent such as DMF at a temperature of from 20° C. to 180° C. to provide (XXIX). The alkene (XXIX) may be transformed to the lactam (XI) by operations known in the art of organic chemistry such as catalytic hydrogenation. The alkyne (XXX) (where $R_{23}$=H) may be treated with $R_{22}$–$R_{19}$ in the presence of tetrakis (triphenylphosphine)palladium and cuprous chloride in a solvent such as DMF or acetonitrile at a temperature of 60° C. to 120° C. to afford (XXXI). Compound (XXXI) may be converted if desired to (XI) by operations known in the art of organic chemistry such as catalytic hydrogenation.

The preparation of compounds of general formula (VI) is shown in reaction Scheme 7.

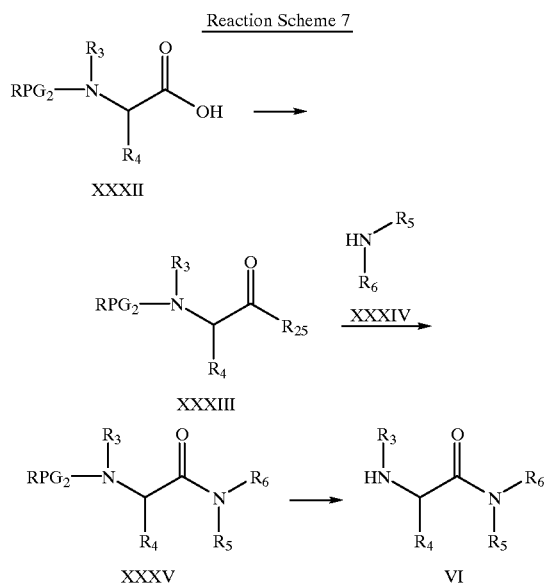

$R_3$, $R_4$, $R_5$, and $R_6$ are as defined for general formula (II).

$RPG_2$ is selected from the group consisting of tert-butoxycarbonyl, allyloxycarbonyl, or benzyloxycarbonyl.

$R_{25}$ is selected from the group consisting of 1-benzotriazolyloxy, or bromine.

The acid of formula (XXXII) may be converted in situ to (XXXIII), where $R_{25}$ is bromine, by treatment with bromo-tris(pyrrolidino)phosphonium hexafluorophosphate in a suitable solvent such as DMF in the presence of an organic base such as N,N-diisopropylethylamine. The acid of formula (XXXII) may be converted in situ to (XXXIII), where $R_{25}$ is benzotriazolyloxy, by treatment with BOP in a suitable solvent such as DMF in the presence of an organic base such as NMM. Addition of the amine (XXXIV) in the displacement step in the presence of a suitable solvent such as DMF and an organic base such as N,N-diisopropylethylamine affords the amide (XXXV). Alternatively, the intermediate of formula (XXXII) may be treated with carbonyldiimidazole in a solvent such as dichloromethane, followed by treatment with the amine (XXXIV) to afford (XXXV). Alternatively, the intermediate of formula (XXXII) may be treated with HOBt, the amine (XXXIV), an organic base such as NMM, and a carbodiimide reagent such as EDC in a suitable solvent such as DMF, at a temperature of 0° C. to 80° C. to provide (XXXV). The compound of formula (XXXV) may be converted to (VI) by deprotection, conditions being particular to the nature of $RPG_2$. For example, where $RPG_2$ is tert-butoxycarbonyl, conversion of (XXXV) to (VI) may be accomplished by treatment of (XXXV) with TFA in the presence or absence of a suitable solvent such as dichloromethane, at a temperature of 0° C. to 50° C.

PHARMACEUTICAL FORMULATION AND DOSES

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 2000 mg/kg of body weight per day, and particularly 1 to 1000 mg/kg of body weight per day. Oral dosage units will generally be administered in the range of from 1 to about 250 mg and more preferably from about 25 to 250 mg. The daily dosage for a 70 kg mammal will generally be in the range of about 10 mg to 5 grams of a compound of formula I or II.

While the dosage to be administered is based on the usual conditions such as the physical condition of the patient, age, body weight, past medical history, route of administrations, severity of the conditions and the like, it is generally preferred for oral administration to be used to administer to a human. In some cases, a lower dose is sufficient and, in some cases, a higher dose or more doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular, intrathecal, intraarterial or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher esters, myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

EXAMPLES

The following examples are illustrative embodiments of the invention, not limiting the scope of the invention in any way. Reagents are commercially available or are prepared according to procedures in the literature.

EXAMPLE 1

(2R,3S)-3-(Formylhydroxyamino)-2-(3-phenyl-1-propyl)butanoic Acid [(1S)-2,2-Dimethyl-1-(methylcarbamoyl)-1-propyl]amide

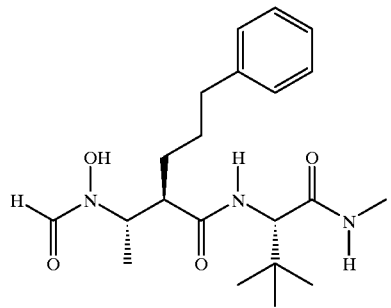

EXAMPLE 1a

Methyl (2R,3R)-2-[(2E)-3-Phenyl-2-propen-1-yl]-3-hydroxybutanoate

To a solution of diisopropylamine (47.1 g, 466.1 mmol) in THF (500 mL) cooled to −50° C. is added n-butyllithium (466.1 mmol, 2.5M in hexanes) and the resulting solution is stirred at −50° C. for 0.5 h. The reaction mixture is cooled to −78° C. followed by slow addition of methyl (3R)-3-hydroxybutanoate (25 g, 211.9 mmol). After 0.5 h a solution of cinnamyl bromide (45.9 g, 233.0 mmol) in HMPA (10 mL) is added and the reaction mixture is allowed to warm to 0° C. and stirred for 16 h. The reaction mixture is quenched by addition 30 mL of saturated aqueous ammonium chloride solution, is poured into 400 mL of 1 M hydrochloric acid, and is extracted with two 500 mL portions of ethyl acetate. The combined organic layers are dried over magnesium sulfate, concentrated in vacuo, and purified by silica gel chromatography (elution with 25% ethyl acetate-hexanes) to afford methyl (2R,3R)-2-[(2E)-3-phenyl-2-propen-1-yl]-3-hydroxybutanoate as a yellow oil (42 g, 85% yield).

$^1$H NMR (400 MHz, CDCl$_3$) δ7.32–7.18 (m, 5H), 6.44 (d, 1H), 6.13 (m, 1H), 3.98 (m, 1H), 3.69 (s, 3H), 2.56 (m, 4H), 1.25 (t, 3H) ppm.

ESI-MS m/z 257.2 (M+Na)$^+$.

EXAMPLE 1b

Methyl (2R,3R)-2-(3-Phenyl-1-propyl)-3-hydroxybutanoate

A solution of methyl (2R,3R)-2-[(2E)-3-phenyl-2-propen-1-yl]-3-hydroxybutanoate (42.0 g, 179.5 mmol) in 400 mL of methanol is treated with 400 mg of 10% palladium on carbon. The resulting suspension is repeatedly evacuated and purged with a hydrogen balloon, then stirred under 1 atmosphere pressure of hydrogen gas for 16 h. The catalyst is filtered and the filtrate is concentrated in vacuo to provide methyl (2R,3R)-2-(3-phenyl-1-propyl)-3-hydroxybutanoate as an oil (42.2 g, 100% yield).

$^1$H NMR (400 MHz, CDCl$_3$) δ7.25 (m, 2H), 7.17 (m, 3H), 3.88 (m, 1H), 3.69 (s, 3H), 2.61 (m, 2H), 2.42 (m, 2H), 1.72 (m, 1H), 1.62 (m, 3H), 1.19 (d, 3H) ppm.

ESI-MS m/z 259.2 (M+Na)$^+$.

EXAMPLE 1c (2R,3R)-2-(3-Phenyl-1-propyl)-3-hydroxybutanoic Acid

To a solution of methyl (2R,3R)-2-(3-phenyl-1-propyl)-3-hydroxybutanoate (42.2 g, 179.5 mmol) in THF-methanol (3:1, 535 mL) is added 2 M aqueous sodium hydroxide solution (135 mL, 269.3 mmol). The solution is stirred at 23° C. for 20 h, then concentrated and extracted with hexanes (100 mL). The aqueous layer is acidified to pH=3 with saturated aqueous sodium bisulfate and is extracted with two 500 mL portions of ethyl acetate. The combined organic layers are dried over anhydrous magnesium sulfate and concentrated under reduced pressure to provide (2R,3R)-2-(3-phenyl-1-propyl)-3-hydroxybutanoic acid as an oil (33.0 g, 83% yield).

$^1$H NMR (400 MHz, CDCl$_3$) δ7.28 (m, 2H), 7.16 (m, 3H), 3.93 (m, 1H), 2.63 (m, 2H), 2.43 (m, 1H), 1.69 (m, 4H), 1.26 (d, 3H) ppm.

ESI-MS m/z 221.3 (M−H)$^-$.

EXAMPLE 1d (2R,3R)-2-(3-Phenyl-1-propyl)-3-hydroxybutanoic Acid 2 Tetrahydropyranyloxyamide To a solution of (2R,3R)-2-(3-phenyl-1-propyl)-3-hydroxybutanoic acid (33.0 g, 148.7 mmol) in dichloromethane (300 mL) is added 2-tetrahydropyranyloxyamine (18.3 g, 156.1 mmol) and EDC (31.2 g, 163.5 mmol). The resulting solution is stirred at 23° C. for 16 h. then diluted with dichloromethane (500 mL) and washed sequentially with 1 M hydrochloric acid, saturated aqueous sodium bicarbonate solution, and saturated aqueous sodium chloride solution. The reaction mixture is dried over anhydrous magnesium sulfate and concentrated under reduced pressure to provide (2R,3R)-2-(3-phenyl-1-propyl)-3-hydroxybutanoic acid 2-tetrahydropyranyloxyamide as a foam (47.8 g, 100% yield).

¹H NMR (400 MHz, CDCl₃) δ8.66 (bs, 1H), 7.25 (m, 2H), 7.17 (m, 3H), 4.94 (m, 1H), 3.89 (m, 2H), 3.61 (m, 1H), 2.62 (t, 2H), 1.93 (m, 1H), 1.78 (m, 4H), 1.66 (m, 6H), 1.23 (d, 3H)

ESI-MS m/z 320.4 (M−H)⁻.

EXAMPLE 1e (3R,4S)-1-(2-Tetrahydropyranyloxy)-3-(3-phenyl-1-propyl)-4-methylazetidin-2-one To a solution of (2R,3R)-2-(3-phenyl-1-propyl)-3-hydroxybutanoic acid 2-tetrahydropyranyloxyamide (47.8 g, 148.7 mmol) in 150 mL of dichloromethane at 0° C. is added pyridine (64 mL) and methanesulfonyl chloride (20.4 g, 178.4 mmol). The resulting solution is allowed to warm to 23° C. and is stirred at 23° C. for 14 h, concentrated in vacuo, and diluted with dichloromethane (500 mL). The organic layer is washed with 1 M hydrochloric acid, saturated aqueous sodium chloride solution, dried over anhydrous magnesium sulfate, and concentrated to provide the desired methanesulfonate intermediate.

A suspension of potassium carbonate (61.5 g) in acetone (500 mL) is heated to reflux for 1 h. A solution of the above methanesulfonate in acetone (1000 mL) is added and the resulting suspension is heated at reflux for 28 h. The mixture is allowed to cool to 25° C. and is filtered, concentrated under reduced pressure, and purified by silica gel chromatography (elution with 3:1 hexanes-ethyl acetate) to provide (3R,4S)-1-(2-tetrahydropyranyloxy)-3-(3-phenyl-1-propyl)-4-methylazetidin-2-one as an oil (34.0 g, 75% yield).

¹H NMR (400 MHz, CDCl₃) δ7.25 (m, 2H), 7.17 (m, 3H), 5.13 (m, 0.5H), 4.99 (m, 0.5H), 4.15–3.98 (m, 2H), 3.64 (m, 1H), 2.93 (m, 1H), 2.67 (m, 2H), 1.89–1.51 (m, 10H), 1.28 (d, 1.5H), 1.26(d, 1.5H) ppm.

ESI-MS m/z 326.4 (M+Na)⁺.

EXAMPLE 1f (2R,3S)-2-(3-Phenyl-1-propyl)-3-(2-tetrahydropyranyloxyamino)butanoic Acid To a solution of (3R,4S)-1-(2-tetrahydropyranyloxy)-3-(3-phenyl-1-propyl)-4-methylazetidin-2-one (20.5 g, 67.6 mmol) in dioxane (220 mL) is added 1 M aqueous sodium hydroxide (102 mL). The solution is stirred at 23° C. for 20 h, then extracted with hexanes (200 mL). The aqueous layer is acidified to pH=3 with saturated aqueous sodium bisulfate solution, and is extracted with two 300 mL portions of ethyl acetate. The combined organics are washed with saturated aqueous sodium chloride, dried over anhydrous magnesium sulfate, and concentrated under reduced pressure to provide (2R,3S)-2-(3-phenyl-1-propyl)-3-(2-tetrahydropyranyloxyamino)butanoic acid as an oil (21.5 g, 99% yield).

¹H NMR (400 MHz, CDCl₃) δ7.28 (m, 2H), 7.18 (m, 3H), 4.84 (m, 0.5H), 4.70 (m, 0.5H), 3.96 (m, 0.5H), 3.89 (m, 0.5H), 3.56 (m, 1H), 3.34 (m, 0.5H), 3.24 (m, 0.5H), 2.97 (m, 0.5H), 2.81 (m, 0.5H), 2.65 (m, 2H), 1.96–1.45 (m, 10H), 1.31 (m, 1H), 1.06 (d, 1.5 H), 0.99 (d, 1.5 H) ppm.

ESI-MS m/z 344.3 (M+H)⁺.

EXAMPLE 1g (2R,3S)-2-(3-Phenyl-1-propyl)-3-(formyl-2-tetrahydropyranyloxyamino)butanoic Acid To a solution of (2R,3S)-2-(3-phenyl-1-propyl)-3-(2-tetrahydropyranyloxyamino)butanoic acid (21.4 g, 66.7 mmol) in pyridine (100 mL) at 0° C. is added formic acetic anhydride (30 mL). The resulting solution is allowed to warm to 25° C., stirred for 6 h, and then concentrated to dryness under reduced pressure. The resulting gum is dissolved in ethyl acetate (300 mL) and washed sequentially with 1 M hydrochloric acid (200 mL) and saturated aqueous sodium chloride solution. The organic layer is dried over anhydrous magnesium sulfate and concentrated under reduced pressure to provide (2R,3S)-2-(3-Phenyl-1-propyl)-3-(formyl-2-tetrahydropyranyloxyamino)butanoic acid as an oil (18.9 g, 81% yield).

ESI-MS m/z 372.3 (M+Na)⁺.
ESI-MS m/z 348.4 (M−H)⁻.

EXAMPLE 1h (2S)-2-tert-butoxycarbonylamino-3,3-dimethylbutanoic Acid Methylamide To a solution of (2S)-2-tert-butoxycarbonylamino-3,3-dimethylbutanoic acid (120 g, 519 mmol) in dichloromethane (800 mL) is added 1,1-carbonyldiimidazole (88.4 g, 545 mmol). The resulting solution is stirred at 25° C. for 1 h and methylamine hydrochloride (52.5 g, 779 mmol) and triethylamine (157.3 g, 1557 mmol) are added and the reaction is stirred for an additional 18 h. The mixture is diluted with dichloromethane (600 mL) and washed with 1 M hydrochloric acid and saturated aqueous sodium chloride. The organic layer is dried over anhydrous magnesium sulfate and concentrated in vacuo to provide (2S)-2-tert-butoxycarbonylamino-3,3-dimethylbutanoic acid methylamide as a white solid (126 g, 100% yield).

¹H NMR (400 MHz, CDCl₃) δ5.81 (bs, 1H), 5.30 (m, 1H), 3.80 (d, 1H), 2.81 (d, 3H), 1.43 (s, 9H), 0.99 (s, 9H) ppm.

ESI-MS m/z 245.4 (M+H)⁺.

EXAMPLE 1i (2S)-2-Amino-3,3-dimethylbutanoic Acid Methylamide

To a solution of (2S)-2-tert-butoxycarbonylamino-3,3-dimethylbutanoic acid methylamide (126 g, 519 mmol) in dichloromethane (320 mL) cooled at 0° C. is added trifluoroacetic acid (320 mL). The resulting solution is allowed to warm to 25° C. and is stirred for 18 h. The reaction mixture is concentrated, brought to pH=10 with 2 M sodium hydroxide, and extracted with 4:1 dichloromethane/isopropanol (1000 mL). The organic layer is washed with saturated aqueous sodium chloride, dried over anhydrous magnesium sulfate and concentrated under reduced pressure to provide (2S)-2-Amino-3,3-dimethylbutanoic acid methylamide (40.5 g, 79% yield) as a white solid.

¹H NMR (400 MHz, CDCl₃) δ6.69 (bs, 1H), 3.10 (s, 1H), 2.82 (d, 3H), 1.50 (bs, 2H), 0.99 (s, 9H) ppm.

ESI-MS m/z 145.2 (M+H)⁺.

EXAMPLE 1j (2R,3S)-3-(Formyl-2-tetrahydropyranyloxyamino)-2-(3-phenyl 1-propyl)butanoic Acid [(1S)-2,2-Dimethyl-1-(methylcarbamoyl)-1-propyl]amide To a solution of(2R,3S)-2-(3-phenyl-1-propyl)-3-(formyl-2-tetrahydropyranyloxyamino)butanoic acid (5.5 g, 15.76 mmol) in DMF (20 mL) is added BOP reagent (7.66 g, 17.34 mmol), HOBt (2.34 g, 17.34 mmol), and NMM (4.78 g, 47.28 mmol). After 30 min, addition of (2S)-2-Amino-3,3-dimethylbutanoic acid methylamide (3.4 g, 23.64) occurs and the resulting solution is stirred at 25° C. for 20 h. The reaction mixture is poured into ethyl acetate/hexanes (1:1, 200 mL) and washed sequentially with 1 M hydrochloric acid, 1 M aqueous sodium carbonate, and saturated aqueous sodium chloride. The organic layer is dried over magnesium sulfate, concentrated in vacuo, and purified by silica gel chromatography (elution with 2:1 ethyl acetate-hexane) to provide (2R,3S)-3-(Formyl-2-tetrahydropyranyloxyamino)-2-(3-phenyl-1-propyl)butanoic acid [(1S)-2,2-dimethyl-1-(methylcarbamoyl)-1-propyl]amide as a white solid (2.7 g, 36% yield).

$^1$H NMR (400 MHz, CDCl$_3$) δ8.40 and 8.02 (s, 1H), 7.22 (m, 2H), 7.08 (m, 3H), 6.38 (m, 1H), 5.88 (m, 1H), 4.82 (m, 1H), 4.38 and 3.56 (m, 1H), 4.22 (m, 1H), 3.94 (m, 1H), 2.74 (m, 3H), 2.56 (m, 3H), 1.82 (m, 2H), 1.74–1.42 (m, 10H), 1.28 and 1.22 (d, 3H), 0.96 (s, 9H) ppm.

ESI-MS m/z 498.4 (M+Na)$^+$.

EXAMPLE 1

(2R,3S)-3-(Formylhydroxyamino)-2-(3-phenyl-1-propyl)butanoic Acid [(1S)-2,2-Dimethyl-1-(methylcarbamoyl) -1-propyl]amide A solution of (2R,3S)-3-(Formyl-2-tetrahydropyranyloxyamino)-2-(3-phenyl-1-propyl) butanoic acid [(1S)-2,2-dimethyl-1-(methylcarbamoyl)-1-propyl]amide (3.0 g, 6.32 mmol) in acetic acid-water (4:1, 10 mL) is heated to 50° C. for 16 h. The reaction mixture is concentrated, then dissolved in toluene and concentrated in vacuo. The procedure is repeated once again to afford the crude product which is triturated from hot dichloromethane-diethyl ether to provide (2R,3S)-3-(Formylhydroxyamino)-2-(3-phenyl-1-propyl)butanoic acid [(1S)-2,2-dimethyl-1-(methylcarbamoyl)-1-propyl]amide as a white solid (2.3 g, 93% yield).

$^1$H NMR (400 MHz, CD$_3$OD) δ8.25 and 7.99 (s, 1H), 7.22 (m, 2H), 7.10 (m, 3H), 4.48 and 3.82 (dq, 1H), 4.24 (s, 1H), 2.84 and 2.78 (m, 1H), 2.61 (s, 3H), 2.58 (m, 1H), 2.44 (m, 2H), 1.52 (m, 4H), 1.24 and 1.18 (d, 3H), 0.99 (s, 9H) ppm.

ESI-MS m/z 414.5 (M+Na)$^+$.

Anal. Calcd. for C$_{21}$H$_{33}$N$_3$O$_4$: C, 64.42; H, 8.50; N, 10.73. Found: C, 64.44; H, 8.50; N, 10.70.

EXAMPLE 2

(2R,3S)-3-(Formylhydroxyamino)-2-(3-(4-chlorophenyl)-1-propyl)butanoic Acid [(1S)-2,2-Dimethyl-(1-methylcarbamoyl)-1-propyl]amide

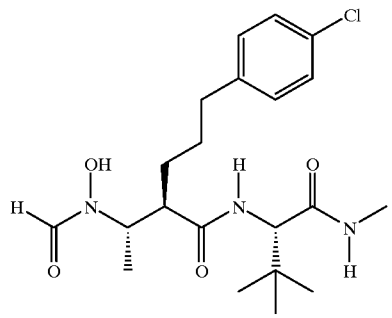

EXAMPLE 2a

Methyl (2R,3R)-2-(3-trimethylsilyl-2-propyne-1-yl)-3-hydroxybutanoate

To a solution of diisopropylamine (9.42 g, 93.22 mmol) in THF (100 mL) cooled to –50° C. is added n-butyllithium (93.22 mmol, 2.5M in hexanes) and the resulting solution is stirred at –50° C. for 0.5 h. The reaction mixture is cooled to –78° C. followed by slow addition of methyl (3R)-3-hydroxybutanoate (5 g, 42.37 mmol). After 0.5 h a solution of 3-trimethylsilyl propargyl bromide (9.76 g, 50.85 mmol) in HMPA (1 mL) is added and the reaction mixture is allowed to warm to 0° C. and stirred for 16 h. The reaction mixture is quenched by addition 10 mL of saturated aqueous ammonium chloride solution, is poured into 100 mL of 1 M hydrochloric acid, and is extracted with two 100 mL portions of ethyl acetate. The combined organic layers are dried over magnesium sulfate, concentrated in vacuo, and purified by silica gel chromatography (elution with 20% ethyl acetate-hexanes) to afford methyl (2R,3R)-2-(3-trimethylsilyl-2-propyne-1-yl)-3-hydroxybutanoate as a yellow oil (5.6 g, 58% yield).

$^1$H NMR (400 MHz, CDCl$_3$) δ4.04 (m, 1H), 3.72 (s, 3H), 2.62 (m, 3H), 1.23 (t, 3H), 0.09 (s, 9H) ppm.

ESI-MS m/z 251.2 (M+Na)$^+$.

EXAMPLE 2b (2R,3R)-2-(2-propyne-1-yl)-3-hydroxybutanoic Acid

To a solution of methyl (2R,3R)-2-(3-trimethylsilyl-2-propyne-1-yl)-3-hydroxybutanoate (5.6 g, 24.56 mmol) in THF-methanol (3:1, 160 mL) is added 2 M aqueous sodium hydroxide solution (40 mL, 36.8 mmol). The solution is stirred at 23° C. for 20 h, then concentrated and extracted with hexanes (100 mL). The aqueous layer is acidified to pH=3 with 1 M HCl and is extracted with two 100 mL portions of ethyl acetate. The combined organic layers are dried over anhydrous magnesium sulfate and concentrated under reduced pressure to provide (2R,3R)-2-(2-propyne-1-yl)-3-hydroxybutanoic acid as an oil (3.0 g, 86% yield).

$^1$H NMR (400 MHz, CDCl$_3$) δ7.28 (m, 2H), 7.16 (m, 3H), 3.93(m, 1H), 2.63 (m, 2H), 2.43 (m, 1H), 1.69 (m, 4H), 1.26 (d, 3H) ppm.

ESI-MS m/z 221.3 (M–H)$^-$.

EXAMPLE 2c (2R,3R)-2-(2-propyne-1-yl)-3-hydroxybutanoic Acid 2-Tetrahydropyranyloxyamide To a solution of (2R,3R)-2-(2-propyne-1-yl)-3-hydroxybutanoic acid (3.0 g, 21.13 mmol) in dichloromethane (50 mL) is added 2-tetrahydropyranyloxyamine (3.0 g, 25.35 mmol) and EDC (4.5 g, 23.24 mmol). The resulting solution is stirred at 23° C. for 4 h, then diluted with dichloromethane (100 mL) and washed with 1 M hydrochloric acid. The combined organic layers were dried over anhydrous magnesium sulfate and concentrated under reduced pressure to provide (2R,3R)-2-(2-propyne-1-yl)-3-hydroxybutanoic acid 2-tetrahydropyranyloxyamide as a foam (1.9 g, 37% yield). $^1$H NMR (400 MHz, CDCl$_3$) δ8.82 (bs, 1H), 4.96 (m, 1H), 3.94 (m, 2H), 3.62 (m, 1H), 2.64 (m, 1H), 2.56 (m, 1H), 2.23 (m, 1H), 2.04 (m, 1H), 1.82 (m, 2H), 1.61 (m, 4H), 1.23 (d, 3H) ppm.

ESI-MS m/z 240.3 (M–H)$^-$.

EXAMPLE 2d (3R,4S)-1-(2-Tetrahydropyranyloxy)-3-(2-propyne-1-yl)-4-methylazetidin-2-one To a solution of (2R,3R)-2-(2-propyne-1-yl)-3-hydroxybutanoic acid 2-tetrahydropyranyloxyamide (1.9 g, 7.88 mmol) in 20 mL of dichloromethane at 0° C. is added pyridine (5 mL) and methanesulfonyl chloride (0.99 g, 8.67 mmol). The resulting solution is allowed to warm to 23° C. and is stirred at 23° C. for 16 h, concentrated in vacuo, and diluted with dichloromethane (100 mL). The organic layer is washed with 1 M hydrochloric acid, saturated aqueous sodium chloride solution, dried over anhydrous magnesium sulfate, and concentrated to provide the desired methanesulfonate intermediate.

A suspension of potassium carbonate (3.26 g) in acetone (10 mL) is heated to reflux for 1 h. A solution of the above methanesulfonate in acetone (100 mL) is added and the resulting suspension is heated at reflux for 6 h. The mixture is allowed to cool to 25° C. and is filtered, concentrated under reduced pressure, and purified by silica gel chromatography (elution with 4:1 hexanes-ethyl acetate) to provide (3R,4S)-1-(2-tetrahydropyranyloxy)-3-(2-propyne-1-yl)-4-methylazetidin-2-one as an oil (1.3 g, 74% yield).

1H NMR (400 MHz, CDCl$_3$) δ5.15 (m, 0.5H), 4.99 (m, 0.5H), 4.20–4.01 (m, 2H), 3.62 (m, 1H), 3.18 (m, 1H), 2.63 (m, 1H), 2.40 (m, 1H), 1.99 (m, 1H), 1.89–1.51 (m, 6H), 1.42 (d, 1.5H), 1.38 (d, 1.5H) ppm.

ESI-MS m/z 246.3 (M+Na)$^+$.

EXAMPLE 2e (3R,4S)-1-(2-Tetrahydropyranyloxy)-3-((2E)-3-tributylstannyl-2-propene-1-yl)-4-methylazetidin-2-one To a solution of (3R,4S)-1-(2-tetrahydropyranyloxy)-3-(2-propyne-1-yl)-4-methylazetidin-2-one (1.32 g, 5.83 mmol) in 20 mL of toluene is added tributyltin hydride (1.70 g, 5.83 mmol) and AIBN (30 mg). The resulting solution is heated at reflux for 4 h then concentrated in vacuo. The reaction mixture is purified by silica gel chromatography (elution with 8:1 hexanes-ethyl acetate) to provide (3R,4S)-1-(2-tetrahydropyranyloxy)-3-((2E)-3-tributylstannyl-2-propene-1-yl)-4-methylazetidin-2-one as an oil (2.6 g, 87% yield).

$^1$H NMR (400 MHz, CDCl$_3$) δ5.94 (m, 2H), 5.16 (m, 0.5H), 4.99 (m, 0.5H), 4.20–4.01 (m, 2H), 3.62 (m, 1H), 3.12 (m, 1H), 2.61 (m, 1H), 2.36 (m, 1H), 1.76 (m, 2H), 1.58 (m, 4H), 1.44 (m, 6H), 1.26 (m, 9H), 0.86 (m, 15H) ppm.

ESI-MS m/z 538.2 (M+Na)$^+$.

EXAMPLE 2f (3R,4S)-1-(2-Tetrahydropyranyloxy)-3-((2E)-3-(4-chlorophenyl)-2-propene-1-yl)-4-methylazetidin-2-one To a solution of (3R,4S)-1-(2-tetrahydropyranyloxy)-3-((2E)-3-tributylstannyl-2-propene-1-yl)-4-methylazetidin-2-one (0.92 g, 1.79 mmol) in 3 mL of dimethylformamide is added 4-chloroiodobenzene (470 mg, 1.97 mmol) and triphenyphosphine palladium (II) dichloride (63 mg, 0.09 mmol). The resulting solution is heated at 80° C. for 16 h, then 0.5 mL ammonium hydroxide is added. The reaction mixture is poured into saturated sodium chloride solution (20 mL) and extracted with 1:1 ethyl acetate/hexane (50 mL). The combined organic layers were dried over anhydrous magnesium sulfate, concentrated under reduced pressure, and purified by silica gel chromatography (elution with 3:1 hexanes-ethyl acetate) to provide (3R,4S)-1-(2-tetrahydropyranyloxy)-3-((2E)-3-(4-chlorophenyl)-2-propene-1-yl)-4-methylazetidin-2-one as an oil (370 mg, 61% yield).

$^1$H NMR (400 MHz, CDCl$_3$) δ7.30 (d, 2H), 7.16 (d, 2H), 6.38 (m, 1H), 6.18 (m, 1H), 5.16 (m, 0.5H), 4.99 (m, 0.5H), 4.20–4.01 (m, 2H), 3.62 (m, 1H), 3.12 (m, 1H), 2.62 (m, 1H), 2.42 (m, 1H), 1.76 (m, 2H), 1.58 (m, 4H), 1.36 (m, 3H) ppm.

ESI-MS m/z 358.2 (M+Na)$^+$.

EXAMPLE 2g (3R,4S)-1-(2-Tetrahydropyranyloxy)-3-(3-(4-chlorophenyl)-1-propyl)-4-methylazetidin-2-one To a solution of (3R,4S)-1-(2-tetrahydropyranyloxy)-3-((2E)-3-(4-chlorophenyl)-2-propene-1-yl)-4-methylazetidin-2-one (0.37 g, 1.10 mmol) in 5 mL of methanol is treated with 30 mg of 5% palladium on barium sulfate. The resulting suspension is repeatedly evacuated and purged with a hydrogen balloon, then stirred under 1 atmosphere pressure of hydrogen gas for 30 h. The catalyst is filtered and the filtrate is concentrated in vacuo to provide (3R,4S)-1-(2-tetrahydropyranyloxy)-3-(3-(4-chlorophenyl)-1-propyl)-4-methylazetidin-2-one as an oil (360 mg, 97% yield).

$^1$H NMR (400 MHz, CDCl$_3$) δ7.22 (d, 2H), 7.08 (d, 2H), 5.16 (m, 0.5H), 4.96 (m, 0.5H), 4.16–3.96 (m, 2H), 3.62 (m, 1H), 2.88 (m, 1H), 2.62 (m, 2H), 1.82–1.44 (m, 10H), 1.22 (m, 3H) ppm.

ESI-MS m/z 360.3 (M+Na)$^+$.

EXAMPLE 2h (2R,3S)-2-(3-(4-chlorophenyl)-1-propyl)-3-(2-tetrahydropyranyloxyamino)butanoic Acid To a solution of (3R,4S)-1-(2-tetrahydropyranyloxy)-3-(3-(4-chlorophenyl)-1-propyl)-4-methylazetidin-2-one (360 mg, 1.07 mmol) in dioxane (3.2 mL) is added 1 M aqueous sodium hydroxide (1.6 mL). The solution is stirred at 23° C. for 72 h, then extracted with hexanes (20 mL). The aqueous layer is acidified to pH=3 with saturated aqueous sodium bisulfate solution, and is extracted with two 30 mL portions of ethyl acetate. The combined organics are washed with saturated aqueous sodium chloride, dried over anhydrous magnesium sulfate, and concentrated under reduced pressure to provide (2R,3S)-2-(3-(4-chlorophenyl)-1-propyl)-3-(2-tetrahydropyranyloxyamino)butanoic acid as an oil (380 mg, 99% yield).

$^1$H NMR (400 MHz, CDCl$_3$) δ7.22 (d, 2H), 7.06 (d, 2H), 4.92 (m, 0.5H), 4.78 (m, 0.5H), 3.95 (m. 0.5H), 3.86 (m, 0.5H), 3.57 (m, 1H), 3.36 (m, 0.5H), 3.24 (m, 0.5H), 2.94 (m, 0.5H), 2.81 (m, 0.5H), 2.62 (m, 2H), 1.94–1.66 (m, 4H), 1.62–1.44 (m, 6H), 1.24 (m, 1H), 1.08 (d, 1.5H), 1.02 (d, 1.5H) ppm.

ESI-MS m/z 354.2 (M–H)⁻.

EXAMPLE 2i (2R,3S)-2-(3-(4-chlorophenyl)-1-propyl)-3-(formyl-2-tetrahydropyranyloxyamino)butanoic Acid To a solution of (2R,3S)-2-(3-(4-chlorophenyl)-1-propyl)-3-(2-tetrahydropyranyloxyamino)butanoic acid (380 mg, 1.07 mmol) in pyridine (4 mL) at 0° C. is added formic acetic anhydride (0.9 mL). The resulting solution is allowed to warm to 25° C., stirred for 3 h, and then concentrated to dryness under reduced pressure. The resulting gum is dissolved in ethyl acetate (30 mL) and washed sequentially with 1 M hydrochloric acid (20 mL) and saturated aqueous sodium chloride solution. The organic layer is dried over anhydrous magnesium sulfate and concentrated under reduced pressure to provide (2R,3S)-2-(3-(4-chlorophenyl)-1-propyl)-3-(formyl-2-tetrahydropyranyloxyamino)butanoic acid as an oil (385 mg, 94% yield).

ESI-MS m/z 406.2 (M+Na)⁺.
ESI-MS m/z 382.3 (M–H)⁻.

EXAMPLE 2j (2R,3S)-3-(Formyl-2-tetrahydropyranyloxyamino)-2-(3-(4-chlorophenyl)-1-propyl)butanoic Acid [(1S)-2,2-Dimethyl-(1-methylcarbamoyl)-1-propyl]amide To a solution of (2R,3S)-2-(3-(4-chlorophenyl)-1-propyl)-3-(formyl-2-tetrahydropyranyloxyamino)butanoic acid (230 mg, 0.60 mmol) in DMF (2 mL) is added BOP reagent (292 mg, 0.66 mmol), HOBt (89 mg, 0.66 mmol), and NMM (182 mg, 1.80 mmol). After 30 min, addition of (2S)-2-Amino-3,3-dimethylbutanoic acid methylamide (104 mg, 0.72 mmol) occurs and the resulting solution is stirred at 25° C. for 18 h. The reaction mixture is poured into ethyl acetate/hexanes (1:1, 200 mL) and washed sequentially with 1 M hydrochloric acid, 1 M aqueous sodium carbonate, and saturated aqueous sodium chloride. The organic layer is dried over magnesium sulfate, concentrated in vacuo, and purified by silica gel chromatography (elution with 1:1 ethyl acetate-hexane) to provide (2R,3S)-3-(Formyl-2-tetrahydropyranyloxyamino)-2-(3-(4-chlorophenyl)-1-propyl)butanoic acid [(1S)-2,2-dimethyl-(1-methylcarbamoyl)-1-propyl]amide as a white solid (215 mg, 70% yield).

ESI-MS m/z 532.0 (M+Na)⁺.

EXAMPLE 2

(2R,3)-3-(Formylhydroxyamino)-2-(3-(4-chlorophenyl)-1-propyl)butanoic Acid [(1S)-2,2-Dimethyl-(1-methylcarbamoyl)-1-propyl]amide A solution of (2R,3S)-3-(Formyl-2-tetrahydropyranyloxyamino)-2-(3-(4-chlorophenyl)-1-propyl)butanoic acid [(1S)-2,2-dimethyl-(1-methylcarbamoyl)-1-propyl]amide (215 mg, 0.422 mmol) in acetic acid-water (4:1, 1 mL) is heated to 50° C. for 18 h. The reaction mixture is concentrated, then dissolved in toluene and concentrated in vacuo. The procedure is repeated once again to afford the crude product which is triturated from hot dichloromethane-diethyl ether to provide (2R,3S)-3-(Formylhydroxyamino)-2-(3-(4-chlorophenyl)-1-propyl)butanoic acid [(1S)-2,2-dimethyl-(1-methylcarbamoyl)-1-propyl]amide as a white solid (135 mg, 75% yield).

¹H NMR (400 MHz, CD₃OD) δ8.25 and 7.98 (s, 1H), 8.16 and 8.05 (m, 1H), 7.22 (d, 2H), 7.09 (d, 2H), 4.48 and 3.82 (m, 1H), 4.23 (m, 1H), 2.84 and 2.78 (m, 1H), 2.61 (s, 3H), 2.58 (m, 1H), 2.44 (m, 1H), 1.48 (m, 4H), 1.24 and 1.18 (d, 3H), 0.98 (s, 9H) ppm.

ESI-MS m/z 448.2 (M+Na)⁺.

Anal. Calcd. for C₂₁H₃₂N₃O₄Cl₁: C, 59.22; H, 7.57; N, 9.87. Found: C, 59.23; H, 7.63; N, 9.82.

EXAMPLE 3

(2R,3S)-3-(Formylhydroxyamino)-2-(3-(thiophene-2-yl)-1-propyl)butanoic Acid [(1S)-2,2-Dimethyl-(1-methylcarbamoyl)-1-propyl]amide

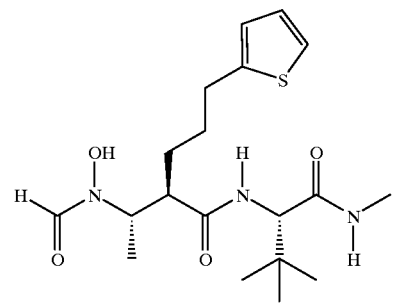

EXAMPLE 3a (3R,4S)-1-(2-Tetrahydropyranyloxy)-3-((2E)-3-(thiophene-2-yl)-2-propene-1-yl)-4-methylazetidin-2-one To a solution of (3R,4S)-1-(2-tetrahydropyranyloxy)-3-((2E)-3-tributylstannyl-2-propene-1-yl)-4-methylazetidin-2-one (400 mg, 0.78 mmol) in 1 mL of dimethylformamide is added 2-bromothiophene (152 mg, 0.93 mmol) and triphenylphosphine palladium (II) dichloride (27 mg, 0.04 mmol). The resulting solution is heated at 80° C. for 2 h, then 0.5 mL ammonium hydroxide is added. The reaction mixture is poured into saturated sodium chloride solution (20 mL) and extracted with 1:1 ethyl acetate/hexane (50 mL). The combined organic layers were dried over anhydrous magnesium sulfate, concentrated under reduced pressure, and purified by silica gel chromatography (elution with 3:1 hexanes-ethyl acetate) to provide (3R,4S)-1-(2-tetrahydropyranyloxy)-3-((2E)-3-(thiophene-2-yl)-2-propene-1-yl)-4-methylazetidin-2-one as an oil (130 mg, 54% yield).

¹H NMR (400 MHz, CDCl₃) δ7.08 (m, 1H), 6.92 (m, 1H), 6.85 (m, 1H), 6.56 (m, 1H), 6.01 (m, 1H), 5.15 (m, 0.5H), 5.00 (m, 0.5H), 4.17–4.08 (m, 2H), 3.62 (m, 1H), 3.10 (m, 1H), 2.62 (m, 1H), 2.40 (m, 1H), 1.78 (m, 2H), 1.64 (m, 4H), 1.36 (m, 3H) ppm.

ESI-MS m/z 330.2 (M+Na)⁺.

EXAMPLE 3b (3R,4S)-1-(2-Tetrahydropyranyloxy)-3-(3-(thiophene-2-yl)-1-propyl)-4-methylazetidin-2-one To a solution of (3R,4S)-1-(2-tetrahydropyranyloxy)-3-((2E)-3-(thiophene-2-yl)-2-propene-1-yl)-4-methylazetidin-2-one (130 mg, 0.423 mmol) in 3 mL of methanol is treated with 20 mg of 5% palladium on barium sulfate. The resulting suspension is repeatedly evacuated and purged with a hydrogen balloon, then stirred under 1 atmosphere pressure of hydrogen gas for 72 h. The catalyst is filtered and the filtrate is concentrated in vacuo to provide (3R,4S)-1-(2-tetrahydropyranyloxy)-3-(3-(thiophene-2-yl)-1-propyl)-4-methylazetidin-2-one as an oil (130 mg, 100% yield).

$^1$H NMR (400 MHz, CDCl$_3$) δ7.04 (m, 1H), 6.86 (m, 1H), 6.77 (m, 1H), 5.16 (m, 0.5H), 4.96 (m, 0.5H), 4.16–3.96 (m, 2H), 3.61 (m, 1H), 2.88 (m, 3H), 1.90–1.44 (m, 10H), 1.24 (m, 3H) ppm.

ESI-MS m/z 332.2 (M+Na)$^+$.

EXAMPLE 3c (2R,3S)-2-(3-(thiophene-2-yl)-1-propyl)-3-(2-tetrahydropyranyloxyamino)butanoic Acid To a solution of (3R,4S)-1-(2-tetrahydropyranyloxy)-3-(3-(thiophene-2-yl)-1-propyl)-4-methylazetidin-2-one (91 mg, 0.295 mmol) in dioxane (1 mL) is added 1 M aqueous sodium hydroxide (0.44 mL). The solution is stirred at 23° C. for 18 h, then extracted with hexanes (10 mL). The aqueous layer is acidified to pH=3 with saturated aqueous sodium bisulfate solution, and is extracted with two 20 mL portions of ethyl acetate. The combined organics are washed with saturated aqueous sodium chloride, dried over anhydrous magnesium sulfate, and concentrated under reduced pressure to provide (2R,3S)-2-(3-(thiophene-2-yl)-1-propyl)-3-(2-tetrahydropyranyloxyamino)butanoic acid as an oil (91 mg, 94% yield).

$^1$H NMR (400 MHz, CDCl$_3$) δ7.04 (m, 1H), 6.85 (m, 1H), 6.75 (m, 1H), 4.84 (m, 0.5H), 4.68 (m, 0.5H), 3.98 (m, 0.5H), 3.86 (m, 0.5H), 3.57 (m, 1H), 3.36 (m, 0.5H), 3.25 (m, 0.5H), 2.96 (m, 0.5H), 2.2.82 (m, 2.5 H), 1.94–1.66 (m, 4H), 1.62–1.44 (m, 6H), 1.37 (m, 1H), 1.06 (d, 1.5H), 1.00 (d, 1.5H) ppm.

ESI-MS m/z 338.3 (M–H)$^-$.

EXAMPLE 3d (2R,3S)-2-(3-(thiophene-2-yl)-1-propyl)-3-(formyl-2-tetrahydropyranyloxyamino)butanoic Acid To a solution of (2R,3S)-2-(3-(thiophene-2-yl)-1-propyl)-3-(2-tetrahydropyranyloxyamino)butanoic acid (91 mg, 0.278 mmol) in pyridine (1 mL) at 0° C. is added formic acetic anhydride (0.3 mL). The resulting solution is allowed to warm to 25° C., stirred for 3 h, and then concentrated to dryness under reduced pressure. The resulting gum is dissolved in ethyl acetate (30 mL) and washed sequentially with 1 M hydrochloric acid (20 mL) and saturated aqueous sodium chloride solution. The organic layer is dried over anhydrous magnesium sulfate and concentrated under reduced pressure to provide (2R,3S)-2-(3-(thiophene-2-yl)-1-propyl)-3-(formyl-2-tetrahydropyranyloxyamino)butanoic acid as an oil (90 mg, 91% yield).

ESI-MS m/z 378.1 (M+Na)$^+$.
ESI-MS m/z 354.3 (M–H)$^-$.

EXAMPLE 3e (2R,3S)-3-(Formyl-2-tetrahydropyranyloxyamino)-2-(3-(thiophene-2-yl)-1-propyl)butanoic Acid [(1S)-2,2-Dimethyl-(1-methylcarbamoyl)-1-propyl]amide To a solution of (2R,3S)-2-(3-(thiophene-2-yl)-1-propyl)-3-(formyl-2-tetrahydropyranyloxyamino)butanoic acid (70 mg, 0.197 mmol) in DMF (1 mL) is added BOP reagent (96 mg, 0.217 mmol), HOBt (29 mg, 0.217 mmol), and NMM (100 mg, 0.986 mmol). After 30 min, addition of (2S)-2-Amino-3,3-dimethylbutanoic acid methylamide (34 mg, 0.237 mmol) occurs and the resulting solution is stirred at 25° C. for 20 h. The reaction mixture is poured into ethyl acetate/hexane (1:1, 20 mL) and washed sequentially with 1 M hydrochloric acid, 1 M aqueous sodium carbonate, and saturated aqueous sodium chloride. The organic layer is dried over magnesium sulfate, concentrated in vacuo, and purified by silica gel chromatography (elution with 1:1 ethyl acetate-hexane) to provide (2R,3S)-3-(Formyl-2-tetrahydropyranyloxyamino)-2-(3-(thiophene-2-yl)-1-propyl)butanoic acid [(1S)-2,2-dimethyl-(1-methylcarbamoyl)-1-propyl]amide as a white solid (13 mg, 14% yield).

ESI-MS m/z 504.0 (M+Na)$^+$.

EXAMPLE 3

(2R,3S)-3-(Formylhydroxyamino)-2-(3-(thiophene-2-yl)-1-propyl)butanoic Acid [(1S)-2,2-Dimethyl-(1-methylcarbamoyl)-1-propyl]amide A solution of (2R,3S)-3-(Formyl-2-tetrahydropyranyloxyamino)-2-(3-(thiophene-2-yl)-1-propyl)butanoic acid [(1S)-2,2-dimethyl-(1-methylcarbamoyl)-1-propyl]amide (13 mg, 0.027 mmol) in acetic acid-water (4:1, 1 mL) is heated to 50° C. for 18 h. The reaction mixture is concentrated, then dissolved in toluene and concentrated in vacuo. The procedure is repeated once again to afford the crude product which is triturated from hot dichloromethane-diethyl ether to provide (2R,3S)-3-(Formylhydroxyamino)-2-(3-(thiophene-2-yl)-1-propyl)butanoic acid [(1S)-2,2-dimethyl-(1-methylcarbamoyl)-1-propyl]amide as a white solid (9 mg, 85% yield).

$^1$H NMR (400 MHz, CD$_3$OD) δ8.25 and 7.98 (s, 1H), 8.15 and 8.00 (m, 1H), 7.04 (m, 1H), 6.83 (m, 1H), 6.72 (m, 1H), 4.48 and 3.82 (m, 1H), 4.23 (d, 1H), 2.84–2.65 (m, 3H), 2.61 (m, 3H), 1.43 (m, 4H), 1.24 and 1.16 (d, 3H), 0.98 (s, 9H) ppm.

ESI-MS m/z 420.1 (M+Na)$^+$.

EXAMPLE 20

(2R,3S)-3-(Formylhydroxyamino)-2-(3-(4-chlorophenyl)-1-propyl)butanoic Acid [(1S)-2,2-Dimethyl-(1-(2-pyridylmethyl)carbamoyl)-1-propyl]amide

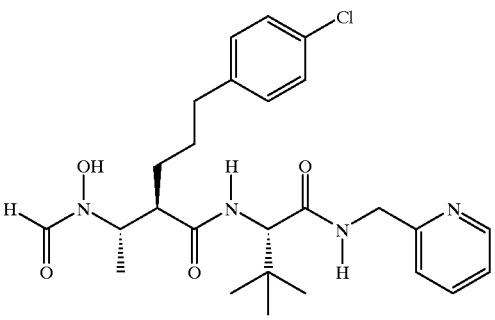

EXAMPLE 20a (2S)-2-tert-butoxycarbonylamino-3,3-dimethylbutanoic Acid 2-pyridylmethylamide To a solution of (2S)-2-tert-butoxycarbonylamino-3,3-dimethylbutanoic acid (11.6 g, 50 mmol) in dichloromethane (100 mL) is added EDC (14.4 g, 75 mmol), HOBT (7.65 g, 50 mmol), and 2-pyridylmethylamine (6.48 g, 60 mmol). The resulting solution is stirred at 25° C. for 18 h, then diluted with dichloromethane (200 mL) and washed with 2 M hydrochloric acid and 2 M sodium hydroxide. The organic layer is dried over anhydrous magnesium sulfate and concentrated in vacuo to provide (2S)-2-tert-butoxycarbonylamino-3,3-dimethylbutanoic acid 2-pyridylmethylamide as a white solid (16 g, 100% yield).

$^1$H NMR (400 MHz, d$_6$DMSO) 8.46 (d, 1H), 7.68 (t, 1H), 7.27 (d, 1H), 7.22 (dd, 1H), 6.50 (d, 1H), 4.32 (d, 2H), 3.86 (d, 1H), 1.37 (s, 9H), 0.88 (s, 9H) ppm.

EXAMPLE 20b (2S)-2-Amino-3,3-dimethylbutanoic Acid 2-pyridylmethylamide

To a solution of (2S)-2-tert-butoxycarbonylamino-3,3-dimethylbutanoic acid 2-pyridylmethylamide (16 g, 50 mmol) in dichloromethane (25 mL) cooled at 0° C. is added trifluoroacetic acid (150 mL). The resulting solution is allowed to warm to 25° C. and is stirred for 18 h. The reaction mixture is diluted with toluene, concentrated, brought to pH=10 with 2 M sodium hydroxide, and extracted with 3:1 dichloromethane/isopropanol (200 mL). The organic layer is washed with saturated aqueous sodium chloride, dried over anhydrous magnesium sulfate and concentrated under reduced pressure to provide (2S)-2-Amino-3,3-dimethylbutanoic acid 2-pyridylmethylamide (11 g, 100% yield) as a white solid.

$^1$H NMR (400 MHz, d$_6$-DMSO) δ8.43 (d, 1H), 8.35 (m, 1H), 7.72 (t, 1H), 7.27 (d, 1H), 7.21 (dd, 1H), 4.34 (d, 2H), 2.85 (s, 1H), 1.68 (bs, 2H), 0.92 (s, 9H) ppm.

EXAMPLE 20c (2R,3S)-3-(Formyl-2-tetrahydropyranyloxyamino)-2-(3-(4-chlorophenyl)-1-propyl)butanoic Acid [(1S)-2,2-Dimethyl-(1-(2-pyridylmethyl)carbamoyl)-1-propyl]amide To a solution of (2R,3S)-2-(3-(4-chlorophenyl)-1-propyl)-3-(formyl-2-tetrahydropyranyloxyamino)butanoic acid (2 g, 5.21 mmol) in DMF (15 mL) is added BOP reagent (2.53 g, 5.72 mmol), HOBt (0.77 g, 5.72 mmol), and NMM (2.1 g, 20.86 mmol). After 30 min, addition of (2S)-2-Amino-3,3-dimethylbutanoic acid 2-pyridylmethylamide (1.26 g, 5.72 mmol) occurs and the resulting solution is stirred at 25° C. for 72 h. The reaction mixture is poured into ethyl acetate (100 mL) and washed sequentially with 1 M aqueous sodium carbonate and saturated aqueous sodium chloride. The organic layer is dried over magnesium sulfate, concentrated in vacuo, and purified by silica gel chromatography (elution with ethyl acetate) to provide (2R,3S)-3-(Formyl-2-tetrahydropyranyloxyamino)-2-(3-(4-chlorophenyl)-1-propyl)butanoic acid [(1S)-2,2-dimethyl-(1-(2-pyridylmethyl)carbamoyl)-1-propyl]amide as a white solid (2.4 g, 79% yield).

ESI-MS m/z 586.9 (M+H)$^+$.

EXAMPLE 20

(2R,3S)-3-(Formylhydroxyamino)-2-(3-(4-chlorophenyl)-1-propyl)butanoic Acid [(1S)-2,2-Dimethyl-(1-(2-pyridylmethyl)carbamoyl)-1-propyl]amide A solution of (2R,3S)-3-(Formyl-2-tetrahydropyranyloxyamino)-2-(3-(4-chlorophenyl)-1-propyl)butanoic acid [(1S)-2,2-dimethyl-(1-(2-pyridylmethyl)carbamoyl)-1-propyl]amide (2.4 g, 4.09 mmol) in acetic acid-water (4:1, 10 mL) is heated to 50° C. for 36 h. The reaction mixture is concentrated, then dissolved in toluene and concentrated in vacuo. The procedure is repeated once again to afford the crude product which is recrystallized from dichloromethane/methanol-diethyl ether to provide (2R,3S)-3-(Formylhydroxyamino)-2-(3-(4-chlorophenyl)-1-propyl)butanoic acid [(1S)-2,2-dimethyl-(1-(2-pyridylmethyl)carbamoyl)-1-propyl]amide as a white solid (1.59 g, 77% yield).

$^1$H NMR (400 MHz, CD$_3$OD) δ8.63 (m, 1H), 8.40 (m, 1H), 8.25 and 7.99 (s, 1H), 8.22 and 8.16 (d, 1H), 7.61 (t, 1H), 7.29 (d, 1H), 7.21 (m, 1H), 7.08 (d, 2H), 7.00 (d, 2H), 4.57 (m, 1H), 4.52 and 3.82 (m, 1H), 4.36–4.30 (m, 2H), 2.91 and 2.82 (m, 1H), 2.56 (m, 1H), 2.41 (m, 1H), 1.44 (m, 4H), 1.26 and 1.18 (d, 3H), 1.01 (s, 9H) ppm.

ESI-MS m/z 503.1 (M+H)$^+$.

EXAMPLE 52

(2R,3S)-3-(Formylhydroxyamino)-2-(3-(4-methylphenyl)-1-propyl)butanoic Acid [(1S)-2,2-Dimethyl-(1-methylcarbamoyl)-1-propyl]amide

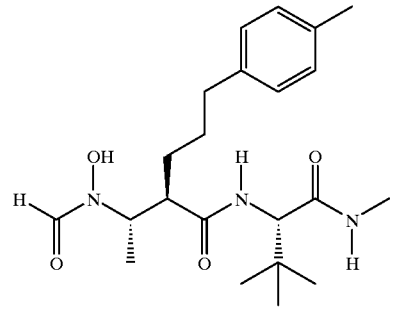

EXAMPLE 52a (3R,4S)-1-(2-Tetrahydropyranyloxy)-3-((2E)-3-(4-methylphenyl)-2-propene-1-yl)-4-methylazetidin-2-one To a solution of (3R,4S)-1-(2-tetrahydropyranyloxy)-3-((2E)-3-tributylstannyl-2-propene-1-yl)-4-methylazetidin-2-one (400 mg, 0.78 mmol) in 1 mL of dimethylformamide is added 4-bromotoluene (180 mg, 0.93 mmol) and triphenyphosphine palladium (II) dichloride (27 mg, 0.04 mmol). The resulting solution is heated at 80° C. for 18 h, then 1 mL ammonium hydroxide is added. The reaction mixture is poured into saturated sodium chloride solution (20 mL) and extracted wit 1:1 ethyl acetate/hexane (50 mL). The combined organic layers were dried over anhydrous magnesium sulfate, concentrated under reduced pressure, and purified by silica gel chromatography (elution with 3:1 hexanes-ethyl acetate) to provide (3R,4S)-1-(2-tetrahydropyranyloxy)-3-((2E)-3-(4-methylphenyl)-2-propene-1-yl)-4-methylazetidin-2-one as an oil (165 mg, 67% yield).

$^1$H NMR (400 MHz, CDCl$_3$) δ7.30 (m, 2H), 7.16 (m, 2H), 6.43 (m, 1H), 6.18 (m, 1H), 5.22 (m, 0.5H), 5.04 (m, 0.5H), 4.24–4.08 (m, 2H), 3.64 (m, 1H), 3.16 (m, 1H), 2.68 (m, 1H), 2.46 (m, 1H), 2.37 (m, 3H), 1.78 (m, 2H), 1.64 (m, 4H), 1.36 (m, 3H) ppm.

EXAMPLE 52b (3R,4S)-1-(2-Tetrahydropyranyloxy)-3-(3-(4-methylphenyl)-1-propyl)-4-methylazetidin-2-one To a solution of (3R,4S)-1-(2-tetrahydropyranyloxy)-3-((2E)-3-(4-methylphenyl)-2-propene-1-yl)-4- methylazetidin-2-one (165 mg, 0.524 mmol) in 4 mL of methanol is treated with 20 mg of 5% palladium on barium sulfate. The resulting suspension is repeatedly evacuated and purged with a hydrogen balloon, then stirred under 1 atmosphere pressure of hydrogen gas for 72 h. The catalyst is filtered and the filtrate is concentrated in vacuo to provide (3R,4S)-1-(2-tetrahydropyranyloxy)-3-(3-(4-methylphenyl)-1-propyl)-4-methylazetidin-2-one as an oil (160 mg, 96% yield).

$^1$H NMR (400 MHz, CDCl$_3$) δ7.04 (m, 4H), 5.16 (m, 0.5H), 4.96 (m, 0.5H), 4.16–3.96 (m, 2H), 3.58 (m, 1H), 2.88 (m, 1H), 2.62 (m, 2H), 2.28 (s, 3H), 1.82–1.44 (m, 10H), 1.22 (m, 3H) ppm.

EXAMPLE 52c (2R,3S)-2-(3-(4-methylphenyl)-1-propyl)-3-(2-tetrahydropyranyloxyamino)butanoic Acid To a solution of (3R,4S)-1-(2-tetrahydropyranyloxy)-3-(3-(4-methylphenyl)-1-propyl)-4-methylazetidin-2-one (160 mg, 0.51 mmol) in dioxane (1.5 mL) is added 1 M aqueous sodium hydroxide (0.75 mL). The solution is stirred at 23° C. for 20 h, then extracted with hexanes (10 mL). The aqueous layer is acidified to pH=3 with saturated aqueous sodium bisulfate solution, and is extracted with two 20 mL portions of ethyl acetate. The combined organics are washed with saturated aqueous sodium chloride, dried over anhydrous magnesium sulfate, and concentrated under reduced pressure to provide (2R,3S)-2-(3-(4-methylphenyl)-1-propyl)-3-(2-tetrahydropyranyloxyamino)butanoic acid as an oil (114 mg, 67% yield).

$^1$H NMR (400 MHz, CDCl$_3$) δ7.04 (m, 4H), 4.94 (m, 0.5H), 4.84 (m, 0.5H), 3.95 (m, 0.5H), 3.86 (m, 0.5H), 3.57 (m, 1H), 3.41 (m, 0.5H), 3.30 (m, 0.5H), 2.94 (m, 0.5H), 2.81 (m, 0.5H), 2.58 (m, 2H), 2.28 (s, 3H), 1.94–1.66 (m, 4H), 1.62–1.44 (m, 6H), 1.32 (m, 1H), 1.10 (d, 1.5H), 1.04 (d, 1.5H) ppm.

ESI-MS m/z 334.4 (M–H)$^-$.

EXAMPLE 52d (2R,3S)-2-(3-(4-methylphenyl)-1-propyl)-3-(formyl-2-tetrahydropyranyloxyamino)butanoic Acid To a solution of (2R,3S)-2-(3-(4-methylphenyl)-1-propyl)-3-(2-tetrahydropyranyloxyamino)butanoic acid (114 mg, 0.34 mmol) in pyridine (2 mL) at 0° C. is added formic acetic anhydride (0.3 mL). The resulting solution is allowed to warm to 25° C., stirred for 3 h, and then concentrated to dryness under reduced pressure. The resulting gum is dissolved in ethyl acetate (30 mL) and washed sequentially with 1 M hydrochloric acid (20 mL) and saturated aqueous sodium chloride solution. The organic layer is dried over anhydrous magnesium sulfate and concentrated under reduced pressure to provide (2R,3S)-2-(3-(4-methylphenyl)-1-propyl)-3-(formyl-2-tetrahydropyranyloxyamino)butanoic acid as an oil (120 mg, 97% yield).

ESI-MS m/z 386.3 (M+Na)$^+$.
ESI-MS m/z 362.4 (M–H)$^-$.

EXAMPLE 52e (2R,3S)-3-(Formyl-2-tetrahydropyranyloxyamino)-2-(3-(4-methylphenyl)-1-propyl)butanoic Acid [(1S)-2,2-Dimethyl-(1-methylcarbamoyl)-1-propyl]amide To a solution of (2R,3S)-2-(3-(4-methylphenyl)-1-propyl)-3-(formyl-2-tetrahydropyranyloxyamino)butanoic acid (60 mg, 0.165 mmol) in DMF (1 mL) is added BOP reagent (80 mg, 0.182 mmol), HOBt (25 mg, 0.182 mmol), and NMM (67 mg, 0.66 mmol). After 30 min, addition of (2S)-2-Amino-3,3-dimethylbutanoic acid methylamide (35 mg, 0.25 mmol) occurs and the resulting solution is stirred at 25° C. for 48 h. The reaction mixture is poured into ethyl acetate (20 mL) and washed sequentially with 1 M hydrochloric acid, 1 M aqueous sodium carbonate, and saturated aqueous sodium chloride. The organic layer is dried over magnesium sulfate, concentrated in vacuo, and purified by silica gel chromatography (elution with 2:1 ethyl acetate-hexane) to provide (2R,3S)-3-(Formyl-2-tetrahydropyranyloxyamino)-2-(3-(4-methylphenyl)-1-propyl)butanoic acid [(1S)-2,2-dimethyl-(1-methylcarbamoyl)-1-propyl]amide as a white solid (55 mg, 68% yield).

ESI-MS m/z 512.3 (M+Na)$^+$.

EXAMPLE 52

(2R,3S)-3-(Formylhydroxyamino)-2-(3-(4-methylphenyl)-1-propyl)butanoic Acid [(1S)-2,2-Dimethyl-(1-methylcarbamoyl)-1-propyl]amide A solution of (2R,3S)-3-(Formyl-2-tetrahydropyranyloxyamino)-2-(3-(4-methylphenyl)-1-propyl)butanoic acid [(1S)-2,2-dimethyl-(1-methylcarbamoyl)-1-propyl]amide (55 mg, 0.112 mmol) in acetic acid-water (4:1, 1 mL) is heated to 50° C. for 18 h. The reaction mixture is concentrated, then dissolved in toluene and concentrated in vacuo. The procedure is repeated once again to afford the crude product which is triturated from hot dichloromethane-diethyl ether to provide (2R,3S)-3-(Formylhydroxyamino)-2-(3-(4-methylphenyl)-1-propyl)butanoic acid [(1S)-2,2-dimethyl-(1-methylcarbamoyl)-1-propyl]amide as a white solid (31 mg, 68% yield).

$^1$H NMR (400 MHz, CD$_3$OD) δ8.25 and 7.98 (s, 1H), 8.12 and 8.00 (m, 1H), 6.98 (m, 4H), 4.48 and 3.82 (m, 1H), 4.23 (d, 1H), 2.84 and 2.76 (m, 1H), 2.61 (m, 3H), 2.56 (m, 1H), 2.42 (m, 2H), 2.23 (s, 3H), 1.43 (m, 4H), 1.24 and 1.18 (d, 3H), 0.98 (s, 9H) ppm.

ESI-MS m/z 428.2 (M+Na)$^+$.

Anal. Calcd. for C$_{22}$H$_{35}$N$_3$O$_4$: C, 65.16; H, 8.70; N, 10.36. Found: C, 64.99; H, 8.60; N, 10.37.

EXAMPLE 61

(2R,3S)-3-(Formylhydroxyamino)-2-(5-phenyl-1-pentyl)butanoic Acid [(1S)-2,2-Dimethyl-(1-methylcarbamoyl)-1-propyl]amide

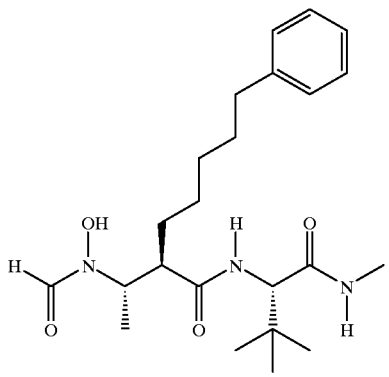

EXAMPLE 61a (3R,4S)-1-(2-Tetrahydropyranyloxy)-3-((2E),(4E,Z)-3-phenyl-2,4-pentadiene-1-yl)-4-methylazetidin-2-one To a solution of (3R,4S)-1-(2-tetrahydropyranyloxy)-3-((2E)-3-tributylstannyl-2-propene-1-yl)-4-methylazetidin-2-one (450 mg, 0.875 mmol) in 2 mL of dimethylformamide is added β-bromostyrene (212 mg, 1.05 mmol) and triphenyphosphine palladium (II) dichloride (31 mg, 0.044 mmol). The resulting solution is heated at 80° C. for 18 h, then 0.5 mL ammonium hydroxide is added. The reaction mixture is poured into saturated sodium chloride solution (20 mL) and extracted wit 1:1 ethyl acetate/hexane (50 mL). The combined organic layers were dried over anhydrous magnesium sulfate, concentrated under reduced pressure, and purified by silica gel chromatography (elution with 3:1 hexanes-ethyl acetate) to provide (3R,4S)-1-(2-tetrahydropyranyloxy)-3-((2E),(4E/Z)-3-phenyl-2,4-pentadiene-1-yl)-4-methylazetidin-2-one as an oil (140 mg, 49% yield).

$^1$H NMR (400 MHz, CDCl$_3$) δ7.41–7.18 (m, 5H), 6.78–6.36 (m, 2H), 6.43 (m, 1H), 6.22 (m, 1H), 5.83 (m, 1H), 5.16 (m, 0.5H), 5.00 (m, 0.5H), 4.18–4.02 (m, 2H), 3.64 (m, 1H), 3.04 (m, 1H), 2.58 (m, 1H), 2.36 (m, 1H), 1.78 (m, 2H), 1.64 (m, 4H), 1.32 (m, 3H) ppm.

ESI-MS m/z 350.3 (M+Na)$^+$.

EXAMPLE 61b (3R,4S)-1-(2-Tetrahydropyranyloxy)-3-(5-phenyl-1-pentyl)-4-methylazetidin-2-one To a solution of (3R,4S)-1-(2-tetrahydropyranyloxy)-3-((2E),(4E/Z)-3-phenyl-2,4-pentadiene-1-yl)-4-methylazetidin-2-one (140 mg, 0.428 mmol) in 2 mL of methanol is treated with 14 mg of 5% palladium on barium sulfate. The resulting suspension is repeatedly evacuated and purged with a hydrogen balloon, then stirred under 1 atmosphere pressure of hydrogen gas for 18 h. The catalyst is filtered and the filtrate is concentrated in vacuo to provide (3R,4S)-1-(2-tetrahydropyranyloxy)-3-(5-phenyl-1-pentyl)-4-methylazetidin-2-one as an oil (140 mg, 99% yield).

$^1$H NMR (400 MHz, CDCl$_3$) δ7.28 (m, 2H), 7.09 (m, 3H), 5.16 (m, 0.5H), 5.02 (m, 0.5H), 4.21–3.96 (m, 2H), 3.64 (m, 1H), 2.94 (m, 1H), 2.62 (m, 2H), 1.82–1.44 (m, 14H), 1.35 (m, 3H) ppm.

ESI-MS m/z 354.3 (M+Na)$^+$.

EXAMPLE 61c (2R,3S)-2-(5-phenyl-1-pentyl)-3-(2-tetrahydropyranyloxyamino)butanoic Acid To a solution of (3R,4S)-1-(2-tetrahydropyranyloxy)-3-(5-phenyl-1-pentyl)-4-methylazetidin-2-one (140 mg, 0.428 mmol) in dioxane (1.2 mL) is added 1 M aqueous sodium hydroxide (0.64 mL). The solution is stirred at 23° C. for 24 h, then extracted with hexanes (10 mL). The aqueous layer is acidified to pH=3 with saturated aqueous sodium bisulfate solution, and is extracted with two 20 mL portions of ethyl acetate. The combined organics are washed with saturated aqueous sodium chloride, dried over anhydrous magnesium sulfate, and concentrated under reduced pressure to provide (2R,3S)-2-(5-phenyl-1-pentyl)-3-(2-tetrahydropyranyloxyamino)butanoic acid as an oil (105 mg, 71% yield).

$^1$H NMR (400 MHz, CDCl$_3$) δ7.28 (m, 2H), 7.14 (m, 3H), 4.94 (m, 0.5H), 4.84 (m, 0.5H), 3.95 (mn. 0.5H), 3.86 (m, 0.5H), 3.57 (m, 1H), 3.41 (m, 0.5H), 3.30 (m, 0.5H), 2.90 (m, 0.5H), 2.78 (m, 0.5H), 2.58 (m, 2H), 1.94–1.66 (m, 4H), 1.62–1.44 (m, 6H), 1.32 (m, 5H), 1.10 (d, 1.5H), 1.04 (d, 1.5H) ppm.

ESI-MS m/z 348.4 (M–H)$^-$.

EXAMPLE 61d (2R,3S)-2-(5-phenyl-1-pentyl)-3-(formyl-2-tetrahydropyranyloxyamino)butanoic Acid To a solution of (2R,3S)-2-(5-phenyl-1-pentyl)-3-(2-tetrahydropyranyloxyamino)butanoic acid (105 mg, 0.30 mmol) in pyridine (1.5 mL) at 0° C. is added formic acetic anhydride (0.3 mL). The resulting solution is allowed to warm to 25° C., stirred for 3 h, and then concentrated to dryness under reduced pressure. The resulting gum is dissolved in ethyl acetate (30 mL) and washed sequentially with 1 M hydrochloric acid (20 mL) and saturated aqueous sodium chloride solution. The organic layer is dried over anhydrous magnesium sulfate and concentrated under reduced pressure to provide (2R,3S)-2-(5-phenyl-1-pentyl)-1-propyl)-3-(formyl-2-tetrahydropyranyloxyamino) butanoic acid as an oil (105 mg, 92% yield).

ESI-MS m/z 400.3 (M+Na)$^+$.

ESI-MS m/z 376.4 (M–H)$^-$.

EXAMPLE 61e (2R,3S)-3-(Formyl-2-tetrahydropyranyloxyamino)-2-(5-phenyl-1-pentyl)butanoic Acid [(1S)-2,2-Dimethyl-(1-methylcarbamoyl)-1-propyl]amide To a solution of (2R,3S)-2-(5-phenyl-1-pentyl)-3-(formyl-2-tetrahydropyranyloxyamino)butanoic acid (52 mg, 0.139 mmol) in DMF (1 mL) is added BOP reagent (67 mg, 0.153 mmol), HOBt (21 mg, 0.153 mmol), and NMM (42 mg, 0.42 mmol). After 30 min, addition of (2S)-2-Amino-3,3-dimethylbutanoic acid methylamide (30 mg, 0.21 mmol) occurs and the resulting solution is stirred at 25° C. for 72 h. The reaction mixture is poured into ethyl acetate (20 mL) and washed sequentially with 1 M hydrochloric acid, 1 M aqueous sodium carbonate, and saturated aqueous sodium chloride. The organic layer is dried over magnesium sulfate, concentrated in vacuo, and purified by silica gel chromatography (elution with 2:1 ethyl acetate-hexane) to provide (2R,3S)-3-(Formyl-2-tetrahydropyranyloxyamino)-2-(5-phenyl-1-pentyl)butanoic acid [(1S)-2,2-dimethyl-(1-methylcarbamoyl)-1-propyl]amide as a white solid (44 mg, 63% yield).

ESI-MS m/z 526.3 (M+Na)$^+$.

EXAMPLE 61

(2R,3S)-3-(Formylhydroxyamino)-2-(5-phenyl-1-pentyl)butanoic Acid [(1S)-2,2-Dimethyl-(1-methylcarbamoyl)-1-propyl]amide A solution of (2R,3S)-3-(Formyl-2-tetrahydropyranyloxyamino)-2-(5-phenyl-1-pentyl)butanoic acid [(1S)-2,2-dimethyl-(1-methylcarbamoyl)-1-propyl] amide (44 mg, 0.087 mmol) in acetic acid-water (4:1, 1 mL) is heated to 50° C. for 18 h. The reaction mixture is concentrated, then dissolved in toluene and concentrated in vacuo. The procedure is repeated once again to afford the crude product which is recrystallized from hot dichloromethane/methanol-diethyl ether to provide (2R,3S)-3-(Formylhydroxyamino)-2-(5-phenyl-1-pentyl)butanoic acid [(1S)-2,2-dimethyl-(1-methylcarbamoyl)-1-propyl] amide as a white solid (27 mg, 74% yield).

$^1$H NMR (400 MHz, CD$_3$OD) δ8.25 and 7.98 (s, 1H), 8.06 and 8.00 (m, 1H), 7.21 (m, 2H), 7.08 (m, 3H), 4.48 and 3.82 (m, 1H), 4.23 (d, 1H), 2.80 and 2.72 (m, 1H), 2.63 (m, 3H), 2.56 (m, 2H), 1.55 (m, 2H), 1.41 (m, 2H), 1.30–1.18 (m, 7H), 0.98 (s, 9H) ppm.

ESI-MS m/z 442.4 (M+Na)$^+$.

Anal. Calcd. for C$_{23}$H$_{37}$N$_3$O$_4$: C, 65.98; H, 8.89; N, 10.02. Found: C, 65.84; H, 8.95; N, 9.95.

PHARMACOLOGY

The efficacy of compounds of the present invention as inhibitors of matrix metalloproteases, TNFα converting enzyme and TNFα cellular release can be evaluated and measured using pharmacological methods known in the art or as described in detail below based on similarly established methodologies.

PHARMACOLOGICAL EXAMPLE 1

A. Matrix Metalloprotease Inhibition Protocol

The potency of compounds of the invention as inhibitors of 19 kD truncated collagenase-1 (MMP-1), 20 kD truncated collagenase-3 (MMP-13), stromelysin-1 (MMP-3), and 50 kD truncated gelatinase B (MMP-9) is determined according to the general procedure of Bickett et. al. (*Anal. Biochem.* 1993, 212, 58–64) using the fluorogenic substrate, DNP-Pro-Cha-Gly-Cys(Me)-His-Ala-Lys(NMA)—NH$_2$ (DNP=2, 4-dinitrophenyl, NMA=N-methylanthranilic acid). Assays are conducted in a total volume of 0.180 mL assay buffer (200 mM NaCl, 50 mM Tris, 5 mM CaCl$_2$, 10 μM ZnSO$_4$, 0.005% Brij 35, pH=7.6) in each well of a black 96 well microtiter plate. 19 kD collagenase-1, 20 kD collagenase-3, stromelysin-1, and 50 kD gelatinase B concentrations are adjusted to 500 pM, 30 pM, 5 nM, and 100 pM, respectively. A dose response is generated using an eleven-point, 3-fold serial dilution with initial starting test compound concentrations of 100, 10, or 1 μM. Inhibitor and enzyme reactions are incubated for 30 minutes at ambient temperature and then initiated with 10 μM fluorogenic substrate (above). The product formation is measured at Excitation$_{343}$/Emission$_{450}$ nm after 45–180 minutes using a Fluostar SLT fluorescence analyzer. Percent inhibition is calculated at each inhibitor concentration and the data were plotted using standard curve fitting programs. Approximate IC$_{50}$ values were determined from these curves. Assays were run at low substrate concentration ([S]<<K$_m$) such that the calculated IC$_{50}$ values are equivalent to K$_i$ within experimental error.

B. TNFα Converting Enzyme Inhibition Protocol

The potency of compounds of the invention as inhibitors of cell-free tumor necrosis factor α converting enzyme is determined as follows: Membrane preparation from Mono-Mac 6 cells (subfractionated extract from equivalent of 6×10$^6$ cells per 60 μl assay) is incubated for 1 hr with 200 nM radiolabeled substrate (Biotin-SPLAQAVRSSSRT-($^3$H)P-S—NH$_2$, 4.1 Ci/mmol, ref #0935 from Zeneca) in 10 mM hepes buffer, 250 mM sucrose, pH=7.5. The reaction is quenched by addition of streptavidin SPA beads (Amersham RPNQ0006), with excess binding capacity relative to substrate, suspended in 250 mM EDTA, pH=8.0. Binding is complete within 15 minutes and plates are counted in a Wallac 1450 Microbeta liquid scintillation counter. Percent inhibition is calculated at each inhibitor concentration and the data were plotted using standard curve fitting programs. Approximate IC$_{50}$ values were determined from these curves. Assays were run at low substrate concentration ([S]<<K$_m$) such that the calculated IC$_{50}$ values are equivalent to K$_i$ within experimental error.

C. Cell-Based TNFα Release Inhibition Protocol

The potency of compounds of the invention as inhibitors of release of soluble tumor necrosis factor α from stimulated monocytes in vitro is determined as follows: LPS/PMA solution for assay consisting of a) 4 μL of 5 mg/mL LPS stock and b) 6 μL of 10 mg/mL PMA stock are added to 500 μL of medium (RPMI 1640 (Gibco)+10% FBS+penicillin/streptomycin+1-glutamine). This solution is then diluted 1:1000 (40 ng/mL and 120 ng/mL) for use later in the assay. Compounds (10 mM) are serially diluted 1:3 in DMSO. Compound dilutions (20 μL) are added to a sterile round bottom 96 well plate (20 μL:200 μL total volume=1:10 for final concentrations of 50 μM for test compounds). Mono-Mac 6 cell suspension (130 μL, 1.5×10$^6$ cells/mL) is then added to each well resulting in 2×10$^5$ cells/well. LPS/PMA (50 μL) solution is then added to each well to begin stimulation (final concentrations of 10 ng/nL and 30 ng/mL respectively). The plate is incubated at 37° C. for 2 hours then spun at 1,500 rpm for 3 minutes to pellet cells. The supernatant (120 μL/well) is removed to a new round bottom 96 well plate and diluted 1:10 in PBS. Then, 20 μL of the supernatant is transferred to a Cistron TNFα ELISA plate and processed according to the manufacturer's instructions to quantitate levels of TNFα. Percent inhibition of TNFα release is calculated at each inhibitor concentration and the data were plotted using standard curve fitting programs. Approximate IC$_{50}$ values were determined from these curves.

Results are listed in Table 3.

TABLE 3

| Example | TNFα Converting Enzyme $K_i$ | Collagenase-1 $K_i$ | Collagenase-3 $K_i$ | Gelatinase B $K_i$ | Stromelysin-1 $K_i$ | TNFα Release Inhibition $IC_{50}$ |
|---|---|---|---|---|---|---|
| Example 1 | ++ | ++ | ++++ | ++++ | ++ | + |
| Example 2 | + | +++ | +++++ | +++++ | +++ | nd |
| Example 3 | ++ | +++ | +++++ | ++++ | ++ | nd |
| Example 9 | ++ | ++ | +++++ | ++++ | +++ | nd |
| Example 20 | + | ++ | +++++ | ++++ | ++ | nd |
| Example 24 | ++ | ++ | +++++ | ++++ | +++ | nd |
| Example 52 | ++ | ++ | ++++ | ++++ | +++ | nd |
| Example 61 | + | ++ | ++++ | ++++ | +++ | nd |

Key;
+++++ 0.001 nM–0.5 nM
++++ 0.5 nM–5 nM
+++ 5 nM–50 nM
++ 50 nM–500 nM
+ >500 nM
nd not done

D. Evaluation in Xenograft in vivo Assays

Female NU/NU mice with a weight of 21±2 g are weighed and used. Control and test animals are injected subcutaneously in the axillary region with a suspension of $2 \times 10^6$ viable tumor cells in 200 uL in PBS±matrigel on day 0. Tumors are allowed to grow for 10 to 14 days prior to drug administration. Doses of test drug are given on a mg/kg basis according to the mean body weight for each cage. For each drug, two doses are used, 30 mg/kg and 90 mg/kg, and are administered by p.o. route once a day over a 14 day time span. Tumor weight is calculated from two perpendicular caliper measurements of the tumor using the formula, tumor weight=length×width2÷2 in millimeters. For each animal, tumor weight is monitored over the course of the experiment, and expressed as the percent of the tumor's weight. For each group, the mean increase in tumor weight over the course of the experiment is calculated (tumor weightday 50–tumor weightday 14=≈tumor weight) and the results expressed as percent inhibition of tumor growth with respect to the control group [1–(≈tumor weight treated group/(≈tumor weight control group)]×100. Results are presented in Table 4. The criterion for antitumor activity is 25% inhibition of tumor growth after 2 weeks of dosing (day 14).

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for inflammatory conditions, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

TABLE 4

| Example | Colo 205 Human Colon | SW 620 Human Colon | Lewis Lung M27 Murine Lung | B16B6 Murine Melanoma | Mat Ly Lu Murine Prostate | A549 Human Lung |
|---|---|---|---|---|---|---|
| Example 1 | ++ | ++ | + | + | ++ | ++++ |

Inhibition was scored as follows:
− = 0–25% Inhibition
+ = 26–50% Inhibition
++ = 51–75% Inhibition
+++ = 76–100% Inhibition
++++ = >100% Inhibition (Tumor Regression)

What is claimed is:
1. A compound of the formula

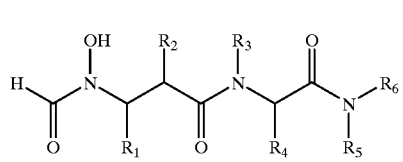
(II)

where
$R_1$ is

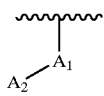

where
$A_1$ is alkylene, alkenylene, alkynylene, cycloalkylene, cycloalkenylene, arylene, heterocyclylene, heteroarylene, or a direct bond;
$A_2$ is alkyl, alkenyl, alkynyl, cycloalkyl, cycloalkenyl, heterocyclyl, heteroaryl, aryl, $NR_7R_8$, $OR_7$, $SR_7$, or hydrogen, where $R_7$ and $R_8$ are as defined below;
$R_2$ is

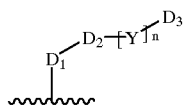

where
$D_1$ is alkylene, alkenylene, alkynylene, or a direct bond;
$D_2$ is arylene, heteroarylene, or a direct bond;
$D_3$ is aryl, heteroaryl, or heterocyclyl;
Y is alkylene, alkenylene, alkynylene, O, S, S(O), $SO_2$, $NR_9$, Se, Si, C(O), P(O)$OR_9$, P(O)$R_9$, C(O)O, C(O)$NR_9$, $NR_9$C(O), OC(O), OC(O)O, $NR_9$C(O)O, OC(O)$NR_9$, $NR_9$C(O)$NR_{10}$, or $T_1$—$T_2$ where $T_1$ and $T_2$ are, independently, lower alkylene, lower alkenylene, lower alkynylene, O, S, S(O), $SO_2$, $NR_9$, Se, Si, C(O), P(O)$OR_9$, or P(O)$R_9$, where $R_9$ and $R_{10}$ are as defined below;
n=0 or 1;
$R_3$ is hydrogen or lower alkyl;
$R_4$ is

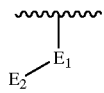

where
$E_1$ is alkylene, alkenylene, alkynylene, cycloalkylene, cycloalkenylene, arylene, heterocyclylene, heteroarylene, or a direct bond;
$E_2$ is hydrogen, $NR_{11}R_{12}$, $NR_{11}SO_2R_{12}$, $OR_{11}$, $SR_{11}$, S(O)$R_{11}$, $SO_2R_{11}$, alkyl, alkenyl, alkynyl, cycloalkyl, cycloalkenyl, heterocyclyl, aryl, or heteroaryl, where $R_{11}$ and $R_{12}$ are as defined below;

$R_5$ is hydrogen or lower alkyl;
$R_6$ is

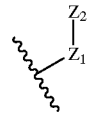

where
$Z_1$ is lower alkylene, lower alkenylene, lower alkynylene, cycloalkylene, cycloalkenylene, arylene, heterocyclylene, or a direct bond;
$Z_2$ is alkyl, alkenyl, alkynyl, cycloalkyl, cycloalkenyl, heterocyclyl, heteroaryl, aryl, $NR_{13}R_{14}$, $OR_{13}$, $SR_{13}$, $NR_{13}SO_2R_{14}$, $NR_{13}C(O)R_{14}$, $C(O)NR_{13}$, $C(O)R_{13}$, $C(O)OR_{13}$, $OC(O)R_{13}$, $S(O)R_{13}$, $SO_2R_{13}$, $SO_2NR_{13}R_{14}$, $(O(CH_2)_qO)_mR_{13}$ or hydrogen, where m, q, $R_{13}$ and $R_{14}$ are as defined below;
$R_7$, $R_8$, $R_9$, $R_{10}$, $R_{11}$, $R_{12}$, $R_{13}$, and $R_{14}$ are, independently, hydrogen, alkyl, alkynyl, alkenyl, cycloalkyl, cycloalkenyl, aryl, heterocyclyl, or heteroaryl; and where m=1–10 and q=1–10 and a pharmaceutically acceptable salt, solvate, biohydrolyzable ester, biohydrolyzable amide, affinity reagent, or prodrug thereof.
2. A compound of the formula:

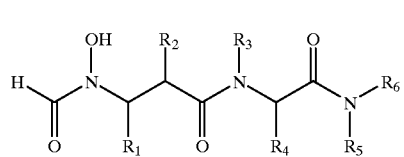
(II)

where
$R_1$ is methyl, ethyl, n-propyl, isopropyl, 4-methyl-1-pentyl, 2-thiophenesulfanylmethyl, 3-aminophenoxymethyl, 2-(3-tetrazolyl)-1-ethyl, 2-(3-pyridyl)-1-ethyl, 2-(3-furyl)-1-ethyl, 2-(2-thiazolyl)-1-ethyl, 3,3,3-trifluoro-1-propyl, 2-(4-trifluorophenyl)-1-ethyl, thiophene-3-ethynyl, 2-nitrophenoxymethyl, 3-nitrophenoxymethyl, 2-phenylsulfanylmethyl, trifluoromethyl, trichloromethyl, or vinyl;
$R_2$ is 5-methylthiophene-2-methyl, 2-furanmethyl, thiophene-2-methyl, benzothiophene-2-methyl, benzofuran-2-methyl, 4-fluorobenzyl, 3-phenyl-1-propyl, 3-phenyl-2-methyl-1-propyl, 3-(2-pyridyl)-1-propyl, 3-(thiophene-2-yl)-1-propyl, 4-phenyl-1-butyl, 3-phenyl-2-propene-1-yl, 3-(benzofuran-3-yl)-1-propyl, 3-(benzothiophene-3-yl)-1-propyl, 3-(furan-2-yl)-1-propyl, 3-(2-thiazolyl)-1-propyl, 3-(pyrimidin-2-yl)-1-propyl, 3-phenyl-2-ethyl-1-propyl, 3-(3-pyridyl)-1-propyl, 2-phenyl-1-ethyl, 3-(furan-3-yl)-1-propyl, 3-phenyl-1-butyl, 3-phenyl-2-methyl-2-propene-1-yl, 4-phenyl-3-methyl-2-butyl, 4-(3-thiophenyl)-2-butyl, benzothiophene-3-methyl, benzoxazole-2-methyl, 4-(3-furyl)-2-butyl, 3-(4-chlorophenyl)-1-propyl, 3-(4-fluorophenyl)-1-propyl, 3-(4-trifluoromethylphenyl)-1-propyl, benzyl, 5-phenyl-1-pentyl, 5-(4-chlorophenyl)-1-pentyl, 3-(4-methoxyphenyl)-1-propyl, 3-(4-methylphenyl)-1-propyl, 3-(4-biphenyl)-1-propyl, 3-(4'-fluoro-4-biphenyl)-1-propyl, 3-(4'-chloro-4-biphenyl)-1-propyl, 3-(4-phenoxyphenyl)-1-propyl, 3-(4'-chloro-4-phenoxyphenyl)-1-propyl, 3-(4'-fluoro-4-phenoxyphenyl)-1-propyl, 3-(4-thiophenoxyphenyl)-

1-propyl, 3-(4'-chloro-4-thiophenoxyphenyl)-1-propyl, 3-(4'-fluoro-4-thiophenoxyphenyl)-1-propyl, 4-(4-trifluoromethylphenyl)-1-butyl, 4-(4-chlorophenyl)-1-butyl, 4-(4-fluorophenyl)-1-butyl, 3-(4-(4-morpholino)phenyl)-1-propyl, or 3-(4-(4-methylpiperazine)phenyl)-1-propyl;

$R_3$ is hydrogen;

$R_4$ is tert-butyl, 1-phenyl-1-ethyl, 4-(benzyloxycarbonylamino)-1-butyl, 2-(2-(benzyloxycarbonylamino)-1-ethylsulfanyl)-2-propyl, 3-pyridylmethyl, 4-(2-naphthylacetylamino)-1-butyl, 3-(benzyloxycarbonylamino)-1-propyl, 3-carbamoylamino-1-propyl, benzyl, 4-hydroxybenzyl, 4-chlorobenzyl, 4-fluorobenzyl, 3-(imino-(2,3,6-trimethyl-4-methoxybenzenesulfonylamino))-methylamino-1-propyl, 4-benzyloxycarbonylaminobenzyl, isopropyl, cyclohexyl, 4-cyclopentylacetylamino-1-butyl, 4-(3-methoxybenzoylamino)-1-butyl, 4-ethoxycarbonylamino-1-butyl, 2-(2-(ethoxycarbonylamino)-1-ethylsulfanyl)-2-propyl, 2-butyl, 1-methoxy-1-ethyl, 1-hydroxy-1-ethyl, isopropyl, 2-(methoxymethylaminocarbonyl)-1-ethyl, 2-(4-ethoxycarbonyl-1-piperazinecarbonyl)-1-ethyl, 2-guanidinesulfonyl-1-ethyl, 2-methyl-4-(2-pyridylcarbonylamino)-2-butyl, 2-(methyl benzylaminocarbonyl)-1-ethyl, 2-(4-morpholinecarbonyl)-1-ethyl, 2-pyridylcarbonylaminomethyl, acetylaminomethyl, 1-isobutoxy-1-ethyl, carbamoylaminomethyl, dimethylaminocarbonylmethyl, 2-dimethylaminosulfonyl-1-ethyl, 2-methanesulfanyl-2-propyl, 2-hydroxy-2-propyl, 4-(2-pyridylcarbonylamino-1-butyl, 2-(dimethylaminocarbonyl)-1-ethyl, 2-methanesulfonyl-1-ethyl, 1-(2-pyridylmethoxy)-1-ethyl, 1-benzyloxy-1-ethyl, phenyl, 2-methyl-1-propyl, 3-(imino-(2,2,5,7,8-pentamethylchroman-6-sulfonylamino)methylamino)-1-propyl, 2-phenyl-1-ethyl, 1-(3-pyridylmethoxy)-1-ethyl, 4-pyridylmethyl, 4-methoxybenzyl, 3-indolemethyl, 2-indolemethyl, 2-naphthylmethyl, 3-naphthylmethyl, or 2-phenyl-2-propyl;

$R_5$ is hydrogen; and $R_6$ is methyl, 2-(1-pyrrolidino)-1-ethyl, 2-pyridylmethyl, 3-pyridylmethyl, 4-pyridylmethyl, cyclopropyl, cyclobutyl, cyclopentyl, 2-(4-morpholino)-1-ethyl, 3-(4-morpholino)-1-propyl, 3-(4-methylpiperazine)-1-propyl, 2-(4-methylpiperazine)-1-ethyl, 2-(2-pyridyl)-1-ethyl, 2-(3-pyridyl)-1-ethyl, 2-(4-pyridyl)-1-ethyl, tetraethyleneglycolyl methyl ether, or 2,2,2-trifluoroethyl;

and a pharmaceutically acceptable salt, solvate, biohydrolyzable ester, biohydrolyzable amide, affinity reagent, or prodrug thereof.

3. A compound of the formula:

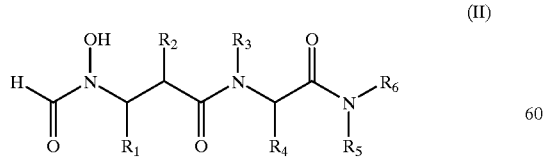

(II)

where $R_1$, $R_3$, and $R_5$ are as defined above in claim 2 and where $R_2$ is 3-(thiophene-3-yl)-1-propyl, 3-(4-pyridyl)-1-propyl, or 3-(4-t-butylphenyl)-1-propyl, $R_4$ is 1-methylbenzyl, benzyl, 3-phenylcarbonylamino-1-propyl, 2,2-dimethyl-1-propyl, 3-phenylcarbamoylamino-1-propyl, 4-pyridylmethyl, 4-methoxybenzyl, 3-indolemethyl, 2-indolemethyl, 2-naphthylmethyl, 3-naphthylmethyl, or 2-phenyl-2-propyl;

$R_6$ is hydrogen, 2-(2-pyridyl)-1-ethyl, 2-(3-pyridyl)-1-ethyl, 2-(4-pyridyl)-1-ethyl, 1-(2-aminoethyl)-piperazine, 2-(4-imidazolyl)-1-ethylamine, 4-fluorobenzyl, 4-methoxybenzyl, 2,2-dimethyl-1-propyl, or tetraethyleneglycolyl methyl ether;

and a pharmaceutically acceptable salt, solvate, biohydrolyzable ester, biohydrolyzable amide, affinity reagent, or prodrug thereof.

4. A compound of the formula:

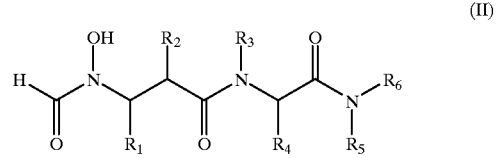

(II)

where $R_1$ is methyl, ethyl, n-propyl, isopropyl, 4-methyl-1-pentyl, 2-thiophenesulfanylmethyl, 2-(3-tetrazolyl)-1-ethyl, 2-(3-pyridyl)-1-ethyl, 2-(3-furyl)-1-ethyl, 3,3,3-trifluoro-1-propyl, 2-(4-trifluorophenyl)-1-ethyl, 2-phenylsulfanylmethyl, trifluoromethyl, or trichloromethyl;

$R_2$ is 5-methylthiophene-2-methyl, 2-furanmethyl, thiophene-2-methyl, 4-fluorobenzyl, 3-phenyl-1-propyl, 3-phenyl-2-methyl-1-propyl, 3-(2-pyridyl)-1-propyl, 3-(thiophene-2-yl)-1-propyl, 4-phenyl-1-butyl, 3-phenyl-2-propene-1-yl, 3-(furan-2-yl)-1-propyl, 3-(2-thiazolyl)-1-propyl, 3-(3-pyridyl)-1-propyl, 2-phenyl-1-ethyl, 3-(furan-3-yl)-1-propyl, benzothiophene-3-methyl, benzoxazole-2-methyl, 3-(4-chlorophenyl)-1-propyl, 3-(4-fluorophenyl)-1-propyl, 3-(4-trifluoromethylphenyl)-1-propyl, benzyl, 5-phenyl-1-pentyl, 5-(4-chlorophenyl)-1-pentyl, 3-(4-methoxyphenyl)-1-propyl, 3-(4-methylphenyl)-1-propyl, 3-(4-biphenyl)-1-propyl, 3-(4'-fluoro-4-biphenyl)-1-propyl, 3-(4'-chloro-4-biphenyl)-1-propyl, 3-(4-phenoxyphenyl)-1-propyl, 3-(4'-chloro-4-phenoxyphenyl)-1-propyl, 3-(4'-fluoro-4-phenoxyphenyl)-1-propyl, 3-(4-thiophenoxyphenyl)-1-propyl, 4-(4-trifluoromethylphenyl)-1-butyl, 4-(4-chlorophenyl)-1-butyl, 4-(4-fluorophenyl)-1-butyl, 3-(4-(4-morpholino)phenyl)-1-propyl, or 3-(4-(4-methylpiperazine)phenyl)-1-propyl;

$R_3$ is hydrogen;

$R_4$ is tert-butyl, 1-phenyl-1-ethyl, 4-(benzyloxycarbonylamino)-1-butyl, 2-(2-(benzyloxycarbonylamino)-1-ethylsulfanyl)-2-propyl, 3-pyridylmethyl, 4-(2-naphthylacetylamino)-1-butyl, 3-(benzyloxycarbonylamino)-1-propyl, 3-carbamoylamino-1-propyl, benzyl, 4-hydroxybenzyl, 4-chlorobenzyl, 4-fluorobenzyl, isopropyl, cyclohexyl, 4-cyclopentylacetylamino-1-butyl, 4-(3-methoxybenzoylamino)-1-butyl, 4-ethoxycarbonylamino-1-butyl, 2-(2-(ethoxycarbonylamino)-1-ethylsulfanyl)-2-propyl, 2-butyl, 1-methoxy-1-ethyl, 1-hydroxy-1-ethyl, isopropyl, 2-(4-ethoxycarbonyl-1-piperazinecarbonyl)-1-ethyl, 2-(methyl benzylaminocarbonyl)-1-ethyl, 2-pyridylcarbonylaminomethyl, acetylaminomethyl, 1-isobutoxy-1-ethyl, carbamoylaminomethyl, dimethylaminocarbonylmethyl, 2-dimethylaminosulfonyl-1-ethyl, 2-methanesulfanyl-2-propyl, 2-hydroxy-2-propyl, 4-(2-pyridylcarbonylamino-1-butyl, 2-(dimethylaminocarbonyl)-1-ethyl, 2-methanesulfonyl-1-ethyl, 1-(2-pyridylmethoxy)-1-ethyl, 1-benzyloxy-1-ethyl, 2-phenyl-1-ethyl, 1-(3-pyridylmethoxy)-1-ethyl, 4-pyridylmethyl, 4-methoxybenzyl, 3-indolemethyl, 2-indolemethyl, 2-naphthylmethyl, 3-naphthylmethyl, or 2-phenyl-2-propyl;

$R_5$ is hydrogen; and $R_6$ is methyl, 2-(1-pyrrolidino)-1-ethyl, 2-pyridylmethyl, 3-pyridylmethyl, 4-pyridylmethyl, cyclopropyl, cyclopentyl, 2-(4-morpholino)-1-ethyl, 3-(4-morpholino)-1-propyl, 3-(4-methylpiperazine)-1-propyl, 2-(4-methylpiperazine)-1-ethyl, 2-(2-pyridyl)-1-ethyl, 2-(3-pyridyl)-1-ethyl, 2-(4-pyridyl)-1-ethyl, tetraethyleneglycolyl methyl ether, or 2,2,2-trifluoroethyl;

and a pharmaceutically acceptable salt, solvate, biohydrolyzable ester, biohydrolyzable amide, affinity reagent, or prodrug thereof.

5. A compound of the formula:

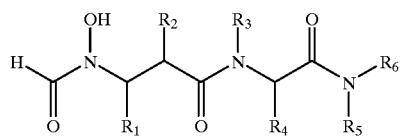

(II)

where $R_1$, $R_3$, and $R_5$ are as defined above in claim 4 and where $R_2$ is benzyl, 5-phenyl-1-pentyl or 5-(4-chlorophenyl)-1-pentyl;

or $R_4$ is 1-methylbenzyl, benzyl, 2,2-dimethyl-1-propyl, 4-pyridylmethyl, 4-methoxybenzyl, 3-indolemethyl, 2-indolemethyl, 2-naphthylmethyl, 3-naphthylmethyl, or 2-phenyl-2-propyl;

or $R_6$ is hydrogen, 2-(2-pyridyl)-1-ethyl, 2-(3-pyridyl)-1-ethyl, 2-(4-pyridyl)-1-ethyl, or tetraethyleneglycolyl methyl ether;

and a pharmaceutically acceptable salt, solvate, biohydrolyzable ester, biohydrolyzable amide, affinity reagent, or prodrug thereof.

6. A compound of the formula:

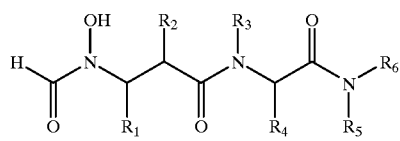

(II)

where $R_1$ is methyl, ethyl, n-propyl, isopropyl, or 3,3,3-trifluoro-1-propyl;

$R_2$ is 3-phenyl-1-propyl, 3-(4-chlorophenyl)-1-propyl, 3-(4-fluorophenyl)-1-propyl, 3-(4-trifluoromethylphenyl)-1-propyl, or 3-(thiophene-2-yl)-1-propyl;

$R_3$ is hydrogen;

$R_4$ is tert-butyl or 1-phenyl-1-ethyl;

$R_5$ is hydrogen; and $R_6$ is methyl, 2-(1-pyrrolidino)-1-ethyl, 2-pyridylmethyl, 3-pyridylmethyl, or 4-pyridylmethyl;

and a pharmaceutically acceptable salt, solvate, biohydrolyzable ester, biohydrolyzable amide, affinity reagent, or prodrug thereof.

7. A compound of the formula:

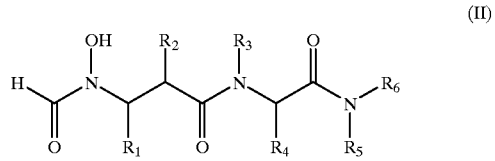

(II)

where $R_1$, $R_3$, and $R_5$ are as defined above in claim 6 and where $R_2$ is 3-(4-methylphenyl)-1-propyl, 3-(4-phenoxyphenyl)-1-propyl, or 5-phenyl-1-pentyl;

$R_3$ is hydrogen;

$R_4$ is tert-butyl or 1-phenyl-1-ethyl;

or $R_4$ is benzyl, 4-fluorobenzyl, 2-butyl, cyclohexyl, or isopropyl;

$R_5$ is hydrogen; and $R_6$ is methyl, 2-(1-pyrrolidino)-1-ethyl, 2-pyridylmethyl, 3-pyridylmethyl, or 4-pyridylmethyl; or $R_6$ is 2-(4-morpholino)-1-ethyl, 3-(4-morpholino)-1-propyl, tetraethyleneglycolyl methyl ether, 2-(2-pyridyl)-1-ethyl, 2-(3-pyridyl)-1-ethyl, or 2-(4-pyridyl)-1-ethyl;

and a pharmaceutically acceptable salt, solvate, biohydrolyzable ester, biohydrolyzable amide, affinity reagent, or prodrug thereof.

8. A compound of claim 1, wherein the compound is selected from the group consisting of:

(2R,3S)-3-(Formylhydroxyamino)-2-(3-phenyl-1-propyl)butanoic Acid [(1S)-2,2-Dimethyl-1-methylcarbamoyl)-1-propyl]amide;

(2R,3S)-3-(Formylhydroxyamino)-2-(3-(4-chlorophenyl)-1-propyl)butanoic Acid [(1S)-2,2-Dimethyl-1-methylcarbamoyl)-1-propyl]amide;

(2R,3S)-3-(Formylhydroxyamino)-2-(3-(2-thiophene)-1-propyl)butanoic Acid [(1S)-2,2-Dimethyl-1-methylcarbamoyl)-1-propyl]amide;

(2R,3S)-3-(Formylhydroxyamino)-2-(3-phenyl-1-propyl)-4-methylpentanoic Acid [(1S)-2,2-Dimethyl-1-methylcarbamoyl)-1-propyl]amide;

(2R,3S)-3-(Formylhydroxyamino)-2-(3-phenyl-1-propyl)butanoic Acid [(1S)-2-Phenyl-1-methylcarbamoyl)-1-propyl]amide;

(2R,3S)-3-(Formylhydroxyamino)-2-(3-(4-chlorophenyl)-1-propyl)-4-methyl pentanoic Acid [(1S)-2,2-Dimethyl-1-methylcarbamoyl)-1-propyl]amide;

(2R,3S)-3-(Formylhydroxyamino)-2-(3-(4-chlorophenyl)-1-propyl)-4-methyl pentanoic Acid [(1S)-2,2-Dimethyl-1-methylcarbamoyl)-1-propyl]amide;

(2R,3S)-3-(Formylhydroxyamino)-2-(3-(4-chlorophenyl)-1-propyl)-4-methyl pentanoic Acid [(1S)-2-Phenyl-1-methylcarbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(2-pyridylmethyl)carbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(3-pyridylmethyl)carbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(4-pyridylmethyl)carbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(2-(4-morpholino)-1-ethyl)carbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(2-(4-morpholino)-1-ethyl)carbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(2-(1-pyrrolidino)-1-ethyl)carbamoyl)-1-propyl]amide;

(2R,3S)-3-(Formylhydroxyamino)-2-(3-(4-chlorophenyl)-1-propyl)-4-methylpentanoic Acid [(1S)-2,2-Dimethyl-1-(3-(4-morpholino)-1-propyl)carbamoyl)-1-propyl]amide; and (2R,3S)-3-(Formylhydroxyamino)-2-(3-(4-chlorophenyl)-1-propyl)-4-methylpentanoic Acid [(1S)-2,2-Dimethyl-1-(2,2,2-trifluoroethyl)carbamoyl)-1-propyl]amide;

and a pharmaceutically acceptable salt, solvate, biohydrolyzable ester, biohydrolyzable amide, affinity reagent, or prodrug thereof.

9. A compound of claim 1, wherein the compound is selected from the compounds listed in Table 1.

10. A pharmaceutical composition comprising a pharmaceutically acceptable carrier and a pharmacologically effective amount of a compound of claim 1.

11. A pharmaceutical composition comprising a pharmaceutically acceptable carrier and a pharmacologically effective amount of the compound of claim 1 sufficient to inhibit a matrix metalloprotease.

12. A pharmaceutical composition comprising a pharmaceutically acceptable carrier and a pharmacologically effective amount of the compound of claim 1 sufficient to inhibit the cellular release of mature tumor necrosis factor alpha.

13. A pharmaceutical composition comprising a pharmaceutically acceptable carrier and a pharmacologically effective amount of the compound of claim 1 sufficient to inhibit the shedding of cell surface protein ectodomains.

14. A pharmaceutical composition comprising a pharmaceutically acceptable carrier and a pharmacologically effective amount of the of claim 1 sufficient to inhibit CD23 proteolysis.

15. A pharmaceutical composition comprising a pharmaceutically acceptable carrier and a pharmacologically effective amount of the compound of claim 1, sufficient to cause a decrease in malignant growth.

16. A pharmaceutical composition comprising a pharmaceutically acceptable carrier and a pharmacologically effective amount of the compound of claim 1, sufficient to treat arthritis.

17. A pharmaceutical composition comprising a pharmaceutically acceptable carrier and a pharmacologically effective amount of the compound of claim 1, sufficient to treat diabetes.

18. A method of inhibiting a matrix metalloprotease, comprising the step of administering to a mammal in need thereof a pharmacologically effective amount of a compound of claim 1.

19. A method of inhibiting the intracellular release of tumor necrosis factor alpha, comprising the step of administering to a mammal in need thereof a pharmacologically effective amount of a compound of claim 1.

20. A method of inhibition of shedding of cell surface protein ectodomains, comprising the step of administering to a mammal in need thereof a pharmacologically effective amount of a compound of claim 1.

21. A method of inhibition of CD23 proteolysis, comprising the step of administering to a mammal in need thereof a pharmacologically effective amount of a compound of claim 1.

* * * * *